US008933033B2

(12) United States Patent
Naylor et al.

(10) Patent No.: US 8,933,033 B2
(45) Date of Patent: Jan. 13, 2015

(54) CHAPERONIN 10 VARIANTS

(75) Inventors: Dean Jason Naylor, Carindale (AU); Richard James Brown, St. Lucia (AU); Christopher Bruce Howard, Rochedale (AU); Christopher John De Bakker, Margate (AU); Jeanette Elizabeth Stok, Greenslopes (AU); Andrew Leigh James, Barellan Point (AU); Daniel Scott Lambert, Waterford (AU); Kylie Jane Ralston, Kahibah (AU); Walter Rene Antonius Van Heumen, Bellbowrie (AU); Linda Allison Ward, Coopers Plains (AU)

(73) Assignee: CBio Limited, Queensland (AU)

( * ) Notice: Subject to any disclaimer, the term of this patent is extended or adjusted under 35 U.S.C. 154(b) by 137 days.

(21) Appl. No.: 13/500,159

(22) PCT Filed: Oct. 8, 2010

(86) PCT No.: PCT/AU2010/001327
§ 371 (c)(1),
(2), (4) Date: Jul. 30, 2012

(87) PCT Pub. No.: WO2011/041847
PCT Pub. Date: Apr. 14, 2011

(65) Prior Publication Data
US 2012/0328635 A1 Dec. 27, 2012

(30) Foreign Application Priority Data
Oct. 9, 2009 (AU) ................ 2009904956

(51) Int. Cl.
*A61K 38/00* (2006.01)
*A61K 38/16* (2006.01)
*C07K 1/00* (2006.01)
*C07K 14/47* (2006.01)
*G01N 33/50* (2006.01)
*A61K 48/00* (2006.01)

(52) U.S. Cl.
CPC ........ *C07K 14/4715* (2013.01); *G01N 33/5023* (2013.01); *G01N 33/5047* (2013.01); *A61K 38/00* (2013.01); *A61K 48/005* (2013.01)
USPC ......... 514/16.6; 514/18.6; 514/21.2; 530/350

(58) Field of Classification Search
CPC .................. A61K 38/00; A61K 38/16; A61K 2039/6043; C07K 14/47; C07K 14/00
See application file for complete search history.

(56) References Cited

U.S. PATENT DOCUMENTS

| 4,356,270 | A | 10/1982 | Itakura |
| 4,458,066 | A | 7/1984 | Caruthers et al. |
| 6,372,223 | B1 | 4/2002 | Kistner et al. |
| 7,029,678 | B2 | 4/2006 | Momin et al. |
| 7,358,329 | B2* | 4/2008 | Morton et al. ................ 530/300 |
| 2006/0205934 | A1 | 9/2006 | Macina et al. |
| 2009/0047240 | A1 | 2/2009 | Johnson et al. |
| 2009/0087410 | A1 | 4/2009 | Gearing et al. |
| 2009/0087878 | A9 | 4/2009 | La Rosa et al. |
| 2011/0082073 | A1 | 4/2011 | Naylor et al. |

FOREIGN PATENT DOCUMENTS

| CA | 2613732 A1 | 1/2007 |
| EP | 0399843 A2 | 11/1990 |
| EP | 1216053 B2 | 6/2002 |
| WO | WO-9515338 A1 | 6/1995 |
| WO | WO-2007/006939 A2 | 1/2007 |
| WO | WO-2009124353 A1 | 10/2009 |

OTHER PUBLICATIONS

Gearing 2007. Immunology and Cell Biology 85:490-494.*
Williams et al 2008. Arch Dermatol. 144:683-684.*
Vanags et al. 2006. Lancet 368:855-63.*
Bowie et al, 1990, Science 247:1306-1310.*
Wells, 1990, Biochemistry 29:8509-8517.*
Ngo et al., 1994, The Protein Folding Problem and Tertiary Structure Prediction, Merz et al., eds, Birkhauser, Boston, pp. 433-506.*
Wang et al 2001. J. Biol Chem. 276:49213-49220.*
Van Eden 2008. Curr Opin in Invest Drugs. 9:523-533.*
"International Application No. PCT/AU2010/001327, International Preliminary Report on Patentability dated Nov. 11, 2011", 13 pgs.
"International Application No. PCT/AU2010/001327 International Search Report mailed Dec. 21, 2010", 6 pgs.
McCombe, P. A, "Recombinant EPF/chaperonin 10 promotes the survival of O4-positive pro-oligodendrocytes prepared from neonatal rat brain", Cell Stress and Chaperones, 13(4), (2008), 467-474.
Baranov, V. L., et al., "Gene expression in a cell-free system on the preparative scale", *Gene*, 84, (1989), 463-466.
Beaucage, S., et al., "Deoxynucleoside Phosphoramidites—A New Class of Key Intermediate for Deoxypolynucleotide Synthesis", *Tetrahedron Letters*, 22, (1981), 1859-1862.
Brown, E. L., et al., "Chemical Synthesis and Cloning of a Tyrosine tRNA Gene", *Methods in Enzymology, vol. 68: Recombinant DNA*, (1979), 109-151.
Carell, T, et al., "A Novel Procedure for the Synthesis of Libraries Containing Small Organic Molecules" *Angew Chem Int Ed Engl*, 33 (20), (1994), 2059-2061.
Carell, T., et al., "A Solution-Phase Screening Procedure for the Isolation of Active Compounds from a Library of Molecules", *Angew Chem Int Ed Engl*, 33(20), (1994), 2061-2064.
Cho, C. Y., et al., "An Unnatural Biopolymer", Science, 261, (Sep. 1993), 1303-1305.
Dewitt, S. H., et al., ""Diversomers": An Approach to Nonpeptide, Nonologomeric Chemical Diversity", *Proc. Nat. Acad. Sci. USA*, 90(15), (1993), 6909-6913.
Erb, E., et al., "Recursive deconvolution of combinatorial chemical libraries" *Proc. Natl. Acad. Sci. USA*, 91(24), (1994), 11422-1426.

(Continued)

*Primary Examiner* — Shulamith H Shafer
(74) *Attorney, Agent, or Firm* — Ditthavong & Steiner, P.C.

(57) ABSTRACT

The invention relates generally to chaperonin 10 N-terminal variants. More specifically, the invention relates to chaperonin 10 N-terminal variants with enhanced immunomodulatory capacity and/or enhanced binding affinity for pathogen-associated molecular patterns (PAMPs) and/or damage-associated molecular patterns (DAMPs).

16 Claims, 5 Drawing Sheets

(56) References Cited

OTHER PUBLICATIONS

Fields, S, et al., "A novel genetic system to detect protein-protein interactions", *Nature*, 340(6230), (Jul. 20, 1989), 245-256.

Flanagan, J. G., et al., "The *kit* Ligand: A Cell Surface Molecule Altered in Steel Mutant Fibroblasts", *Cell*, vol. 63, (1990), 185-194.

Gallop, et al., "Applications of Combinatorial Technologies to Drug Delivery, 1. Background and Peptide Combinatorial Libraries", *J. Med. Chem.*, 37(9), (1994), 1233-1251.

Gold, L. M., "Synthesis of Bacteriophage-Specific Enzymes Directed by DNA in Vitro", *Methods in Enzymology, vol. 20: Nucleic Acids and Protein Synthesis—Part C*, (1971), 537-542.

Itakura, K., et al., "Synthesis and Use of Synthetic Oligonucleotides", Annual Review of Biochemistry, 53, (1984), 323-356.

Kohler, G., et al., "Continuous Cultures of Fused Cells Secreting Antibody of Predefined Specificity", *Nature*, 256(5517), (Aug. 7, 1975), 495-497.

Kozbor, et al., "The Production of Monoclonal Antibodies From Human Lymphocytes", *Immunology Today*, 4(3), (1983), 72-79.

Kudlicki, W., et al., "High Efficiency Cell-Free Synthesis of Proteins: Refinement of the Coupled Transcription/Translation System", *Analytical Biochemistry*, 206, (1992), 389-393.

Kumar, M., "Nano and Microparticles as Controlled Drug Delivery Devices", *J. Pharm. Pharmaceut. Sci.*, 3(2), (2000), 234-258.

Madin, K., et al., "A highly efficient and robust cell-free protein synthesis system prepared from wheat embryos: Plants apparently contain a suicide system directed at ribosomes", *Proc. Natl. Acad. Sci. USA*, 97(2), (2000), 559-564.

Narang, S. A., et al., "Improved Phosphotriester Method for the Synthesis of Gene Fragments", *Methods in Enzymology, vol. 68: Recombinant DNA*, (1979), 90-98.

Nucci, M. L., et al., "The therapeutic value of poly(ethylene glycol)-modified proteins", *Advanced Drug Delivery Reviews*, 6, (1991), 133-151.

Pelham, H. R. B., et al., "An Efficient mRNA-Dependent Translation System from Reticulocyte Lysates", *Eur. J. Biochem*, 67, (1976), 247-256.

Roberts, B. E., et al., "Efficient Translation of Tobacco Mosaic Virus RNA and Rabbit Globin 9S RNA in a Cell-Free System from Commerical Wheat Germ", *Proc. Natl. Acad. Sci. USA*, 70(8), (1973), 2330-2334.

Schröder, E., et al., *In: The Peptides, vol. 1: Methods of Peptide Synthesis*, Academic Press, Inc., New York, (1965), 72-75.

Sheffield, W. P., et al., "Modification of clearance of therapeutic and potentially therapeutic proteins",*Curr Drug Targets Cardiovasc Haematol Disord*, 1(1), (2001), 1-22.

Zubay, G., "In Vitro Synthesis of Protein in Microbial Systems", *Ann. Rev. Genet.*, 7(1 (1973), 267-287.

Zuckermann, R N., et al., "Discovery of Nanomolar Ligands for 7-Transmembrane G-Protein-Coupled Receptors from a Diverse N-(Substituted]glycine Peptoid Library", *Journal of Medicinal Chemistry*, 37(17), (Aug. 19, 1994). 2678-2685.

* cited by examiner

CHAPERONIN 10 VARIANTS

INCORPORATION BY CROSS REFERENCE

This application is a national stage application under 35 U.S.C. §371 of PCT/AU2010/001327, filed Oct. 8, 2010, and published as WO 2011/041847 A1 on Apr. 14, 2011, which claims priority to Australian provisional application no. 2009904956 filed on 9 Oct. 2009, which applications and publication are incorporated by reference as if reproduced herein and made a part hereof in their entirety, and the benefit of priority of each of which is claimed herein.

TECHNICAL FIELD

The invention relates generally to chaperonin 10 N-terminal variants. More specifically, the invention relates to chaperonin 10 N-terminal variants with enhanced immunomodulatory capacity and/or enhanced binding affinity for pathogen-associated molecular patterns (PAMPs) and/or damage-associated molecular patterns (DAMPs).

BACKGROUND

Chaperonin 10 (Cpn10), also known as early pregnancy factor (EPF) and heat shock protein 10 (Hsp10; HSPE1), functions as a molecular chaperone that facilitates the folding of cellular proteins. In particular, Cpn10 has been shown to form a complex with Chaperonin 60 (Cpn60) in the mitochondria of diverse cell types. This complex is responsible for the folding of polypeptides imported into the mitochondria, preventing peptide aggregation, and reactivating denatured proteins.

Cpn10 is thought to be involved in a number of other cellular processes in addition to its role in protein folding. For example, it has been suggested that Cpn10 regulates biological activities associated with pattern recognition receptors (PRRs). PRRs are responsible for initiating and driving immune responses upon recognition of specific ligands derived from pathogenic microorganisms known as "PAMPs" (pathogen-associated molecular patterns) (e.g. lipopeptides, glycolipids, nucleic acids) and/or host-derived ligands referred to as "DAMPs" (damage-associated molecular patterns) (e.g. nucleotides, nucleosides, DNA, proteins). For example, the binding of PAMPs to PRRs expressed by phagocytic cells (e.g. macrophages) has been shown to promote endocytosis and destruction of pathogens by the cell. Binding of PAMPs/DAMPs to PRRs also initiates cell signalling cascade(s) in various immune cells (e.g. macrophages, B lymphocytes and dendritic cells) culminating in the production and secretion of inflammatory mediators (e.g. cytokines, chemokines, reactive oxygen species etc).

Recent data suggests that Cpn10 down-regulates the production and secretion of pro-inflammatory molecules induced by PRR signalling. Cpn10 has also been implicated in the positive regulation of PRR-mediated production and secretion of anti-inflammatory molecules. The capacity of Cpn10 to modulate PRR signalling provides a means of treating a variety of diseases and disorders associated with activation of the immune system (e.g. inflammatory diseases). For example, administration of Cpn10 may be used to sequester ligands responsible for initiating PRR-signalling. This in turn suppresses the production and release of inflammatory mediators and thus inhibits immune activation and inflammation.

Despite the identification of Cpn10 as a suppressor of immune activation, there is a need for improved agents to prevent and/or treat inflammatory diseases and conditions. Ideally, such agents will be capable of binding to PRR ligands with increased affinity, thereby inhibiting the production and secretion of inflammatory molecules mediated by PRR-signalling.

SUMMARY

As demonstrated herein, specific changes to the N-terminal domain of the Cpn10 polypeptide have been found to enhance binding to PAMPs and DAMPs. This in turn is believed to enhance the immunosuppressive capacity of Cpn10 variants and in particular its affect on production and release of inflammatory mediators induced by PRR signalling.

In a first aspect, the invention provides an isolated chaperonin 10 (Cpn10) variant polypeptide sharing at least 70% sequence identity with a wild-type Cpn10 polypeptide and comprising an N-terminus extended by at least two additional amino acid residues compared to said wild-type polypeptide.

In one embodiment of the first aspect, the isolated chaperonin 10 (Cpn10) variant polypeptide shares at least 80% sequence identity with the wild-type Cpn10 polypeptide.

In another embodiment of the first aspect, the isolated chaperonin 10 (Cpn10) variant polypeptide shares at least 90% sequence identity with the wild-type Cpn10 polypeptide.

In another embodiment of the first aspect, the isolated chaperonin 10 (Cpn10) variant polypeptide shares at least 95% sequence identity with the wild-type Cpn10 polypeptide. In one embodiment of the first aspect, the isolated chaperonin 10 (Cpn10) variant polypeptide has increased immunomodulatory function compared to the wild-type Cpn10 polypeptide.

In one embodiment of the first aspect, the variant polypeptide has increased binding affinity for a pathogen-associated molecular pattern (PAMP) compared to the binding affinity of the wild-type Cpn10 for the PAMP.

In one embodiment of the first aspect, the variant polypeptide has increased binding affinity for a damage-associated molecular pattern (DAMP) compared to the binding affinity of the wild-type Cpn10 for the DAMP.

In another embodiment of the first aspect, the isolated chaperonin 10 (Cpn10) variant polypeptide has increased immunomodulatory function compared to Ala-Cpn10 (SEQ ID NO: 3).

In one embodiment of the first aspect, the variant polypeptide has increased binding affinity for a pathogen-associated molecular pattern (PAMP) compared to the binding affinity of Ala-Cpn10 (SEQ ID NO: 3) for the PAMP.

In one embodiment of the first aspect, the variant polypeptide has increased binding affinity for a damage-associated molecular pattern (DAMP) compared to the binding affinity of Ala-Cpn10 (SEQ ID NO: 3) for the DAMP.

In one embodiment of the first aspect, the PAMP comprises CpG motifs.

In one embodiment of the first aspect, the PAMP is bacterial DNA.

In one embodiment of the first aspect, the bacterial DNA comprises CpG motifs.

In one embodiment of the first aspect, the PAMP is an oligonucleotide comprising a CpG oligodeoxynucleotide motif (CpG ODN).

In one embodiment of the first aspect, the CpG ODN motif is any one or more of CpGA, CpGB and/or CpGC.

In one embodiment of the first aspect, the wild-type Cpn10 polypeptide is a human wild-type Cpn10 polypeptide consisting of the amino acid sequence set forth in SEQ ID NO: 1.

In one embodiment of the first aspect, the N-terminus of the isolated polypeptide commences with a methionine residue. The methionine residue may precede an amino acid residue selected from the group consisting of arginine, asparagine, aspartic acid, cysteine, glutamic acid, glutamine, histidine, isoleucine, leucine, lysine, methionine, phenylalanine, threonine, tryptophan, tyrosine, and valine.

In one embodiment of the first aspect, the isolated polypeptide comprises an amino acid sequence as set forth in any one of SEQ ID NOs: 9, 12, 15, 18, 24, 26, 29, 32, 38, 41, 44, 47, 49, 78, 90, or 93.

In another embodiment of the first aspect, the isolated polypeptide comprises an amino acid sequence as set forth in any one of SEQ ID NOs: 52, 55, 58, 60, 81, 84, 87, or 96.

In one embodiment of the first aspect, the variant polypeptide is not GSM-Cpn10 (SEQ ID NO: 57).

In a second aspect, the invention provides an isolated nucleic acid encoding an isolated polypeptide of the first aspect.

In one embodiment of the second aspect, the isolated nucleic acid comprises a nucleotide sequence as set forth in any one of SEQ ID NOs: 10, 13, 14, 16, 17, 19, 20, 25, 27, 28, 30, 31, 33, 34, 39, 40, 42, 43, 45, 46, 48, 50, 51, 91, 92, 94, or 95.

In one embodiment of the second aspect, the isolated nucleic acid comprises a nucleotide sequence as set forth in any one of SEQ ID NOs: 53, 54, 56, 57, 59, 61, 62, 82, 83, 85, 86, 88, 89, 97, or 98.

In a third aspect, the invention provides an isolated chaperonin 10 (Cpn10) variant polypeptide sharing at least 70% sequence identity with a wild-type Cpn10 polypeptide and comprising an N-terminus extended by one additional amino acid residue compared to said wild-type polypeptide.

In one embodiment of the third aspect, the isolated chaperonin 10 (Cpn10) variant polypeptide shares at least 80% sequence identity with the wild-type Cpn10 polypeptide.

In another embodiment of the third aspect, the isolated chaperonin 10 (Cpn10) variant polypeptide shares at least 90% sequence identity with the wild-type Cpn10 polypeptide.

In another embodiment of the third aspect, the isolated chaperonin 10 (Cpn10) variant polypeptide shares at least 95% sequence identity with the wild-type Cpn10 polypeptide.

In one embodiment of the third aspect, the isolated chaperonin 10 (Cpn10) variant polypeptide has increased immunomodulatory function compared to the wild-type Cpn10 polypeptide.

In one embodiment of the third aspect, the variant polypeptide has increased binding affinity for a pathogen-associated molecular pattern (PAMP) compared to the binding affinity of the wild-type Cpn10 for the PAMP.

In one embodiment of the third aspect, the variant polypeptide has increased binding affinity for a damage-associated molecular pattern (DAMP) compared to the binding affinity of the wild-type Cpn10 for the DAMP.

In another embodiment of the third aspect, the isolated chaperonin 10 (Cpn10) variant polypeptide has increased immunomodulatory function compared to Ala-Cpn10 (SEQ ID NO: 3).

In one embodiment of the third aspect, the variant polypeptide has increased binding affinity for a pathogen-associated molecular pattern (PAMP) compared to the binding affinity of Ala-Cpn10 (SEQ ID NO: 3) for the PAMP.

In one embodiment of the third aspect, the variant polypeptide has increased binding affinity for a damage-associated molecular pattern (DAMP) compared to the binding affinity of Ala-Cpn10 (SEQ ID NO: 3) for the DAMP.

In one embodiment of the third aspect, the PAMP comprises CpG motifs.

In one embodiment of the third aspect, the PAMP is bacterial DNA.

In one embodiment of the third aspect, the bacterial DNA comprises CpG motifs.

In one embodiment of the third aspect, the PAMP is an oligonucleotide comprising a CpG oligodeoxynucleotide motif (CpG ODN).

In one embodiment of the third aspect, the CpG ODN motif is any one or more of CpGA, CpGB and/or CpGC.

In one embodiment of the third aspect, the wild-type Cpn10 polypeptide is a human wild-type Cpn10 polypeptide consisting of the amino acid sequence set forth in SEQ ID NO: 1.

In one embodiment of the third aspect, the additional amino acid residue is a serine or proline residue.

In another embodiment of the third aspect, the additional amino acid residue is a valine, leucine, isoleucine, histidine, phenylalanine, tyrosine, tryptophan, cysteine, threonine, aspartic acid, asparagine, glutamic acid or glutamine residue.

In one embodiment of the third aspect, the isolated polypeptide comprises an amino acid sequence as set forth in SEQ ID NO: 21 or 35.

In another embodiment of the third aspect, the isolated polypeptide comprises an amino acid sequence as set forth in SEQ ID NO: 63, 64, 65, 66, 67, 68, 69, 70, 71, 72, 73, 74, or 75.

In one embodiment of the third aspect, the variant polypeptide is not Ala-Cpn10 (SEQ ID NO: 3) or Gly-Cpn10 (SEQ ID NO: 6).

In a fourth aspect, the invention provides an isolated nucleic acid encoding the isolated polypeptide of the third aspect.

In one embodiment of the fourth aspect, the isolated nucleic acid comprises a nucleotide sequence as set forth in any one of SEQ ID NOs: 7, 8, 22, 23, 36, or 37.

In a fifth aspect, the invention provides a vector comprising the isolated nucleic acid of the second or fourth aspect.

In a sixth aspect, the invention provides a host cell comprising the vector of the fifth aspect.

In a seventh aspect, the invention provides a composition comprising any one or more of:
  (a) an isolated polypeptide of the first or third aspect,
  (b) an isolated nucleic acid of the second or fourth aspect,
  (c) the vector of the fifth aspect.

In one embodiment of the seventh aspect, the composition further comprises a pharmaceutically acceptable excipient, diluent or carrier.

In an eighth aspect, the invention provides a method for suppressing immune activation in a subject, said method comprising administering to the subject a therapeutically effective amount of:
  (a) an isolated polypeptide of the first or third aspect,
  (b) an isolated nucleic acid of the second or fourth aspect,
  (c) the vector of the fifth aspect.
  (d) the composition of the seventh aspect.

In a ninth aspect, the invention provides a method for preventing or treating an inflammatory disease in a subject, said method comprising administering to the subject a therapeutically effective amount of:
  (a) an isolated polypeptide of the first or third aspect,
  (b) an isolated nucleic acid of the second or fourth aspect,
  (c) the vector of the fifth aspect.
  (d) the composition of the seventh aspect.

In one embodiment of the ninth aspect, the inflammatory disease is selected from the group consisting of rheumatoid arthritis, inflammatory bowel disease (Crohn's disease, ulcerative colitis), diabetes type I (insulin-dependent diabetes mellitus, juvenile onset diabetes), chronic fatigue syndrome, Alzheimer, Graves disease, osteoarthritis, collagen II arthritis, multiple sclerosis, systemic lupus erythematosus, autoimmune myocarditis, autoimmune ovarian disease, autoimmune thyroid disease, autoimmune neuritis, autoimmune hepatitis, autoimmune uveoretinitis, autoimmune uveitis, psoriasis, Sjogren's disease, sarcoidosis, dermatomyositis, leukocytoclastic vasculitis, myasthenia gravis, allergic encephalomyelitis, thyrotoxicosis, pernicious anemia, polymyalgia rheumatica and polymyositis chronic obstructive pulmonary disease (COPD), infectious diseases, leaky gut syndrome, cardiovascular disease (e.g. congestive heart disease), allergies (e.g. anaphylaxis, drug reactions, skin allergy, eczema, allergic rhinitis, urticaria, atopic dermatitis, allergic contact allergy, food allergy, allergic conjunctivitis, insect venom allergy), asthma, acute respiratory distress syndrome (ARDS) and atherosclerosis and infectious diseases.

In a tenth aspect, the invention provides a method of screening for an immunosuppressive agent, said method comprising:
  (a) contacting an isolated nucleic acid of the second or fourth aspect with a candidate agent under conditions suitable for binding to occur between said candidate agent and said nucleic acid, and
  (b) measuring production of a polypeptide encoded by said nucleic acid.

In an eleventh aspect, the invention provides a method of screening for an immunosuppressive agent, said method comprising contacting a mixture comprising:
  (a) an immune cell expressing a pattern recognition receptor (PRR)
  (b) a ligand for said PRR, and
  (c) an isolated polypeptide of the first or third aspect,
with a candidate agent under conditions suitable for binding to occur between said candidate agent and said polypeptide, and detecting the level of PRR-mediated cellular signalling induced by said polypeptide in said immune cell.

In one embodiment of the eleventh aspect, the detecting is performed by any one or more of:
  (a) measuring the production and/or secretion of cytokines and/or chemokines by said immune cell
  (b) measuring the expression of activation markers by said immune cell,
  (c) detecting toll-like receptor-mediated NF-κB activation in said immune cell.

In a twelfth aspect, the invention provides use of any one or more of:
  (a) an isolated polypeptide of the first or third aspect,
  (b) an isolated nucleic acid of the second or fourth aspect,
  (c) the vector of the fifth aspect.
  (d) the composition of the seventh aspect, in the preparation of a medicament for suppressing immune activation in a subject.

In a thirteenth aspect, the invention provides use of any one or more of:
  a) an isolated polypeptide of the first or third aspect,
  (b) an isolated nucleic acid of the second or fourth aspect,
  (c) the vector of the fifth aspect.
  (d) the composition of the seventh aspect,
  in the preparation of a medicament for preventing or treating an inflammatory disease in a subject.

In a fourteenth aspect, the invention provides any one or more of:
  (a) an isolated polypeptide of the first or third aspect,
  (b) an isolated nucleic acid of the second or fourth aspect,
  (c) the vector of the fifth aspect.
  (d) the composition of the seventh aspect, for use in preventing or treating an inflammatory disease in a subject.

In one embodiment of the thirteenth aspect or the fourteenth aspect, the inflammatory disease is selected from the group consisting of rheumatoid arthritis, inflammatory bowel disease (Crohn's disease, ulcerative colitis), diabetes type I (insulin-dependent diabetes mellitus, juvenile onset diabetes), chronic fatigue syndrome, Alzheimer, Graves disease, osteoarthritis, collagen II arthritis, multiple sclerosis, systemic lupus erythematosus, autoimmune myocarditis, autoimmune ovarian disease, autoimmune thyroid disease, autoimmune neuritis, autoimmune hepatitis, autoimmune uveoretinitis, autoimmune uveitis, psoriasis, Sjogren's disease, sarcoidosis, dermatomyositis, leukocytoclastic vasculitis, myasthenia gravis, allergic encephalomyelitis, thyrotoxicosis, pernicious anemia, polymyalgia rheumatica and polymyositis chronic obstructive pulmonary disease (COPD), infectious diseases, leaky gut syndrome, cardiovascular disease (e.g. congestive heart disease), allergies (e.g. anaphylaxis, drug reactions, skin allergy, eczema, allergic rhinitis, urticaria, atopic dermatitis, allergic contact allergy, food allergy, allergic conjunctivitis, insect venom allergy), asthma, acute respiratory distress syndrome (ARDS) and atherosclerosis and infectious diseases.

BRIEF DESCRIPTION OF THE DRAWINGS

A preferred embodiment of the present invention will now be described, by way of an example only, with reference to the accompanying drawings wherein:

FIGS. 2A-2C are graphs showing the degree of binding of various Cpn10 N-terminal variants to CpG ODN ligands. Results are expressed as a percentage of Alanine-Cpn10 (Ala-Cpn10) binding to the given CpG ODN ligand (i.e. CpG-A, CpG-B or CpG-C).

DEFINITIONS

Figure 1:
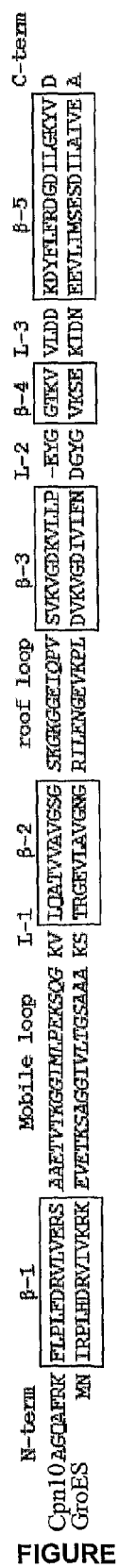
FIG. 1 shows an alignment of human Cpn10 and *E. coli* GroES amino acid sequences and corresponding boundaries of structural domains.

As used in this application, the singular form "a", "an" and "the" include plural references unless the context clearly dictates otherwise. For example, the term "a cell" also includes a plurality of cells.

As used herein, the term "comprising" means "including." Variations of the word "comprising", such as "comprise" and "comprises", have correspondingly varied meanings. Thus, for example, a polynucleotide "comprising" a sequence encoding a protein may consist exclusively of that sequence or may include one or more additional sequences.

As used herein, an "agent" includes within its scope any natural or manufactured element or compound. Accordingly, the term includes, but is not limited to, any chemical elements and chemical compounds, nucleic acids, amino acids, polypeptides, proteins, antibodies and fragments of antibodies, and other substances that may be appropriate in the context of the invention.

As used herein, the term "administering" and variations of that term including "administer" and "administration", includes contacting, applying, delivering or providing a compound (e.g. a nucleic acid, polypeptide or antibody) or composition of the invention to an organism by any appropriate means.

As used herein, the terms "antibody" and "antibodies" include IgG (including IgG1, IgG2, IgG3, and IgG4), IgA (including IgA1 and IgA2), IgD, IgE, or IgM, and IgY, whole antibodies, including single-chain whole antibodies, and antigen-binding fragments thereof. Antigen-binding antibody fragments include, but are not limited to, Fab, Fab' and F(ab')2, Fd, single-chain Fvs (scFv), single-chain antibodies, disulfide-linked Fvs (sdFv) and fragments comprising either a VL or VH domain. The antibodies may be from any animal origin. Antigen-binding antibody fragments, including single-chain antibodies, may comprise the variable region(s) alone or in combination with the entire or partial of the following: hinge region, CH1, CH2, and CH3 domains. Also included are any combinations of variable region(s) and hinge region, CH1, CH2, and CH3 domains. Antibodies may be monoclonal, polyclonal, chimeric, multispecific, humanized, and human monoclonal and polyclonal antibodies, which specifically bind the biological molecule.

As used herein, the term "nucleic acid" refers to a deoxyribonucleotide or ribonucleotide polymer in either single- or double-stranded form, and unless otherwise limited, encompasses known analogues of natural nucleotides that hybridise to nucleic acids in a manner similar to naturally occurring nucleotides.

As used herein, the term "polypeptide" means a polymer made up of amino acids linked together by peptide bonds. For the purposes of the present invention a "polypeptide" may constitute a full length protein or a portion of a full length protein.

As used herein the term "treatment", refers to any and all uses which remedy a disease state or symptoms, or otherwise prevent, hinder, retard, or reverse the progression of disease or other undesirable symptoms in any way whatsoever.

As used herein the terms "effective amount" and "therapeutically effective amount" include within their meaning a non-toxic but sufficient amount of an agent or compound to provide the desired therapeutic effect. The exact amount required will vary from subject to subject depending on factors such as the species being treated, the age and general condition of the subject, the severity of the condition being treated, the particular agent being administered and the mode of administration and so forth. Thus, it is not possible to specify an exact "effective amount". However, for any given case, an appropriate "effective amount" may be determined by one of ordinary skill in the art using only routine experimentation.

A human "wild-type Cpn10 polypeptide sequence" as used herein does not commence with a methionine residue, and may be defined by the amino acid sequence set forth in SEQ ID NO: 1.

As used herein, the terms "Alanine-Cpn10" and "Ala-Cpn10" have the same meaning and encompass any polypeptide commencing with a single additional N-terminal alanine residue compared to an otherwise identical wild-type Cpn10 polypeptide or a fragment thereof. For example, human Ala-Cpn10 as described herein commences with the amino acid sequence Ala-Ala-Gly-Gln-Ala at the N-terminus and may have the sequence set forth in SEQ ID NO: 3.

As used herein the term "substantially" means the majority but not necessarily all.

Any description of prior art documents herein, or statements herein derived from or based on those documents, is not an admission that the documents or derived statements are part of the common general knowledge of the relevant art.

For the purposes of description all documents referred to herein are incorporated by reference unless otherwise stated.

DETAILED DESCRIPTION

The present inventors have solved the X-ray crystal structure (at 2 Angstrom resolution) of a human Cpn10 variant containing an additional N-terminal alanine residue (Ala-Cpn10; SEQ ID NO: 3) and lacking the flexible mobile loops. These studies demonstrated that the Cpn10 monomer is comprised of a core anti-parallel β-barrel region flanked by a β-hairpin "roof loop" region and a "mobile loop" region. The N-terminal domain of human Cpn10 emerges from the β-barrel and initially undergoes a βhairpin turn before forming a well ordered linear extended conformation which lays across the top of the Cpn10 dome-like structure in close proximity to a specific region of the roof loops. In some crystal structures, the N-terminal domain of certain subunits within the Cpn10 heptamer was observed to undergo large conformational changes indicating that the appendage is quite flexible and likely to fulfil important biological functions such as regulating nucleic acid binding.

Without being bound to a particular mechanism or mode of action, molecular modelling performed by the inventors indicated that the flexible N-terminus of Ala-Cpn10 may dock onto the roof loop by way of an interaction between the N-terminal alanine residue (Ala-1) and a small structural pocket on the roof loop. The structural pocket is believed to be formed by residues Ser 52 to Gly57. Two key residues in the start of the roof loop, Lys53 and Lys55, are surrounded by smaller residues (Ser52, Gly54, Gly56 and Gly57), and by virtue of their extended side chain $CH_2$—$CH_2$—$CH_2$—$CH_2$—$NH_2$ are believed to form the pocket, separated by Gly54. The $CH_3$ side chain of Ala-1 is believed to interact and form one large significant cluster (and a second smaller one) with these Lys side chains. This binding of Ala-1 into the roof loop structural pocket of Lys53-Lys55 effectively is thought to anchor the flexible N-terminus, conferring tighter binding to molecules comprising nucleic acid based PAMPs or DAMPs. This tighter binding is in turn believed to enhance the immunosuppressive capacity of the protein.

The invention provides Cpn10 variants comprising modification(s) to residue(s) in the N-terminal domain. In general, Cpn10 N-terminal domain variants of the invention possess increased binding affinity for molecules comprising pathogen-associated molecular patterns (PAMPs) and/or host molecules comprising damage-associated molecular patterns (DAMPs), compared to wild-type Cpn10. Hence, binding interactions between Cpn10 polypeptides of the invention and molecules comprising PAMPs or DAMPs are generally stronger than binding interactions between wild-type Cpn10 and those same molecules. Preferably, binding interactions between the Cpn10 polypeptides of the invention and molecules comprising PAMPs or DAMPs are stronger than binding interactions between Ala-Cpn10 and those same molecules.

The binding of ligands comprising PAMPs or DAMPs to pattern recognition receptors (PRRs) initiates a series of events central to establishing effective innate immune responses. Without being limited to a particular mechanism or mode of action, it is postulated that tight binding of these ligands by Cpn10 N-terminal domain variants of the invention modifies or prevents the interaction between those ligands and their target PRRs. This in turn is believed to inhibit the initiation of immune responses instigated by PRR signalling such as, for example, those induced by the production and secretion of inflammatory molecules.

The binding of molecules comprising PAMPs or DAMPs may thus influence the nature and/or strength of immune response/s. By virtue of binding molecules comprising PAMPs or DAMPs more strongly than Ala-Cpn10 binds to those same molecules, Cpn10 N-terminal domain variants of the invention may exert increased immunomodulatory function in comparison to Ala-Cpn10.

Cpn10 N-terminal domain variants of the invention may be administered to suppress immune responses. Accordingly, the variants may be administered to prevent and/or treat a variety of diseases associated with immune activation (e.g. chronic inflammatory diseases).

Cpn10 N-terminal domain variants of the invention may also be used in screening assays to identify agonists of their activity. These agonists will generally be antagonists of PRR signalling due to enhancing the suppressive effects on PRR-signalling mediated by the variants of the invention.

Cpn10 N-Terminal Domain Variants

The invention provides Cpn10 variants comprising modification(s) to residue(s) at the N-terminal domain ("Cpn10 polypeptide(s) of the invention"). Also provided are nucleic acids encoding the Cpn10 variants ("Cpn10 nucleic acid(s) of the invention").

Typically, a Cpn10 polypeptide of the invention is an isolated polypeptide. It will be understood that the term "isolated" in this context means that the polypeptide has been removed from or is not associated with some or all of the other components with which it would be found in its natural state. For example, an "isolated" polypeptide may be removed from other amino acid sequences within a larger polypeptide sequence, or may be removed from natural components such as unrelated proteins. For the sake of clarity, an "isolated" polypeptide also includes a polypeptide which has not been taken from nature but rather has been prepared de novo, such as chemically synthesised and/or prepared by recombinant methods. As described herein an isolated Cpn10 polypeptide of the invention may be included as a component part of a longer polypeptide or fusion protein.

Typically, a Cpn10 nucleic acid of the invention is an isolated nucleic acid. It will be understood that the term "isolated" in this context means that the nucleic acid has been removed from or is not associated with some or all of the other components with which it would be found in its natural state. For example, an "isolated" nucleic acid may be removed from other nucleic acid sequences within a larger nucleic acid sequence, or may be removed from natural components such as unrelated nucleic acids. For the sake of clarity, an "isolated" nucleic acid also includes a nucleic acid which has not been taken from nature but rather has been prepared de novo, such as chemically synthesised and/or prepared by recombinant methods.

A Cpn10 polypeptide of the invention may differ from a wild-type Cpn10 polypeptide sequence by the substitution, deletion and/or insertion of one or more amino acid residue(s) in the N-terminal domain.

The skilled addressee will recognise that under normal biological conditions the initiation methionine of many mammalian wild-type Cpn10 polypeptides (e.g. the human wild-type Cpn10 polypeptide) is generally cleaved in light of the second residue being an alanine (i.e. the "N-end rule"). Accordingly, a human "wild-type Cpn10 polypeptide sequence" as contemplated herein will not commence with a methionine residue, and may be defined by the amino acid sequence set forth in SEQ ID NO: 1.

As contemplated herein, the "N-terminal domain" of Cpn10 encompasses all amino acid residues in the polypeptide sequence prior to those residues which form the first β-strand of the β-barrel in the Cpn10 monomer. Accordingly, the "N-terminal domain" of human wild-type Cpn10 sequence may be defined by residues 1-7 of the amino acid sequence set forth in SEQ ID NO: 1.

It will be understood that apart from modifications in the N-terminal domain, a Cpn10 polypeptide of the invention may otherwise be identical or substantially identical to a wild-type Cpn10 polypeptide, a variant of a wild-type Cpn10 polypeptide, or a fragment of a wild-type Cpn10 polypeptide.

The wild-type Cpn10 polypeptide may be derived from any source, non-limiting examples of which include plants (e.g. *Arabidopsis thaliana*), bacteria (e.g. *Mycobacterium tuberculosis, Escherichia coli*), yeast (e.g. *Saccharomyces cerevisiae*), nematodes (e.g. *Caenorhabditis elegans*), and animals such as mammals, frogs (e.g. *Xenopus tropicalis*), fruit flies (e.g. *Drosophila melanogaster*), chicken, fish (e.g. *Danio terio*) and other marine animals (e.g. sea squirts such as *Ciona savignyi*). Alternatively, the wild-type Cpn10 polypeptide may be archael (e.g. *Methanosarcina mazei*).

Preferably, the wild-type Cpn10 polypeptide is derived from a mammal. For example, the wild-type Cpn10 polypeptide may be a primate, ovine, bovine, equine, porcine, feline, canine, or murine Cpn10 polypeptide.

More preferably, the wild-type Cpn10 polypeptide is a human wild-type Cpn10 polypeptide. The human wild-type Cpn10 polypeptide may comprise the amino acid sequence set forth in SEQ ID NO: 1.

A Cpn10 polypeptide of the invention may thus be generated by substituting or deleting any amino acid residue(s) in the N-terminal domain of a wild-type Cpn10 polypeptide sequence, or a variant or a fragment of that polypeptide sequence (i.e. a variant or fragment thereof). Any number of amino acid(s) in the N-terminal domain may be substituted or deleted to generate a Cpn10 polypeptide of the invention, with no limitation as to the particular amino acid(s) deleted or substituted.

Additionally or alternatively, a Cpn10 polypeptide of the invention may be generated by incorporating one or more additional amino acid residues into the N-terminal domain of a wild-type Cpn10 polypeptide sequence (or a variant or fragment thereof). It will be understood that "incorporating" one or more additional amino acid residues into the N-terminal domain encompasses inserting an amino acid residue or a sequence comprising two or more amino acid residues anywhere in the N-terminal domain. Any number of additional amino acid(s) may be incorporated into the N-terminal domain with no limitation as to the identity of the amino acid(s) incorporated.

Accordingly, a Cpn10 polypeptide of the invention may comprise one or more additional amino acid residues appended to the N-terminal residue (i.e. the first residue) of a wild-type Cpn10 polypeptide sequence (or a variant or fragment thereof). The appended residue(s) may be positively charged, negatively charged, or neutral residues. The polypeptides may possess increased immunomodulatory function compared to Ala-Cpn10 (e.g. compared to human Ala-Cpn10 as set forth in SEQ ID NO: 3) and/or wild-type Cpn10 (e.g. compared to human wild-type Cpn10 as set forth in SEQ ID NO: 1). The polypeptide may possess increased binding affinity to PAMPs and/or DAMPs compared to the binding affinity of wild-type Cpn10 and/or Ala-Cpn10 to those PAMPs and/or DAMPs. The PAMP may comprise CpG motifs. For example, the PAMP may be bacterial DNA.

Cpn10 polypeptides of the invention may be generated by appending one or more neutral amino acid residue(s) to the first N-terminal residue of a wild-type Cpn10 polypeptide sequence (or a variant or fragment thereof). The additional neutral amino acid(s) may be selected from the group consisting of alanine, asparagine, cysteine, glutamine, glycine, isoleucine, leucine, methionine, phenylalanine, proline, serine, threonine, tryptophan, tyrosine and valine.

In certain embodiments, the specific chaperonin 10 N-terminal variants Ala-Cpn10 (SEQ ID NO: 3) and Gly-Cpn10 (SEQ ID NO: 6), being N-terminal variants having a single neutral amino acid residue appended to the first N-terminal residue of a wild-type Cpn10 polypeptide sequence (or a variant or fragment thereof), are excluded from the scope of the present invention.

Cpn10 polypeptides of the invention may be generated by appending one or more positively charged amino acid residue(s) to the first N-terminal residue of a wild-type Cpn10 polypeptide sequence (or a variant or fragment thereof). The positively charged amino acid(s) may be selected from the group consisting of arginine, histidine, and lysine. The polypeptides may possess increased immunomodulatory function compared to Ala-Cpn10 (e.g. compared to human Ala-Cpn10 as set forth in SEQ ID NO: 3) and/or wild-type Cpn10 (e.g. compared to human wild-type Cpn10 as set forth in SEQ ID NO: 1). The polypeptides may possess increased binding affinity to PAMPs and/or DAMPs compared to the binding affinity of wild-type Cpn10 and/or Ala-Cpn10 to those PAMPs and/or DAMPs. The PAMP may comprise CpG motifs. For example, the PAMP may be bacterial DNA.

Cpn10 polypeptides of the invention may comprise the amino acid sequence set forth in SEQ ID NO: 66, or a fragment thereof. The fragment comprises at least the first amino acid residue of the N-terminal domain sequence defined by SEQ ID NO: 66.

Cpn10 polypeptides of the invention may share at least about 40%, 45%, 50%, 55%, 60%, 65%, 70%, 75%, 80%, 85%, 90%, or 95% sequence identity with a polypeptide comprising the amino acid sequence set forth in SEQ ID NO: 66, or a fragment thereof. The fragment comprises at least the first amino acid residue of an N-terminal domain sequence defined by SEQ ID NO: 66.

Cpn10 polypeptides of the invention may be generated by appending one or more negatively charged amino acid residue(s) to the first N-terminal residue of a wild-type Cpn10 polypeptide sequence (or a variant or fragment thereof). The negatively charged amino acid(s) may be selected from the group consisting of aspartic acid and glutamic acid. The polypeptides may possess increased immunomodulatory function compared to Ala-Cpn10 (e.g. compared to human Ala-Cpn10 as set forth in SEQ ID NO: 3) and/or wild-type Cpn10 (e.g. compared to human wild-type Cpn10 as set forth in SEQ ID NO: 1). The polypeptides may possess increased binding affinity to PAMPs and/or DAMPs compared to the binding affinity of wild-type Cpn10 and/or Ala-Cpn10 to those PAMPs and/or DAMPs. The PAMP may comprise CpG motifs. For example, the PAMP may be bacterial DNA.

Cpn10 polypeptides of the invention may comprise the amino acid sequence set forth in SEQ ID NO: 72 or 74, or a fragment thereof. The fragment comprises at least the first amino acid residue of the N-terminal domain sequence defined by SEQ ID NO: 72 or 74.

Cpn10 polypeptides of the invention may share at least about 40%, 45%, 50%, 55%, 60%, 65%, 70%, 75%, 80%, 85%, 90%, or 95% sequence identity with a polypeptide comprising the amino acid sequence set forth in SEQ ID NO: 72 or 74, or a fragment thereof. The fragment comprises at least the first amino acid residue of an N-terminal domain sequence defined by SEQ ID NO: 72 or 74.

In some embodiments, Cpn10 polypeptides of the invention are generated by appending a sequence comprising two or more amino acid residues to the first N-terminal residue of a wild-type Cpn10 polypeptide sequence (or a variant or fragment thereof). The polypeptides may possess increased immunomodulatory function compared to Ala-Cpn10 (e.g. compared to human Ala-Cpn10 as set forth in SEQ ID NO: 3) and/or wild-type Cpn10 (e.g. compared to human wild-type Cpn10 as set forth in SEQ ID NO: 1). The polypeptides may possess increased binding affinity to PAMPs and/or DAMPs compared to the binding affinity of wild-type Cpn10 and/or Ala-Cpn10 to those PAMPs and/or DAMPs. The PAMP may comprise CpG motifs. For example, the PAMP may be bacterial DNA.

The appended sequence of amino acid residues may comprise a combination of differently charged amino acids. For example, the sequence may comprise a combination of neutral amino acid residue(s) and positively charged residue(s), or a combination of neutral amino acid residue(s) and negatively charged residue(s).

The skilled addressee will recognise that biological systems for protein translation commence with translation of an ATG initiation codon producing a methionine residue. In the case of Cpn10, it has been determined that the initiation methionine may be cleaved from the final (wild-type) polypeptide depending on the identity of the adjacent residue. More specifically, it has been determined that the initiation methionine is cleaved off wild-type Cpn10 when the adjacent amino acid is alanine, glycine, proline, or a serine. For example, as mentioned above, human wild-type Cpn10 generally commences with an alanine residue under biological conditions (i.e. initiation methionine cleaved) whereas the *E. coli* homologue GroES commences with a methionine followed by an asparagine (i.e. initiation methionine is not cleaved).

Despite the tendency of biological systems to cleave the initiating methionine of the Cpn10 polypeptide in some cases, it will be recognised that Cpn10 polypeptides of the invention may be synthesised using alternative means (e.g. by chemical synthesis) and/or modified to maintain or remove an initiating methionine. Accordingly, Cpn10 polypeptides of the invention may or may not commence with an initiating methionine residue.

The present inventors have determined that the addition of a methionine residue to the N-terminus of Cpn10 facilitates tighter binding to molecules comprising PAMPs or DAMPs. Without limitation to a particular mechanism or mode of action, it is proposed that the large side chain of methionine ($CH_2$—$CH_2$—S—$CH_3$) undergoes multiple interactions with residues in the roof loop of the Cpn10 molecule (e.g. isoleucine 59 (Ile59) and/or valine 62 (Val62) of SEQ ID NO: 1) located outside of the putative binding pocket identified by the inventors.

Accordingly, in certain embodiments Cpn10 polypeptides of the invention are generated by appending a sequence comprising two or more amino acid residues to the first N-terminal residue of a wild-type Cpn10 polypeptide sequence (or a variant or fragment thereof), wherein one or more residues of the appended sequence is a methionine. The polypeptides may possess increased immunomodulatory function compared to Ala-Cpn10 (e.g. compared to human Ala-Cpn10 as set forth in SEQ ID NO: 3) and/or wild-type Cpn10 (e.g. compared to human wild-type Cpn10 as set forth in SEQ ID NO: 1). The polypeptides may possess increased binding affinity to PAMPs and/or DAMPs compared to the binding affinity of wild-type Cpn10 and/or Ala-Cpn10 to those PAMPs and/or DAMPs. The PAMP may comprise CpG motifs. For example, the PAMP may be bacterial DNA.

In some embodiments, the sequence comprises a methionine residue appended to the N-terminal residue of the wild-type Cpn10 polypeptide sequence (or variant or fragment thereof).

In certain embodiments, the specific chaperonin 10 N-terminal variant GSM-Cpn10 (SEQ ID NO: 57), being an N-terminal variant having three neutral amino acid residues appended to the first N-terminal residue of a wild-type Cpn10 polypeptide sequence (or a variant or fragment thereof), is excluded from the scope of the present invention.

In other embodiments, the sequence comprises an alternative residue (i.e. a residue other than methionine) appended to the N-terminal residue of the wild-type Cpn10 polypeptide sequence (or variant or fragment thereof). The amino acid appended of the sequence appended to the N-terminal residue may be selected from the group consisting of arginine, asparagine, aspartic acid, cysteine, glutamic acid, glutamine, histidine, isoleucine, leucine, lysine, phenylalanine, serine, threonine, tryptophan, tyrosine or valine.

Preferably, the appended sequence comprises at least one methionine residue preceding one or more additional amino acid residues. The final amino acid residue of the sequence is appended to the N-terminal residue of the wild-type Cpn10 polypeptide sequence (or variant or fragment thereof). The final amino acid residue may be a neutral amino acid residue, or a charged amino acid residue. One or more additional residues may separate the methionine residue and the residue appended the N-terminal.

Preferably, the appended sequence comprises a first methionine residue preceding a second amino acid residue. The second amino acid residue of the sequence is appended to the N-terminal residue of the wild-type Cpn10 polypeptide sequence (or variant or fragment thereof). The second amino acid residue may be a neutral amino acid residue, or a charged amino acid residue.

In certain embodiments, Cpn10 polypeptides of the invention are generated by appending one neutral amino acid residue to the first N-terminal residue of a human wild-type polypeptide sequence. The polypeptides may possess increased immunomodulatory function compared to Ala-Cpn10 (e.g. compared to human Ala-Cpn10 as set forth in SEQ ID NO: 3) and/or wild-type Cpn10 (e.g. compared to human wild-type Cpn10 as set forth in SEQ ID NO: 1). The polypeptides may possess increased binding affinity to PAMPs and/or DAMPs compared to the binding affinity of wild-type Cpn10 and/or Ala-Cpn10 to those PAMPs and/or DAMPs. The PAMP may comprise CpG motifs. For example, the PAMP may be bacterial DNA.

In certain embodiments, the specific chaperonin 10 N-terminal variants Ala-Cpn10 (SEQ ID NO: 3) and Gly-Cpn10 (SEQ ID NO: 6), being N-terminal variants having a single neutral amino acid residue appended to the first N-terminal residue of a wild-type Cpn10 polypeptide sequence (or a variant or fragment thereof), are excluded from the scope of the present invention. Cpn10 polypeptides of the invention may comprise the amino acid sequence set forth in SEQ ID NO: 6, 21, 35, 63, 64, 65, 67, 68, 69, 70, 71, 73, or 75, or a fragment thereof. The fragment comprises at least the first amino acid residue of the N-terminal domain sequence defined by SEQ ID NO: 6, 21, or 35.

Cpn10 polypeptides of the invention may share at least about 40%, 45%, 50%, 55%, 60%, 65%, 70%, 75%, 80%, 85%, 90%, or 95% sequence identity with a polypeptide comprising the amino acid sequence set forth in SEQ ID NO: 6, 21, 35, 63, 64, 65, 67, 68, 69, 70, 71, 73, or 75, or a fragment thereof. The fragment comprises at least the first amino acid residue of an N-terminal domain sequence defined by SEQ ID NO: 6, 21, or 35.

A Cpn10 nucleic acid sequence of the invention may comprise the nucleotide sequence set forth in any one of SEQ ID NOs: 7, 8, 22, 23, 36 or 37, or a fragment thereof. The fragment encodes at the least the first amino acid residue of an N-terminal domain sequence encoded by any one of the aforementioned SEQ ID NOs.

Cpn10 nucleic acid sequences of the invention may share at least about 40%, 45%, 50%, 55%, 60%, 65%, 70%, 75%, 80%, 85%, 90%, or 95% sequence identity with a nucleic acid comprising the nucleotide sequence set forth in any one of SEQ ID NOs: 7, 8, 22, 23, 36 or 37, or a fragment thereof. The fragment encodes at the least the first amino acid residue of an N-terminal domain sequence encoded by any one of the aforementioned SEQ ID NOs.

In other embodiments, Cpn10 polypeptides of the invention are generated by appending a sequence comprising two neutral amino acid residues to the first N-terminal residue of a human wild-type polypeptide sequence. The first amino acid residue of the appended sequence may be a methionine. The polypeptides may possess increased immunomodulatory function compared to Ala-Cpn10 (e.g. compared to human Ala-Cpn10 as set forth in SEQ ID NO: 3) and/or wild-type Cpn10 (e.g. compared to human wild-type Cpn10 as set forth in SEQ ID NO: 1). The polypeptides may possess increased binding affinity to PAMPs and/or DAMPs compared to the binding affinity of wild-type Cpn10 and/or Ala-Cpn10 to those PAMPs and/or DAMPs. The PAMP may comprise CpG motifs. For example, the PAMP may be bacterial DNA.

Cpn10 polypeptides of the invention may comprise the amino acid sequence set forth in any one of SEQ ID NOs: 9, 12, 15, 24, 26, 29, 32, 38, 44, 49, 52, 55, 76, 78, 84, or 96, or a fragment thereof. The fragment comprises at least the first two amino acid residues of an N-terminal domain sequence defined by any one of the aforementioned SEQ ID NOs.

Cpn10 polypeptides of the invention may share at least about 40%, 45%, 50%, 55%, 60%, 65%, 70%, 75%, 80%, 85%, 90%, or 95% sequence identity with a polypeptide comprising the amino acid sequence set forth in any one of SEQ ID NOs: 9, 12, 15, 24, 26, 29, 32, 38, 44, 49, 52, 55, 76, 78, 84, or 96, or a fragment thereof. The fragment comprises at least the first two amino acid residues of an N-terminal domain sequence defined by any one of the aforementioned SEQ ID NOs.

A Cpn10 nucleic acid sequence of the invention may comprise the nucleotide sequence set forth in any one of SEQ ID NOs: 10, 13, 14, 16, 17, 25, 27, 28, 30, 31, 33, 34, 39, 40, 45, 46, 50, 51, 53, 54, 56, 57, 85, 86, 97, or 98, or a fragment thereof. The fragment encodes at the least the first two amino acid residues of an N-terminal domain sequence encoded by any one of the aforementioned SEQ ID NOs.

Cpn10 nucleic acid sequences of the invention may share at least about 40%, 45%, 50%, 55%, 60%, 65%, 70%, 75%, 80%, 85%, 90%, or 95% sequence identity with a nucleic acid comprising the nucleotide sequence set forth in any one of SEQ ID NOs: 10, 13, 14, 16, 17, 25, 27, 28, 30, 31, 33, 34, 39, 40, 45, 46, 50, 51, 53, 54, 56, 57, 85, 86, 97, or 98, or a fragment thereof. The fragment encodes at the least the first two amino acid residues of an N-terminal domain sequence encoded by any one of the aforementioned SEQ ID NOs.

In other embodiments, Cpn10 polypeptides of the invention are generated by appending a sequence comprising three or more neutral amino acid residues to the first N-terminal residue of a human wild-type polypeptide sequence. The appended sequence may comprise one or more methionine residue(s). The first amino acid residue of the appended sequence may be a methionine. The polypeptides may possess increased immunomodulatory function compared to Ala-Cpn10 (e.g. compared to human Ala-Cpn10 as set forth in SEQ ID NO: 3) and/or wild-type Cpn10 (e.g. compared to human wild-type Cpn10 as set forth in SEQ ID NO: 1). The polypeptides may possess increased binding affinity to PAMPs and/or DAMPs compared to the binding affinity of wild-type Cpn10 and/or Ala-Cpn10 to those PAMPs and/or DAMPs. The PAMP may comprise CpG motifs. For example, the PAMP may be bacterial DNA.

Cpn10 polypeptides of the invention may comprise the amino acid sequence set forth in any one of SEQ ID NOs: 58, 60, 77, 81, 87, 90, or 93, or a fragment thereof. The fragment comprises at least the first three amino acid residues of an N-terminal domain sequence defined by any one of the aforementioned SEQ ID NOs.

Cpn10 polypeptides of the invention may share at least about 40%, 45%, 50%, 55%, 60%, 65%, 70%, 75%, 80%, 85%, 90%, or 95% sequence identity with a polypeptide comprising the amino acid sequence set forth in any one of SEQ ID NOs: 58, 60, 77, 81, 87, 90, or 93, or a fragment thereof. The fragment comprises at least the first three amino acid residues of an N-terminal domain sequence defined by any one of the aforementioned SEQ ID NOs.

A Cpn10 nucleic acid sequence of the invention may comprise the nucleotide sequence set forth in any one of SEQ ID NOs: 59, 61, 62, 82, 83, 88, 89, 91, 92, 94, or 95, or a fragment thereof. The fragment encodes at the least the first three amino acid residues of an N-terminal domain sequence encoded by any one of the aforementioned SEQ ID NOs.

Cpn10 nucleic acid sequences of the invention may share at least about 40%, 45%, 50%, 55%, 60%, 65%, 70%, 75%, 80%, 85%, 90%, or 95% sequence identity with a nucleic acid comprising the nucleotide sequence set forth in any one of SEQ ID NOs: 59, 61, 62, 82, 83, 88, 89, 91, 92, 94, or 95, or a fragment thereof. The fragment encodes at the least the first three amino acid residues of an N-terminal domain sequence encoded by any one of the aforementioned SEQ ID NOs.

In additional embodiments, Cpn10 polypeptides of the invention are generated by appending a sequence comprising a combination of neutral amino acid residue(s) and positively charged residue(s) to the first N-terminal residue of a human wild-type polypeptide sequence. The first amino acid residue of the appended sequence may be a methionine. The polypeptides may possess increased immunomodulatory function compared to Ala-Cpn10 (e.g. compared to human Ala-Cpn10 as set forth in SEQ ID NO: 3) and/or wild-type Cpn10 (e.g. compared to human wild-type Cpn10 as set forth in SEQ ID NO: 1). The polypeptides may possess increased binding affinity to PAMPs and/or DAMPs compared to the binding affinity of wild-type Cpn10 and/or Ala-Cpn10 to those PAMPs and/or DAMPs. The PAMP may comprise CpG motifs. For example, the PAMP may be bacterial DNA.

Cpn10 polypeptides of the invention may comprise the amino acid sequence set forth in SEQ ID NO: 18, or a fragment thereof. The fragment comprises at least the first two amino acid residues of the N-terminal domain sequence defined by SEQ ID NO: 18.

Cpn10 polypeptides of the invention may share at least about 40%, 45%, 50%, 55%, 60%, 65%, 70%, 75%, 80%, 85%, 90%, or 95% sequence identity with a polypeptide comprising the amino acid sequence set forth in SEQ ID NO: 18, or a fragment thereof. The fragment comprises at least the first two amino acid residues of the N-terminal domain sequence defined by SEQ ID NO: 18.

A Cpn10 nucleic acid sequence of the invention may comprise the nucleotide sequence set forth in SEQ ID NO: 19 or SEQ ID NO: 20. The fragment encodes at the least the first two amino acid residues of an N-terminal domain sequence encoded by SEQ ID NO: 19 or SEQ ID NO: 20.

Cpn10 nucleic acid sequences of the invention may share at least about 40%, 45%, 50%, 55%, 60%, 65%, 70%, 75%, 80%, 85%, 90%, or 95% sequence identity with a nucleic acid comprising the nucleotide sequence set forth in SEQ ID NO: 19 or SEQ ID NO: 20. The fragment encodes at the least the first two amino acid residues of an N-terminal domain sequence encoded by SEQ ID NO: 19 or SEQ ID NO: 20.

In other embodiments, Cpn10 polypeptides of the invention are generated by appending a sequence comprising a combination of neutral amino acid residue(s) and negatively charged residue(s) to the first N-terminal residue of a human wild-type polypeptide sequence. The first amino acid residue of the appended sequence may be a methionine. The polypeptides may possess increased immunomodulatory function compared to Ala-Cpn10 (e.g. compared to human Ala-Cpn10 as set forth in SEQ ID NO: 3) and/or wild-type Cpn10 (e.g. compared to human wild-type Cpn10 as set forth in SEQ ID NO: 1). The polypeptides may possess increased binding affinity to PAMPs and/or DAMPs compared to the binding affinity of wild-type Cpn10 and/or Ala-Cpn10 to those PAMPs and/or DAMPs. The PAMP may comprise CpG motifs. For example, the PAMP may be bacterial DNA.

Cpn10 polypeptides of the invention may comprise the amino acid sequence set forth in SEQ ID NO: 41 or SEQ ID NO: 47, or a fragment thereof. The fragment comprises at least the first two amino acid residues of the N-terminal domain sequence defined by SEQ ID NO: 41 or SEQ ID NO: 47.

Cpn10 polypeptides of the invention may share at least about 40%, 45%, 50%, 55%, 60%, 65%, 70%, 75%, 80%, 85%, 90%, or 95% sequence identity with a polypeptide comprising the amino acid sequence set forth in SEQ ID NO: 41 or SEQ ID NO: 47, or a fragment thereof. The fragment comprises at least the first two amino acid residues of the N-terminal domain sequence defined by SEQ ID NO: 41 or SEQ ID NO: 47.

A Cpn10 nucleic acid sequence of the invention may comprise the nucleotide sequence set forth in any one of SEQ ID NOs: 42, 43 or 48. The fragment encodes at the least the first two amino acid residues of an N-terminal domain sequence encoded by any one of SEQ ID NOs: 42, 43 or 48.

Cpn10 nucleic acid sequences of the invention may share at least about 40%, 45%, 50%, 55%, 60%, 65%, 70%, 75%, 80%, 85%, 90%, or 95% sequence identity with a nucleic acid comprising the nucleotide sequence set forth in any one of SEQ ID NOs: 42, 43 or 48. The fragment encodes at the least the first two amino acid residues of an N-terminal domain sequence encoded by any one of SEQ ID NOs: 42, 43 or 48.

Cpn10 polypeptides of the invention may comprise further additional amino acid residue substitution(s), deletion(s) and/or insertion(s) (in comparison to a wild-type Cpn10 polypeptide sequence) in region(s) located outside of the N-terminal domain.

For example, Cpn10 polypeptides of the invention may additionally comprise one or more amino acid insertion(s), deletion(s) or substitution(s) in the roof β-hairpin domain, β-barrel domain and/or mobile loop domain. Accordingly, by way of example only, Cpn10 polypeptides of the invention may further comprise additional substitution(s), deletion(s)

and/or insertion(s) in any one or more of positions 7-101 of the amino acid sequence set forth in SEQ ID NO: 1.

In certain embodiments, Cpn10 polypeptides of the invention differ from a human wild-type Cpn10 polypeptide sequence (or a variant or fragment thereof) by the substitution, deletion and/or insertion of one or more amino acid residue(s) in the N-terminal domain and one or more amino acid insertion(s), deletion(s) or substitution(s) in the roof β-hairpin domain (defined by residues 52-62 of SEQ ID NO: 1).

The percentage of sequence identity between two sequences may be determined by comparing two optimally aligned sequences over a comparison window. A portion of a sequence (e.g. a Cpn10 polypeptide or Cpn10 nucleic acid of the invention) in the comparison window may, for example, comprise deletions or additions (i.e. gaps) in comparison to a reference sequence (e.g. one derived from another species) which does not comprise deletions or additions, in order to align the two sequences optimally, or vice versa. A percentage of sequence identity may then be calculated by determining the number of positions at which identical amino acid residues (or nucleotides) occur in both sequences to yield the number of matched positions, dividing the number of matched positions by the total number of positions in the window of comparison and multiplying the result by 100 to yield the percentage of sequence identity.

In the context of two or more nucleic acid or polypeptide sequences, the percentage of sequence identity refers to the specified percentage of amino acid residues or nucleotides that are the same over a specified region (or, when not specified, over the entire sequence) when compared and aligned for maximum correspondence over a comparison window, or designated region as measured using one of the following sequence comparison algorithms or by manual alignment and visual inspection.

For sequence comparison, typically one sequence acts as a reference sequence to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percentage of sequence identity for the test sequence(s) relative to the reference sequence, based on the program parameters.

Methods of alignment of sequences for comparison are known in the art. Optimal alignment of sequences for determination of sequence identity can be achieved conventionally using known computer programs, including, but not limited to, CLUSTAL in the PC/Gene program (available from Intelligenetics, Mountain View, Calif.), the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA).

A Cpn10 polypeptide of the invention as exemplified herein may further include one or more additional amino acids. In some embodiments, the additional amino acids may correspond to amino acids immediately upstream and/or downstream of a protein or larger polypeptide from which the exemplified polypeptide may be derived. The skilled addressee will recognise that one or more amino acids of a Cpn10 polypeptide of the invention as exemplified herein may be deleted without loss of activity.

Cpn10 polypeptides of the invention may be modified with an acetyl group, lipids, carbohydrates and/or phosphate groups, for example, to improve immunogenicity, stability and/or solubility. Capping of polypeptide termini may be used to enhance stability against cellular proteases.

A Cpn10 nucleic acid of the invention as exemplified herein may further include one or more additional nucleotides. In some embodiments, the additional nucleotides may correspond to nucleotides immediately upstream and/or downstream in a genomic sequence from which the nucleic acid is derived. The skilled addressee will recognise that one or more nucleotides of a Cpn10 nucleic acid of the invention as exemplified herein may be deleted without loss of activity.

It will be understood that "Cpn10 polypeptide(s) of the invention" encompass variants of those polypeptides. Similarly, it will be understood that "Cpn10 nucleic acid(s) of the invention" encompass variants of those nucleic acids.

The term "variant" as used herein refers to a substantially similar sequence. In general, two sequences are "substantially similar" if the two sequences have a specified percentage of amino acid residues or nucleotides that are the same (percentage of "sequence identity"), over a specified region, or, when not specified, over the entire sequence. Accordingly, a "variant" of a Cpn10 nucleic acid of the invention or a Cpn10 polypeptide of the invention may share at least about 40%, 45%, 50%, 55%, 60%, 65%, 70%, 75%, 80%, 83% 85%, 88%, 90%, 93%, 95%, 96%, 97%, 98% or 99% sequence identity with the reference sequence.

In general, polypeptide variants possess qualitative biological activity in common with the polypeptide from which they are derived. Nucleic acid variants generally encode polypeptides which generally possess qualitative biological activity in common with the polypeptide from which they are derived. Also included within the meaning of the term "variant" are homologues of Cpn10 nucleic acids of the invention and Cpn10 polypeptides of the invention. A nucleic acid homologue is typically from a different species but sharing substantially the same biological function or activity as the corresponding Cpn10 nucleic acid of the invention. A polypeptide homologue is typically from a different species but sharing substantially the same biological function or activity as the corresponding Cpn10 polypeptide of the invention.

Further, the term "variant" also includes analogues of the Cpn10 polypeptides of the invention. A polypeptide "analogue" is a polypeptide which is a derivative of a Cpn10 polypeptide of the invention, which derivative comprises addition, deletion, substitution of one or more amino acids, such that the polypeptide retains substantially the same function. The term "conservative amino acid substitution" refers to a substitution or replacement of one amino acid for another amino acid with similar properties within a polypeptide chain (primary sequence of a protein). For example, the substitution of the charged amino acid glutamic acid (Glu) for the similarly charged amino acid aspartic acid (Asp) would be a conservative amino acid substitution.

It will be understood that "Cpn10 polypeptide(s) of the invention" encompass fragments of those polypeptides. Similarly, it will be understood that "Cpn10 nucleic acid(s) of the invention" encompass fragments of those nucleic acids.

A "fragment" of a Cpn10 polypeptide of the invention is a polypeptide that encodes a constituent or is a constituent of a Cpn10 polypeptide of the invention or variant thereof. Typically the fragment possesses qualitative biological activity in common with the polypeptide of which it is a constituent. Typically, the polypeptide fragment may be at least about 5, 10, 15, 20, 25, 30, 35, 40, 45, 50, 55, 60, 65, 70, 75, 80, 85, 90, 95, 100 or greater than 100 amino acid residues in length.

A "fragment" of a Cpn10 nucleic acid of the invention is a nucleic acid that encodes a constituent or is a constituent of a Cpn10 nucleic acid of the invention or variant thereof. Fragments of a nucleic acid do not necessarily need to encode polypeptides which retain biological activity. The fragment may, for example, be useful as a hybridisation probe or PCR primer. Typically, the nucleic acid fragment may be at least about 5, 10, 15, 20, 25, 30, 35, 40, 45, 50, 60, 70, 80, 90, 100, 125, 150, 175, 200, 225, 250, 275, 300, 325, 350, 375, 425, 450, 475, 500, 550, 600, 650, 700, 750, 800, 850, 900, 950, 1000, 1100, 1200, 1300, 1400, 1500, 1750, 2000, 2250, 2500, 2750, 3000, 3250 or 3400 nucleotides in length.

In general, Cpn10 polypeptides of the invention possess increased binding affinity for molecules comprising pathogen-associated molecular patterns (PAMPs) and/or host molecules comprising damage-associated molecular patterns (DAMPs), compared to wild-type Cpn10 and/or Ala-Cpn10. Hence, binding interactions between Cpn10 polypeptides of the invention and molecules comprising PAMPs or DAMPs are generally stronger than binding interactions between wild-type Cpn10 and those same molecules. Preferably, binding interactions between the Cpn10 polypeptides of the invention and molecules comprising PAMPs or DAMPs are stronger than binding interactions between Ala-Cpn10 and those same molecules.

The binding of molecules comprising PAMPs or DAMPs may influence the nature and/or strength of immune response/s. By virtue of binding molecules comprising PAMPs or DAMPs more strongly than wild-type Cpn10 and/or Ala-Cpn10 bind to those same molecules, Cpn10 polypeptides of the invention may exert increased immunomodulatory function in comparison to wild-type Cpn10 and/or Ala-Cpn10.

Accordingly, in certain embodiments Cpn10 polypeptides of the invention may possess increased immunomodulatory function compared to Ala-Cpn10 (e.g. compared to human Ala-Cpn10 as set forth in SEQ ID NO: 3).

The N-terminus of the polypeptides may be extended by at least one, two, or three additional amino acid residues compared to a wild-type polypeptide. The N-terminus may commence with a methionine residue.

Cpn10 polypeptides of the invention possessing increased immunomodulatory function compared to Ala-Cpn10 may comprise, for example, the amino acid sequence set forth in any one of SEQ ID NOs: 9, 12, 15, 18, 21, 24, 26, 29, 32, 35, 38, 41, 44, 52, 55, 58, 60, 81, 84, 87, 90 or 93, or a fragment thereof that comprises the N-terminal domain of that sequence.

Cpn10 polypeptides of the invention possessing increased immunomodulatory function compared to Ala-Cpn10 may share at least about 40%, 45%, 50%, 55%, 60%, 65%, 70%, 75%, 80%, 85%, 90%, or 95% sequence identity with a polypeptide comprising the amino acid sequence set forth in any one of SEQ ID NOs: 9, 12, 15, 18, 21, 24, 26, 29, 32, 35, 38, 41, 44, 52, 55, 58, 60, 81, 84, 87, 90 or 93, or a fragment thereof that comprises the N-terminal domain of that sequence.

The level of immunomodulatory function (i.e. immunomodulatory capacity) of a Cpn10 polypeptide of the invention can be measured using any suitable method known in the art. For example, the level of immunomodulatory function can be measured by the propensity and/or strength of binding interactions of the polypeptides with PAMPs and DAMPs (e.g. bacterial CpGs) which can in turn be measured using methods described in the Examples of the present specification. Additionally or alternatively, the immunomodulatory function of Cpn10 polypeptides of the invention can be assessed by measuring the degree of pattern recognition receptor (PRR) signalling elicited by the polypeptides. For example, the capacity of the polypeptides to inhibit poly(I:C)-induced NFκB production through PRRs (e.g. Toll like receptors) can be measured using techniques described in U.S. patent application Ser. No. 12/934,980 (published on 30 Dec. 2009), the entire contents of which are incorporated herein by cross-reference. Additionally or alternatively, the immunomodulatory function of Cpn10 polypeptides of the invention can be assessed by measuring the level of cytokine production and/or cytokine secretion by cells expressing PRRs in the presence of the polypeptides and ligand/s for those PRRs (see also section below entitled "Immunosuppression"). The skilled addressee will recognise that the above-mentioned techniques are exemplary, and that no particular restriction exists regarding particular method/s used to measure the level of immunomodulatory function (i.e. immunomodulatory capacity) of a Cpn10 polypeptide of the invention.

In certain embodiments, Cpn10 polypeptides of the invention may possess increased binding affinity to PAMPs and/or DAMPs compared to the binding affinity of wild-type Cpn10 and/or Ala-Cpn10 to those PAMPs and/or DAMPs.

The PAMP may comprise CpG motifs. For example, the PAMP may be bacterial DNA. The PAMP may be an oligonucleotide comprising a CpG oligodeoxynucleotide motif (CpG ODN). In certain embodiments, the CpG ODN motif is any one or more of CpGA, CpGB and CpGC.

Certain Cpn10 N-terminal variants may, in some embodiments, be excluded from the scope of the present invention. For example, in certain embodiments the specific human Cpn10 N-terminal variants Ala-Cpn10 (SEQ ID NO: 3), GSM-Cpn10 (SEQ ID NO: 57), and Gly-Cpn10 (SEQ ID NO: 6) may be excluded from the scope of the present invention.

Cpn10 polypeptides of the invention may be manufactured using methods known in the art. For example, Cpn10 polypeptides of the invention may be manufactured by conventional methods used in peptide chemistry synthesis such as solid phase peptide synthesis, liquid phase peptide synthesis and recombinant gene technology. It will be understood that amino acid residues of Cpn10 polypeptides of the invention include any and all of their isomers (e.g. D-form, L-form and DL-form) and isoforms.

A Cpn10 polypeptide of the invention may be synthesised by solid phase chemistry techniques (see, for example, Steward et al., (1963), in "Solid Phase Peptide Synthesis", H. Freeman Co., San Francisco; Meienhofer, (1973), in "Hormonal Proteins and Peptides", volume 2, 46) or by classical solution synthesis (see, for example, Schroder et al., (1965), in "The Peptides", volume 1, 72-75, Academic Press (New York). In general, such methods comprise the addition of one or more amino acids or suitably protected amino acids to a growing sequential polypeptide chain on a polymer. Typically, either the amino or carboxyl group of the first amino acid is protected by a suitable protecting group. The protected and/or derivatised amino acid is then either attached to an inert solid support or utilized in solution by adding the next amino acid in the sequence having the complimentary (amino or carboxyl) group suitably protected and under conditions suitable for forming the amide linkage. The protecting group may then be removed from the newly added amino acid residue and the next amino acid (suitably protected) is then added to form a growing polypeptide chain.

A Cpn10 polypeptide of the invention may be produced, for example, by digestion of a protein or larger polypeptide with one or more proteinases such as endoLys-C, endoArg-C, endoGlu-C and *Staphylococcus* V8-protease. The digested peptide fragments can be purified by, for example, high performance liquid chromatographic (HPLC) techniques.

Additionally or alternatively, a Cpn10 polypeptide of the invention may be produced using recombinant polypeptide production techniques. Recombinant polypeptide production techniques will typically involve the cloning of a nucleic acid encoding a Cpn10 polypeptide of the invention into a plasmid for subsequent overexpression in a suitable microorganism. Suitable methods for the construction of expression vectors or plasmids are described in detail, for example, in standard texts such as Sambrook et al., (1989), "*Molecular Cloning: A Laboratory Manual*", (2nd ed., Cold Spring Harbor Laboratory Press, Plainview, N.Y.; and, Ausubel et al., (Eds), (2007), "*Current Protocols in Molecular Biology*", John Wiley and Sons, Inc.

Recombinant methods suitable for producing Cpn10 polypeptides of the invention are described in detail, for example, in standard texts such as Coligan et al., (Eds) (2007), "*Current Protocols in Protein Science*", (Chapter 5), John Wiley and Sons, Inc.; and Pharmacia Biotech., (1994), "*The Recombinant Protein Handbook*", Pharmacia Biotech.

Commonly used expression systems that may be used for the production of Cpn10 polypeptides of the invention include, for example, bacterial (e.g. *E. coli*), yeast (e.g. *Saccharomyces cerevisiae, Aspergillus, Pichia pastorisis*), viral (e.g. baculovirus and vaccinia), cellular (e.g. mammalian and insect) and cell-free systems. Suitable cell-free systems that may be used include, but are not limited to, eukaryotic rabbit reticuloctye, wheat germ extract systems, and the prokaryotic *E. coli* cell-free system (see, for example, Madin et al., *Proc. Natl. Acad. Sci. U.S.A.* 97:559-564 (2000), Pelham and Jackson, *Eur. J. Biochem.*, 67: 247-256 (1976); Roberts and Paterson, *Proc. Natl. Acad. Sci.*, 70: 2330-2334 (1973); Zubay, *Ann. Rev. Genet.*, 7: 267 (1973); Gold and Schweiger, *Meth. Enzymol.*, 20: 537 (1971); Lesley et al., *J. Biol. Chem.*, 266 (4): 2632-2638 (1991); Baranov et al., *Gene*, 84: 463-466 (1989); and Kudlicki et al., *Analyt. Biochem.*, 206: 389-393 (1992).

Changes to the amino acid sequence of a Cpn10 polypeptide of the invention (e.g. to produce a polypeptide having a specified percentage of sequence identity with a Cpn10 polypeptide of the invention) may be achieved using standard techniques in the art. For example, amino acid changes may be achieved by using nucleotide replacement techniques which include the addition, deletion or substitution of nucleotides (conservative and/or non-conservative), under the proviso that the proper reading frame is maintained. Exemplary techniques include random mutagenesis, site-directed mutagenesis, oligonucleotide-mediated or polynucleotide-mediated mutagenesis, deletion of selected region(s) through the use of existing or engineered restriction enzyme sites, and the polymerase chain reaction. Testing the activity of modified polypeptides for the purposes of the invention may be via any one of a number of techniques known to those of skill in the art.

Purification of Cpn10 polypeptides of the invention may be achieved using standard techniques in the art such as those described in Coligan et al., (2007), "*Current Protocols in Protein Science*", (Chapter 6), John Wiley and Sons, Inc. For example, if the polypeptide is in a soluble state it may be isolated using standard methods such as column chromatography. Cpn10 polypeptides of the invention may be genetically engineered to contain various affinity tags or carrier proteins that aid purification. For example, the use of histidine and protein tags engineered into an expression vector containing a nucleic acid encoding a polypeptide of the invention may facilitate purification by, for example, metal-chelate affinity chromatography (MCAC) under either native or denaturing conditions. Purification may be scaled-up for large-scale production purposes.

Cpn10 nucleic acids of the invention may be manufactured using standard techniques known in the art such as those described, for example, in Sambrook et al., (1989) "*Molecular Cloning: A Laboratory Manual*", (2nd ed., Cold Spring Harbor Laboratory Press, Plainview, N.Y.; Itakura K. et al., (1984), "*Synthesis and use of synthetic oligonucleotides*", Annu. Rev. Biochem. 53:323; Innis et al., (Eds), (1990), "*PCR Protocols: A Guide to Methods and Applications*", Academic Press, New York; Innis and Gelfand, (Eds), (1995), "*PCR Strategies*", Academic Press, New York; and Innis and Gelfand, (Eds), (1999), "*PCR Methods Manual*", Academic Press, New York.

Cpn10 nucleic acids of the invention can be manufactured, for example, by chemical synthesis techniques including the phosphodiester and phosphotriester methods (see, for example, Narang et al., (1979), "*Improved phosphotriester method for the synthesis of gene fragments*", Meth. Enzymol. 68:90; Brown et al., (1979), "*Chemical Synthesis and Cloning of a Tyrosine tRNA Gene*", Meth. Enzymol. 68:109-151; and U.S. Pat. No. 4,356,270) or the diethylphosphoramidite method (see Beaucage and Caruthers, (1981), "*Deoxynucleotide phosphoramidite*", Tetrahedron Letters, 22:1859-1862). A method for synthesising oligonucleotides on a modified solid support is described in U.S. Pat. No. 4,458,066.

Cpn10 nucleic acids of the invention may be deoxyribonucleic acids (DNA), ribonucleic acids (RNA) or complementary deoxyribonucleic acids (cDNA). RNA may be derived from RNA polymerase-catalyzed transcription of a DNA sequence. The RNA may be a primary transcript derived from transcription of a corresponding DNA sequence. RNA may also undergo post-transcriptional processing. For example, a primary RNA transcript may undergo post-transcriptional processing to form a mature RNA. Messenger RNA (mRNA) refers to RNA derived from a corresponding open reading frame that may be translated into a protein by the cell. cDNA refers to a double-stranded DNA that is complementary to and derived from mRNA. Sense RNA refers to RNA transcript that includes the mRNA and so can be translated into a protein by the cell. Anti-sense RNA refers to an RNA transcript that is complementary to all or part of a target primary transcript or mRNA and may be used to block the expression of a target gene.

Those skilled in the art will recognise that RNA and cDNA sequences encoded by a given Cpn10 DNA sequence may be derived using the genetic code. An RNA sequence may be derived from a given DNA sequence by generating a sequence that is complementary to the particular DNA sequence. The complementary sequence may be generated by converting each cytosine ('C') base in the DNA sequence to a guanine ('G') base, each guanine ('G') base in the DNA sequence to a cytosine ('C') base, each thymidine ('T') base in the DNA sequence to an adenine ('A') base, and each adenine ('A') base in the DNA sequence to a uracil ('U') base.

A complementary DNA (cDNA) sequence may be derived from a DNA sequence by deriving an RNA sequence from the DNA sequence as above, then converting the RNA sequence into a cDNA sequence. An RNA sequence can be converted into a cDNA sequence by converting each cytosine ('C') base in the RNA sequence to a guanine ('G') base, each guanine ('G') base in the RNA sequence to a cytosine ('C') base, each uracil ('U') base in the RNA sequence to an adenine ('A') base, and each adenine ('A') base in the RNA sequence to a thymidine ('T') base.

In certain embodiments, Cpn10 nucleic acids of the invention may be cloned into a vector. The vector may comprise, for example, a DNA, RNA or complementary DNA (cDNA) sequence. The vector may be a plasmid vector, a viral vector, or any other suitable vehicle adapted for the insertion of foreign sequences, their introduction into cells and the expression of the introduced sequences. Typically the vector is an expression vector and may include expression control and processing sequences such as a promoter, an enhancer, ribosome binding sites, polyadenylation signals and transcription termination sequences.

The invention also contemplates host cells transformed by such vectors. For example, Cpn10 nucleic acids of the invention may be cloned into a vector which is transformed into a bacterial host cell such as, for example, *E. coli*. Methods for the construction of vectors and their transformation into host cells are generally known in the art, and described in, for example, Sambrook et al., (1989), "*Molecular Cloning: A Laboratory Manual*", Cold Spring Harbor Laboratory Press, Plainview, N.Y.; and, Ausubel et al., (Eds) (2007), "*Current Protocols in Molecular Biology*", John Wiley and Sons, Inc.

Antibodies

The invention also provides antibodies ("antibody(s) of the invention") that "bind specifically" to Cpn10 polypeptides of the invention.

An antibody that "binds specifically" to a Cpn10 polypeptide of the invention is one capable of binding to the polypeptide with a significantly higher affinity than it binds to an unrelated molecule (e.g. a non-target polypeptide). Accordingly, an antibody that binds specifically to a Cpn10 polypeptide of the invention is an antibody with the capacity to discriminate between that polypeptide and any other number of potential alternative binding partners. Hence, when exposed to a plurality of different but equally accessible molecules as potential binding partners, an antibody specific for a Cpn10 polypeptide of the invention will selectively bind to that polypeptide and other alternative potential binding partners will remain substantially unbound by the antibody. In general, an antibody specific for a Cpn10 polypeptide of the invention will preferentially bind to that polypeptide at least 10-fold, preferably 50-fold, more preferably 100-fold, and most preferably greater than 100-fold more frequently than other potential binding partners that are not target polypeptides. An antibody specific for a Cpn10 polypeptide of the invention may be capable of binding to other non-target molecules at a weak, yet detectable level. This is commonly known as background binding and is readily discernible from polypeptide-specific binding, for example, by use of an appropriate control.

Reaction conditions (e.g. concentration of antibody, incubation time, pH, temperature etc) to facilitate binding of antibodies to Cpn10 polypeptides of the invention will depend primarily on the antibody utilised and the specific target polypeptide, and may be readily determined using methods known in the art (see, for example, Ausubel et al., (1994), "*Current Protocols in Molecular Biology*", Vol. 1, John Wiley & Sons, Inc., New York; Coligan et al., (Eds), (2008), "*Current protocols in Immunology*", John Wiley and Sons, Inc.; and Bonifacino et al., (Eds) (2007), "*Current protocols in Cell Biology*", John Wiley and Sons, Inc.).

An antibody that binds specifically to a Cpn10 polypeptide of the invention can be generated using methods known in the art.

For example, a monoclonal antibody specific for a Cpn10 polypeptide of the invention, typically containing Fab portions, may be prepared using the hybridoma technology described in Harlow and Lane (eds.), (1988), "*Antibodies—A Laboratory Manual*", Cold Spring Harbor Laboratory, N.Y.

In essence, in the preparation of monoclonal antibodies directed toward a Cpn10 polypeptide of the invention, any technique that provides for the production of antibodies by continuous cell lines in culture may be used. These include the hybridoma technique originally developed by Kohler and colleagues (see Kohler et al., (1975), "*Continuous cultures of fused cells secreting antibody of predefined specificity*", Nature, 256:495-497) as well as the trioma technique, the human B-cell hybridoma technique (see Kozbor et al., (1983), "*The Production of Monoclonal Antibodies From Human Lymphocytes*", Immunology Today, 4:72-79), and the EBV-hybridoma technique to produce human monoclonal antibodies (see Cole et al., (1985), in "*Monoclonal Antibodies and Cancer Therapy*", 77-96, Alan R. Liss, Inc.). Immortal, antibody-producing cell lines can be created by techniques other than fusion, such as direct transformation of B lymphocytes with oncogenic DNA, or transfection with Epstein-Barr virus (see, for example, Schreier et al., (1980), "*Hybridoma Techniques*", Cold Spring Harbor Laboratory; Hammerling et al., (1981), "*Monoclonal Antibodies and T-cell Hybridomas*", Elsevier/North-Holland Biochemical Press, Amsterdam; and Kennett et al., (1980), "*Monoclonal Antibodies*", Plenum Press).

In summary, generating a hybridoma from which the monoclonal antibody is produced typically involves fusing a myeloma or other self-perpetuating cell line with lymphocytes obtained from the spleen of a mammal hyperimmunised with a recognition factor-binding portion thereof, or recognition factor, or an origin-specific DNA-binding portion thereof. Hybridomas producing a monoclonal antibody specific for a polypeptide of the invention are identified by their ability to immunoreact with the antigens present in that polypeptide.

A monoclonal antibody that binds specifically to a Cpn10 polypeptide of the invention can be produced by initiating a monoclonal hybridoma culture comprising a nutrient medium containing a hybridoma that secretes antibodies of the appropriate antigen specificity. The culture is maintained under conditions and for a time period sufficient for the hybridoma to secrete the antibody molecules into the medium. The antibody-containing medium is then collected. The antibody molecules can then be further isolated using known techniques.

Similarly, there are various procedures known in the art which may be used for the production of polyclonal antibodies. For the production of polyclonal antibodies against a Cpn10 polypeptide of the invention, various host animals can be immunised by injection with the polypeptide, including, but not limited to, rabbits, chickens, mice, rats, sheep, goats and the like. Further, the polypeptide can be conjugated to an immunogenic carrier (e.g. bovine serum albumin (BSA) or keyhole limpet hemocyanin (KLH)). Also, various adjuvants may be used to increase the immunological response, including, but not limited to, Freund's (complete and incomplete), mineral gels such as aluminium hydroxide, surface active substances such as rysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

Screening for the desired antibody can also be accomplished by a variety of techniques known in the art. Suitable assays for immunospecific binding of antibodies include, but are not limited to, radioimmunoassays, ELISAs (enzyme-linked immunosorbent assay), sandwich immunoassays, immunoradiometric assays, gel diffusion precipitation reactions, immunodiffusion assays, in situ immunoassays, Western blots, precipitation reactions, agglutination assays, complement fixation assays, immunofluorescence assays, protein A assays, immunoelectrophoresis assays, and the like (see, for example, Ausubel et al., (1994), "*Current Protocols in Molecular Biology*", Vol. 1, John Wiley & Sons, Inc., New York). Antibody binding may be detected by virtue of a detectable label on the primary antibody. Alternatively, the antibody may be detected by virtue of its binding with a secondary antibody or reagent which is appropriately labelled. A variety of methods for detecting binding events in an immunoassay are known in the art, and are included in the scope of the invention.

In terms of obtaining a suitable amount of an antibody of the invention, one may manufacture the antibodies using batch fermentation with serum free medium. After fermentation the antibody may be purified via a multistep procedure incorporating chromatography and viral inactivation/removal steps. For instance, the antibody may be first separated by Protein A affinity chromatography and then treated with solvent/detergent to inactivate any lipid enveloped viruses. Further purification, typically by anion and cation exchange chromatography, may be used to remove residual proteins, solvents/detergents and nucleic acids. The purified antibody may be further purified and formulated into 0.9% saline using gel filtration columns. The formulated bulk preparation may then be sterilised and viral filtered and dispensed.

Immunosuppression

The invention provides methods for suppressing immune activation in a subject. In certain embodiments, the methods comprise administering a Cpn10 polypeptide of the invention (or a composition comprising the same) to the subject. In other embodiments, the methods comprise administering a Cpn10 nucleic acid of the invention (or a composition comprising the same) to the subject. Also provided is use of a Cpn10 polypeptide of the invention or a Cpn10 nucleic acid of the invention in the preparation of a medicament for suppressing immune activation in a subject.

Cpn10 polypeptides of the invention and Cpn10 nucleic acids of the invention may be administered to the subject (e.g. a human subject) by any suitable route including, but not limited to, the parenteral (e.g. intravenous, intradermal, subcutaneous or intramuscular), mucosal (e.g. oral or intranasal) or topical route.

Without limitation to a particular mechanism or mode of action, it is believed that modification(s) to residue(s) in the N-terminal domain of wild-type Cpn10 polypeptides confers increased binding affinity to molecules comprising pathogen-associated molecular patterns (PAMPs) and/or host molecules comprising damage-associated molecular patterns (DAMPs), compared to wild-type Cpn10. Hence, binding interactions between Cpn10 polypeptides of the invention and molecules comprising PAMPs or DAMPs are generally stronger than binding interactions between wild-type Cpn10 and those same molecules. Preferably, binding interactions between Cpn10 polypeptides of the invention and molecules comprising PAMPs or DAMPs are stronger than binding interactions between Ala-Cpn10 and those same molecules. The binding of ligands comprising PAMPs or DAMPs to pattern recognition receptors (PRRs) initiates a series of events central to establishing effective innate immune responses. It is postulated that tight binding of these ligands by Cpn10 polypeptides of the invention modifies or prevents the interaction between those ligands and their target PRRs. This in turn is believed to inhibit the initiation of immune activation induced by PRR signalling (e.g. production and secretion of inflammatory molecules).

A Cpn10 polypeptide of the invention may bind to a PAMP derived from any microorganism. Non limiting examples of such microorganisms include bacteria, viruses, fungi, nematodes, mycobacteria and protozoa.

Preferably, Cpn10 polypeptides of the invention bind with high affinity to nucleic acid based PAMPs.

Non limiting examples of nucleic acid based PAMPs to which Cpn10 polypeptides of the invention may bind include bacterial DNA containing unmethylated cytosine phosphate guanine (CgG) motifs and PAMPs derived from viruses including double stranded RNA, 5' triphosphate ssRNA and other replication intermediates.

In preferred embodiments, Cpn10 polypeptides of the invention bind with high affinity to oligonucleotides containing CpG motifs (CpG ODNs).

In general, Cpn10 polypeptides of the invention bind to CpG ODNs with a higher affinity than wild-type Cpn10 binds to CpG ODNs. Preferably, Cpn10 polypeptides of the invention bind to CpG ODNs with a higher affinity than Ala-Cpn10 binds to CpG ODNs.

In certain embodiments, Cpn10 polypeptides of the invention bind to a host molecule (e.g. a host protein, nucleic acid or lipid) sharing structural, conformational and/or sequence homology with one or more PAMPs derived from a microorganism.

Accordingly, Cpn10 polypeptides of the invention bind may bind to DAMPs.

Preferably, Cpn10 polypeptides of the invention bind with high affinity to nucleic acid based DAMPs, non-limiting examples of which include cellular DNA and RNA and immune complexes. Additionally or alternatively, Cpn10 polypeptides of the invention bind with high affinity to nucleotide and/or nucleoside DAMPs.

In preferred embodiments, Cpn10 polypeptides of the invention bind with high affinity to DNA DAMPs.

In general, Cpn10 polypeptides of the invention bind to DNA DAMPs with a higher affinity than wild-type Cpn10 binds to DNA DAMPs. Preferably, Cpn10 polypeptides of the invention bind to DNA DAMPs with a higher affinity than Ala-Cpn10 binds to DNA DAMPs.

A PAMP or DAMP bound by a Cpn10 polypeptide of the invention will, in general, be a ligand for a pattern recognition receptor (PRR). Non-limiting examples of PRRs bound by such ligands include toll-like receptors (TLRs), retinoic acid-inducible gene I-like receptors (RLRs), nucleotide-binding oligomerization domain-like receptors (NLRs), and DNA-dependent activator of IFN-regulatory factors (DAI).

The PRR may be expressed on one or more immune cell types, non-limiting examples of which include macrophages, monocytes, B lymphocytes, mast cells, natural killer cells and dendritic cells (e.g. myeloid dendritic cells, plasmacytoid dendritic cells).

In certain embodiments, a PAMP or DAMP bound by a Cpn10 polypeptide of the invention is a ligand for an RLR receptor, non-limiting examples of which include RIG-1 and MDA5.

In other embodiments, a PAMP or DAMP bound by a Cpn10 polypeptide of the invention is a ligand for an NLR, non-limiting examples of which include NALP3-Inflammasome and AIM2-Inflammasome.

In further embodiments, a PAMP or DAMP bound by a Cpn10 polypeptide of the invention is a ligand for a toll-like receptor. The toll-like receptor may be selected from the group consisting of TLR3, TLR7, TLR8, or TLR9. In one embodiment, the TLR receptor is TLR9.

In accordance with the methods provided herein, Cpn10 polypeptides of the invention and Cpn10 nucleic acids of the invention are administered to suppress immune activation in a subject.

The subject may be an individual of any mammalian species including, but not limited to, members of the genus ovine (e.g. sheep), bovine, equine, porcine, feline, canine, primates (e.g. humans), and rodents. Preferably, the subject is a human.

In certain embodiments, the methods further comprise administering an immunosuppressive agent to the subject. Non-limiting examples of immunosuppressive agents include anti-inflammatory compounds, bronchodilatory compounds, cyclosporines, tacrolimus, sirolimus, mycophenolate mofetil, methotrexate, chromoglycalates, theophylline, leukotriene antagonist, and antihistamine, and combinations thereof. The immunosuppressive agent may also be an immunosuppressive drug or a specific antibody directed against B or T lymphocytes, or surface receptors that mediate their activation. For example, the immunosuppressive drug may be cyclosporine, tacrolimus, sirolimus, mycophenolate mofetil, methotrexate, chromoglycalates, theophylline, leukotriene antagonist, and antihistamine, or a combination thereof.

As discussed above, it is believed that binding of Cpn10 polypeptides of the invention to PAMPs and DAMPs (i.e. ligands) of PRRs alters the interaction between the ligand and receptor.

Accordingly, binding of a Cpn10 polypeptide of the invention to a ligand that is an agonist of a PRR may reduce the capacity of the agonist to bind the PRR and thus hinder the initiation of cellular signalling cascades responsible for immune activation.

Cellular signalling cascades initiated by the binding of ligands to cellular PRRs on phagocytic cells (e.g. macrophages) may induce endocytosis and destruction of pathogens.

Cellular signalling cascades initiated by the binding of ligands to cellular PRRs may induce the production and secretion of inflammatory mediators or anti-inflammatory mediators (e.g. cytokines and chemokines). These mediators in turn regulate the activation and function of various immune cells.

In general, Cpn10 polypeptides of the invention (and/or Cpn10 nucleic acids of the invention encoding the same) suppress immune activation in a subject to which they are administered.

The capacity of Cpn10 polypeptides of the invention (and/or Cpn10 nucleic acids of the invention encoding the same) to suppress immune activation in a given subject can be determined using standard techniques known in the art.

For example, immune cells derived from the subject that express PRRs can be exposed to the Cpn10 polypeptide in combination with a given PRR ligand ex vivo and the production and/or secretion of inflammatory mediators (e.g. cytokines and chemokines) then measured using standard assays (e.g. ELISAs). The inflammatory mediator may be a pro-inflammatory cytokine or chemokine (e.g. TNFα, IL-1, IL4, IL6, IL8, IL-12, IL-17, IL-23, IFNα, IFNβ, IFNγ, RANTES etc), a chemical mediator (e.g. leukotrienes, histamine, serotonin, prostaglandins, CGRP, nitric oxide, bradykinin, lysosomal enzymes, thromboxanes, platelet activating factors (PAFs), reactive oxygen species, nitric oxide), a neuropeptide, growth factor or neurotransmitters. The inflammatory mediator may be an anti-inflammatory cytokine (e.g. IL4, IL-10, TGFβ).

Additionally or alternatively, the expression of cell surface receptors for inflammatory mediators and/or cell surface markers of activation may be determined ex vivo (e.g. by flow cytometry) after exposure of immune cells to a Cpn10 polypeptide of the invention in combination with a given PRR ligand.

The degree of cellular activation may also be measured by detecting cellular signals (e.g. TLR-mediated NF-κB activation, type-1 interferon production, tyrosine or serine/threonine phosphorylation, ADP ribosylation etc.) or activation of complement, using standard assays known in the art.

The skilled addressee will understand that the methods for detecting immune activation referred to above are provided for the purpose of exemplification only and that other suitable means known in the art are within the scope of the invention.

Methods of Treatment

The invention provides methods for the treatment and/or prevention of diseases and conditions associated with immune activation, and in particular, excessive and/or chronic inflammation. The methods comprise administering a Cpn10 polypeptide of the invention and/or a Cpn10 nucleic acid of the invention. The polypeptide and/or nucleic acid may be administered in the form of a composition (e.g. a pharmaceutical composition comprising an appropriate carrier, diluent and/or carrier).

Without limitation to a particular mechanism or mode of action, administration of Cpn10 polypeptides of the invention and/or Cpn10 nucleic acids of the invention (or compositions comprising the same) is believed to provide a means of inhibiting PRR-mediated signalling and hence may be used to suppress the production/secretion of inflammatory mediators in a subject. Many diseases and conditions are associated with chronic inflammation of the immune system, and hence administration of Cpn10 polypeptides of the invention and/or Cpn10 nucleic acids of the invention provides a means of preventing and/or treating such diseases.

In certain embodiments, the method further comprises administering an immunosuppressive agent to the subject. Non-limiting examples of immunosuppressive agents include anti-inflammatory compounds, bronchodilatory compounds, cyclosporines, tacrolimus, sirolimus, mycophenolate mofetil, methotrexate, chromoglycalates, theophylline, leukotriene antagonist, and antihistamine, and combinations thereof. The immunosuppressive agent may also be an immunosuppressive drug or a specific antibody directed against B or T lymphocytes, or surface receptors that mediate their activation. For example, the immunosuppressive drug may be cyclosporine, tacrolimus, sirolimus, mycophenolate mofetil, methotrexate, chromoglycalates, theophylline, leukotriene antagonist, and antihistamine, or a combination thereof.

A disease treated in accordance with the methods of the invention may be an autoimmune inflammatory disease. Non-limiting examples of such diseases include rheumatoid arthritis, inflammatory bowel disease (Crohn's disease, ulcerative colitis), diabetes type I (insulin-dependent diabetes mellitus, juvenile onset diabetes), chronic fatigue syndrome, Alzheimer, Graves disease, osteoarthritis, collagen II arthritis, multiple sclerosis, systemic lupus erythematosus, autoimmune myocarditis, autoimmune ovarian disease, autoimmune thyroid disease, autoimmune neuritis, autoimmune hepatitis, autoimmune uveoretinitis, autoimmune uveitis, psoriasis, Sjogren's disease, sarcoidosis, dermatomyositis, leukocytoclastic vasculitis, myasthenia gravis, allergic encephalomyelitis, thyrotoxicosis, pernicious anemia, polymyalgia rheumatica and polymyositis.

A disease treated in accordance with the methods of the invention may be a non-autoimmune inflammatory disease. Non-limiting examples of such diseases include chronic obstructive pulmonary disease (COPD), leaky gut syndrome, cardiovascular disease (e.g. congestive heart disease), allergies (e.g. anaphylaxis, drug reactions, skin allergy, eczema, allergic rhinitis, urticaria, atopic dermatitis, allergic contact allergy, food allergy, allergic conjunctivitis, insect venom allergy), asthma, acute respiratory distress syndrome (ARDS), atherosclerosis and infectious diseases.

Additionally or alternatively, the disease treated in accordance with the methods of the invention may be graft-versus-host disease (GVHD).

A subject treated in accordance with the methods of the invention may be an individual of any mammalian species including, but not limited to, members of the genus ovine (e.g. sheep), bovine, equine, porcine, feline, canine, primates (e.g. humans), and rodents. Preferably, the subject is a human.

The subject may be suffering or suspected to be suffering from a disease (e.g. an inflammatory disease). Alternatively, the subject may have or be suspected to have a predisposition to developing a disease (e.g. an inflammatory disease).

The polypeptide or nucleic acid may be administered to the subject (e.g. a human subject) by any suitable route including, but not limited to, the parenteral (e.g. intravenous, intradermal, subcutaneous or intramuscular), mucosal (e.g. oral or intranasal) or topical route.

In certain embodiments, the invention provides the use of a Cpn10 polypeptide of the invention and/or a Cpn10 nucleic acid of the invention in the preparation of a medicament for treating a disease.

The disease may be an autoimmune inflammatory disease. Non-limiting examples of such diseases include rheumatoid arthritis, inflammatory bowel disease (Crohn's disease, ulcerative colitis), diabetes type I (insulin-dependent diabetes mellitus, juvenile onset diabetes), chronic fatigue syndrome, Alzheimer, Graves disease, osteoarthritis, collagen II arthritis, multiple sclerosis, systemic lupus erythematosus, autoimmune myocarditis, autoimmune ovarian disease, autoimmune thyroid disease, autoimmune neuritis, autoimmune hepatitis, autoimmune uveoretinitis, autoimmune uveitis, psoriasis, Sjogren's disease, sarcoidosis, dermatomyositis, leukocytoclastic vasculitis, myasthenia gravis, allergic encephalomyelitis, thyrotoxicosis, pernicious anemia, polymyalgia rheumatica and polymyositis.

The disease may be a non-autoimmune inflammatory disease. Non-limiting examples of such diseases include chronic obstructive pulmonary disease (COPD), infectious diseases, leaky gut syndrome, cardiovascular disease (e.g. congestive heart disease), allergies (e.g. anaphylaxis, drug reactions, skin allergy, eczema, allergic rhinitis, urticaria, atopic dermatitis, allergic contact allergy, food allergy, allergic conjunctivitis, insect venom allergy), asthma, acute respiratory distress syndrome (ARDS) and atherosclerosis and infectious diseases.

Additionally or alternatively, the disease treated in accordance with the methods of the invention may be graft-versus-host disease (GVHD).

Cpn10 polypeptides of the invention may be administered to a subject in the form of a composition. In general, suitable compositions for use in accordance with the methods of the invention may be prepared according to methods which are known to those of ordinary skill in the art and may include a pharmaceutically acceptable carrier, diluent and/or adjuvant. Compositions of the invention may be prepared comprising a Cpn10 polypeptide of the invention, or a combination of two or more different Cpn10 polypeptides of the invention. Such compositions may be included in pharmaceutical compositions comprising a pharmaceutically acceptable carrier, adjuvant and/or diluent. Compositions of the invention may comprise an immunosuppressive agent.

Embodiments of the invention also contemplate the administration of Cpn10 nucleic acids of the invention. In such situations a Cpn10 nucleic acid of the invention (e.g. DNA or cDNA) is typically operably linked to a promoter such that the appropriate polypeptide sequence is produced following administration of the nucleic acid to the subject. The nucleic acid may be administered to a subject in a vector. The vector may be a plasmid vector, a viral vector, or any other suitable vehicle adapted for the insertion of foreign sequences, their introduction into eukaryotic cells and the expression of the introduced sequences. The nucleic acid construct to be administered may comprise naked DNA or may be in the form of a composition, together with one or more pharmaceutically acceptable carriers.

Typically the vector is a eukaryotic expression vector and may include expression control and processing sequences such as a promoter, an enhancer, ribosome binding sites, polyadenylation signals and transcription termination sequences. The expression of a nucleic acid encoding a Cpn10 polypeptide of the invention may be increased in the immune cells of a subject using various methods of gene delivery known in the art. For example, an expression vector comprising a nucleic acid sequence encoding a Cpn10 polypeptide of the invention operably linked to an expression control sequence such as an inducible promoter may be administered to a subject to increase the production of the polypeptide. Alternatively, viral vectors (for example retroviral and adenoviral vectors) containing a nucleic acid sequence encoding a Cpn10 polypeptide of the invention may be administered to a subject in order to elicit the production of said protein. The delivery of a nucleic acid encoding a Cpn10 polypeptide of the invention may also be achieved by extracting cells from a subject, administering a vector containing the nucleic acid of interest, and then re-introducing the cells to the subject.

The efficacy of methods for preventing or treating diseases provided herein may be determined using standard techniques.

For therapeutic applications, such a determination will generally rely on establishing whether the disease is cured or at least partially arrested in the treated subject.

For preventative applications, such a determination will generally rely on establishing whether the subject develops the disease over a relevant time period following treatment.

These factors may be established by clinical examination of the subject for symptoms and manifestations of the disease in question. Additionally or alternatively, diagnostic assays may be performed to detect indicators of the disease, or the likelihood of developing the disease in question.

Screening for Immunosuppressive Agents

Cpn10 N-terminal domain variants of the invention may also be used in screening assays to identify agonists of their activity. These agonists will generally be antagonists of PRR signalling due to enhancing the suppressive effects on PRR-signalling mediated by the variants of the invention.

Compounds that bind to Cpn10 polypeptides of the invention may be capable of enhancing their activity.

Accordingly, in certain embodiments the invention provides methods of screening for an agent that binds to a Cpn10 polypeptide of the invention. The method comprises contacting the polypeptide with a candidate agent under conditions suitable for binding to occur between the candidate agent and polypeptide, and determining whether the agent binds to the polypeptide.

Compounds that bind to Cpn10 nucleic acids of the invention may be capable of enhancing their activity.

Accordingly, in certain embodiments the invention provides methods of screening for an agent that binds to a Cpn10 nucleic acid of the invention. The method comprises contacting the nucleic acid with a candidate agent under conditions suitable for binding to occur between the candidate agent and nucleic acid, and determining whether the agent binds to the nucleic acid.

It will be understood that "binding" of a candidate agent to a Cpn10 polypeptide of the invention or a Cpn10 nucleic acid of the invention encompasses direct binding, indirect binding (e.g. via one or more intermediary molecules), partial binding, complete binding, transient/temporary binding and stable/enduring binding.

In particular, desirable agents are candidate agents that are capable of binding to Cpn10 polypeptides of the invention and/or Cpn10 nucleic acids of the invention and enhancing their activity.

Candidate agents for use in the screening methods of the invention may be derived from any source.

For example, the candidate agent may be naturally occurring or synthetic.

Potential candidate agents may be generated for screening in the methods of the invention by a number of techniques known to those skilled in the art. For example, methods such as X-ray crystallography and nuclear magnetic resonance spectroscopy may be used to model the structure of Cpn10 polypeptides of the invention and Cpn10 nucleic acids of the invention, thus facilitating the design of potential immunosuppressive agents using computer-based modelling. Various forms of combinatorial chemistry may also be used to generate putative candidate agents.

A candidate agent may be of any molecular weight, for example, at least about 100, 200, 300, 400, 500, 750, 1000, 2000, 3000, 4000, 5000, 7000, 9000, 10000, 20000, 30000, 40000, 50000, 60000, 70000, 80000, 90000, or 100000 daltons.

A candidate agent can be any chemical compound, non-limiting examples of which include amino acids, nucleic acids, peptide nucleic acids, lipids, polypeptides, carbohydrates, and nucleosides other non-limiting examples include, peptidomimetics (e.g. peptoids), amino acid analogues, polynucleotides, polynucleotide analogues, nucleotides, nucleotide analogues, metabolites, metabolic analogues, and organic or inorganic compounds (including heteroorganic and organometallic compounds).

In certain embodiments high-throughput methods are used to screen large libraries of chemicals. Such libraries of candidate compounds can be generated or purchased from commercial sources. For example, a library can include 10,000, 50,000, or 100,000 or more unique compounds. By way of example only, a library may be constructed from heterocycles including benzimidazoles, benzothiazoles, benzoxazoles, furans, imidazoles, indoles, morpholines, naphthalenes, piperidines, pyrazoles, pyridines, pyrimidines, pyrrolidines, pyrroles, quinolines, thiazoles, thiphenes, and triazines. A library may comprise one or more classes of chemicals, for example, those described in Carrell et al., (1994), Angew. Chem. Int. Ed. Engl, 33:2059; Carell et al., (1994), Angew. Chem. Int. Ed. Engl. 33:2061; Cho et al., (1993), Science 261:1303-1305; DeWitt et al., (1993), Proc. Natl. Acad. Sci. U.S.A. 90:6909-6913; Erb et al., (1994), Proc. Natl. Acad. Sci. USA 91:11422-11426; Gallop et al., (1994), J. Med. Chem. 37:1233-1251; and Zuckermann et al., (1994), J. Med. Chem. 37:2678-2685.

Screening methods of the invention involve contacting the candidate agent with a Cpn10 polypeptide of the invention or a Cpn10 nucleic acid of the invention.

Agents which bind, or otherwise interact with Cpn10 polypeptides of the invention and/or Cpn10 nucleic acids of the invention, and specifically agents which enhance their activity, may be identified by a variety of suitable methods. Non limiting methods include the two-hybrid method, co-immunoprecipitation, affinity purification, mass spectroscopy, tandem affinity purification, phage display, label transfer, DNA microarrays/gene coexpression and protein microarrays.

For example, a two-hybrid assay may be used to determine whether a candidate agent interacts or binds with a Cpn10 polypeptide of the invention. The yeast two-hybrid assay system is a yeast-based genetic assay typically used for detecting protein-protein interactions (see, for example, Fields and Song, (1989), Nature, 340: 245-246). The assay makes use of the multi-domain nature of transcriptional activators. For example, the DNA-binding domain of a known transcriptional activator may be fused to a Cpn10 polypeptide of the invention and the activation domain of the transcriptional activator fused to the candidate agent. Interaction between the candidate agent and the polypeptide will bring the DNA-binding and activation domains of the transcriptional activator into close proximity. Subsequent transcription of a specific reporter gene activated by the transcriptional activator allows the detection of an interaction.

In a modification of the technique above, a fusion protein may be constructed by fusing a Cpn10 polypeptide of the invention to a detectable tag (e.g. alkaline phosphatase) and using a modified form of immunoprecipitation as described by Flanagan and Leder (Flanagan and Leder, (1990), Cell, 63:185-194).

Additionally or alternatively, co-immunoprecipitation may be used to determine whether a candidate agent interacts or binds with a Cpn10 polypeptide of the invention. Using this technique, a sample of peripheral blood mononuclear cells may be lysed under non-denaturing conditions suitable for the preservation of protein-protein interactions. The resulting solution can then be incubated with an antibody specific for a Cpn10 polypeptide of the invention and immunoprecipitated from the bulk solution, for example, by capture with an antibody-binding protein attached to a solid support. Immunoprecipitation of the polypeptide by this method facilitates the co-immunoprecipitation of an agent associated with that polypeptide. The identification an associated agent can be established using a number of methods known in the art, including but not limited to SDS-PAGE, western blotting, and mass spectrometry.

Additionally or alternatively, the phage display method may be used to determine whether a candidate agent interacts or binds with a Cpn10 polypeptide of the invention. Phage display is a test to screen for protein interactions by integrating multiple genes from a gene bank into phage. Under this method, recombinant DNA techniques are used to express numerous genes as fusions with the coat protein of a bacteriophage such that the polypeptide product of each gene is displayed on the surface of the viral particle. A whole library of phage-displayed polypeptide products of interest can be produced in this way. The resulting libraries of phage-displayed polypeptide products may then be screened for the ability to bind to a Cpn10 polypeptide of the invention. DNA extracted from interacting phage contains the sequences of interacting polypeptides.

Additionally or alternatively, affinity chromatography may be used to determine whether a candidate agent interacts or binds with a Cpn10 polypeptide of the invention. For example, a Cpn10 polypeptide of the invention may be immobilised on a support (such as sepharose) and cell lysates passed over the column. Proteins binding to an immobilised Cpn10 polypeptide of the invention may then be eluted from the column and identified, for example by N-terminal amino acid sequencing.

Agents which bind, or otherwise interact with Cpn10 nucleic acids of the invention, and specifically agents which modulate their activity may be identified by a variety of methods known in the art, non-limiting examples of which include electrophoresis, gel shift assays, surface plasmon resonance ATPase assays, circular dichroism, mass spectroscopy, and nuclear magnetic resonance. A specific example of a screening assay for the detection of DNA-binding molecules is described in U.S. Pat. No. 5,726,014.

Cpn10 polypeptides of the invention and Cpn10 nucleic acids of the invention can be used in high-throughput screens to assay candidate agents for the ability to bind to, or otherwise interact therewith. These candidate compounds can be further screened against functional polypeptides and nucleic acids to determine the effect of the agent on activity.

The present invention also contemplates the identification of compounds which may enhance the activity of Cpn10 polypeptides of the invention by altering expression of the polypeptide. In this case, such compounds may be identified by comparing the level of expression of the polypeptide in the presence of a candidate compound with the level of expression in the absence of the candidate compound.

The activity of a Cpn10 polypeptide of the invention identified to be bound by a particular candidate agent may be assessed, for example, by contacting a sample of immune cells (e.g. peripheral blood mononuclear cells) with the polypeptide and agent in the presence of a PRR ligand. The degree of PRR-mediated signalling induced in the cells can then be assessed using methods known in the art. Suitable methods include, but are not limited to, those described in the section above entitled "Immunosuppression". For example, the degree of PRR-mediated signalling induced in the cells may be assessed by measuring the production and/or secretion of inflammatory mediators (e.g. cytokines and chemokines), measuring the expression of cell surface receptors for inflammatory mediators or other cell surface markers of activation, detecting cellular signals indicative of activation (e.g. TLR-mediated NF-κB activation, type-1 interferon production, tyrosine or serine/threonine phosphorylation, ADP ribosylation etc.), and/or detecting activation of the complement system.

The activity of a Cpn10 nucleic acid of the invention identified to be bound by a particular candidate agent may be assessed, for example, by measuring the production of the encoded polypeptide upon exposure to the candidate agent. This may be achieved, for example, using any technique capable of detecting and/or quantifying proteins. Suitable methods are known in the art and include, for example, immunohistochemistry, SDS-PAGE, immunoassays, proteomics and the like. Additionally or alternatively, levels of transcription of the nucleic acid in the presence of the identified agent can be measured using techniques, including, for example, transcription quantitative polymerase chain reaction (RT-PCR).

It will be appreciated that the techniques described above are merely examples of the types of methods that may be utilised to identify agents that are capable of interacting with, or enhancing the activity of Cpn10 polypeptides of the invention and/or Cpn10 nucleic acids of the invention. Other suitable methods will be known by persons skilled in the art and are within the scope of the invention.

Using the methods described above, an agent may be identified that is agonist of a Cpn10 polypeptide of the invention or Cpn10 nucleic acid of the invention. Agents which are agonists enhance one or more of the biological activities of the polypeptide or nucleic acid. Preferably, the biological activity enhanced by the agonist is binding of the polypeptide to a PRR ligand.

Methods for the generation of antibodies are known in the art and are described in the section above entitled "Antibodies".

Compositions

The invention provides compositions comprising one or more Cpn10 polypeptides of the invention and/or one or more Cpn10 nucleic acids of the invention. Compositions of the invention may comprise one or more antibodies of the invention.

A composition of the invention may comprise a pharmaceutically acceptable carrier, adjuvant and/or diluent. The carriers, diluents and adjuvants must be "acceptable" in terms of being compatible with the other ingredients of the composition, and not deleterious to the recipient thereof. Non-limiting examples of pharmaceutically acceptable carriers or diluents are demineralised or distilled water; saline solution; vegetable based oils such as peanut oil, safflower oil, olive oil, cottonseed oil, maize oil; sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or isopropanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrolidone; agar; gum tragacanth or gum acacia, and petroleum jelly. Typically, the carrier or carriers will form from 10% to 99.9% by weight of the compositions.

Additionally or alternatively, a composition of the invention may comprise an immunosuppressive agent, non-limiting examples of which include anti-inflammatory compounds, bronchodilatory compounds, cyclosporines, tacrolimus, sirolimus, mycophenolate mofetil, methotrexate, chromoglycalates, theophylline, leukotriene antagonist, and antihistamine, and combinations thereof. The immunosuppressive agent may also be an immunosuppressive drug or a specific antibody directed against B or T lymphocytes, or surface receptors that mediate their activation. For example, the immunosuppressive drug may be cyclosporine, tacrolimus, sirolimus, mycophenolate mofetil, methotrexate, chromoglycalates, theophylline, leukotriene antagonist, and antihistamine, or a combination thereof.

Additionally or alternatively, a composition of the invention may comprise an adjuvant. Any suitable adjuvant may be included in a vaccine of the invention. For example, an aluminium-based adjuvant may be utilised. Suitable aluminium-based adjuvants include, but are not limited to, aluminium hydroxide, aluminium phosphate and combinations thereof. Other specific examples of aluminium-based adjuvants that may be utilised are described in European Patent No. 1216053 and U.S. Pat. No. 6,372,223.

Oil in water emulsions may be utilised as adjuvants in the compositions and vaccines of the invention. Oil in water emulsions are well known in the art. In general, the oil in water composition will comprise a metabolizable oil, for example, a fish oil, a vegetable oil, or a synthetic oil.

Examples of suitable oil in water emulsions include those described in European Patent No. 0399843, U.S. Pat. No. 7,029,678 and PCT publication No. WO 2007/006939. The oil in water emulsion may be utilised with other adjuvants and/or immunostimulants.

Non-limiting examples of other suitable adjuvants include immunostimulants such as granulocyte-macrophage colony-stimulating factor (GM-CSF), monophosphoryl lipid A (MPL), cholera toxin (CT) or its constituent subunit, heat labile enterotoxin (LT) or its constituent subunit, toll like receptor ligand adjuvants such as lipopolysaccharide (LPS) and derivatives thereof (e.g. monophosphoryl lipid A and 3-Deacylated monophosphoryl lipid A), muramyl dipeptide (MDP) and F protein of Respiratory Syncytial Virus (RSV).

Additionally or alternatively, a composition of the invention may comprise a steroid, such as a corticosteroid.

A composition of the invention may be in a form suitable for administration by injection, in a form of a formulation suitable for oral ingestion (such as capsules, tablets, caplets, elixirs, for example), in a form of an ointment, cream or lotion suitable for topical administration, in a form suitable for delivery as an eye drop, in an aerosol form suitable for administration by inhalation, such as by intranasal inhalation or oral inhalation, or in a form suitable for parenteral administration, that is, subcutaneous, intramuscular or intravenous injection.

For administration as an injectable solution or suspension, non-toxic parenterally acceptable diluents or carriers can include, Ringer's solution, isotonic saline, phosphate buffered saline, ethanol and 1,2 propylene glycol.

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl stearate which delay disintegration.

Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

The emulsions for oral administration may further comprise one or more emulsifying agents. Suitable emulsifying agents include dispersing agents as exemplified above or natural gums such as guar gum, gum acacia or gum tragacanth.

Methods for preparing parenterally administrable compositions are apparent to those skilled in the art, and are described in more detail in, for example, Remington's Pharmaceutical Science, 15th ed., Mack Publishing Company, Easton, Pa.

Topical formulations of the invention may comprise an active ingredient together with one or more acceptable carriers, and optionally any other therapeutic ingredients. Formulations suitable for topical administration include liquid or semi-liquid preparations suitable for penetration through the skin to the site where treatment is required, such as liniments, lotions, creams, ointments or pastes, and drops suitable for administration to the eye, ear or nose.

Drops according to the invention may comprise sterile aqueous or oily solutions or suspensions. These may be prepared by dissolving the active ingredient in an aqueous solution of a bactericidal and/or fungicidal agent and/or any other suitable preservative, and optionally including a surface active agent. The resulting solution may then be clarified by filtration, transferred to a suitable container and sterilised. Sterilisation may be achieved by autoclaving or maintaining at 90° C.-100° C. for half an hour, or by filtration, followed by transfer to a container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the invention include those suitable for application to the skin or eye. An eye lotion may comprise a sterile aqueous solution optionally containing a bactericide and may be prepared by methods similar to those described above in relation to the preparation of drops. Lotions or liniments for application to the skin may also include an agent to hasten drying and to cool the skin, such as an alcohol or acetone, and/or a moisturiser such as glycerol, or oil such as castor oil or arachis oil.

Creams, ointments or pastes according to the invention are semi-solid formulations of the active ingredient for external application. They may be made by mixing the active ingredient in finely-divided or powdered form, alone or in solution or suspension in an aqueous or non-aqueous fluid, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil, wool fat or its derivatives, or a fatty acid such as stearic or oleic acid together with an alcohol such as propylene glycol or macrogols.

A composition of the invention may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

A composition of the invention may be administered in the form of a liposome. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to Prescott, (Ed), (1976), "*Methods in Cell Biology*", Volume XIV, Academic Press, New York, N.Y. p. 33 et seq.

The compositions may be conjugated to an array of polyethylene glycol (PEG) derivatives. The addition of PEG to proteins (PEGylation) is a well established method for decreasing the plasma clearance rates of proteins, thereby increasing their efficacy (Nucci et al., 1991, *Adv. Drug Del. Rev.* 6:133). Additional benefits of PEGylation may include, greater stability of proteins, decreased immunogenicity, enhanced solubility and decreased susceptibility to proteolysis (Sheffield W. 2001, *Curr Drug Targets Cardiovasc Haematol Disord.* 1:1-22). PEG molecules contain the basic repeating structure of —$(OCH_3CH_2)$n-OH and are classified into groups according to their molecular weight. PEG derivatives are conjugated to proteins to increase their hydrodynamic radius and in general, their increase in half-life is directly related to the size of the PEG chain attached (Sheffield W. 2001, *Curr Drug Targets Cardiovasc Haematol Disord.* 1:1-22).

The compositions may also be administered in the form of microparticles. Biodegradable microparticles formed from polylactide (PLA), polylactide-co-glycolide (PLGA), and epsilon-caprolactone (ε-caprolactone) have been extensively used as drug carriers to increase plasma half life and thereby prolong efficacy (R. Kumar, M., 2000, *J Pharm Pharmaceut Sci.* 3(2) 234-258). Microparticles have been formulated for the delivery of a range of drug candidates including vaccines, antibiotics, and DNA. Moreover, these formulations have been developed for various delivery routes including parenteral subcutaneous injection, intravenous injection and inhalation.

The compositions may incorporate a controlled release matrix that is composed of sucrose acetate isobutyrate (SAIB) and organic solvent or organic solvents mixture. Polymer additives may be added to the vehicle as a release modifier to further increase the viscosity and slow down the release rate. SAIB is a well known food additive. It is a very hydrophobic, fully esterified sucrose derivative, at a nominal ratio of six isobutyrate to two acetate groups. As a mixed ester, SAIB does not crystallize but exists as a clear viscous liquid. Mixing SAIB with a pharmaceutically accepted organic solvent such as ethanol or benzyl alcohol decreases the viscosity of the mixture sufficiently to allow for injection. An active pharmaceutical ingredient may be added to the SAIB delivery vehicle to form SAIB solution or suspension formulations. When the formulation is injected subcutaneously, the solvent diffuses from the matrix allowing the SAIB-drug or SAIB-drug-polymer mixtures to set up as an in situ forming depot.

For the purposes of the present invention molecules and agents may be administered to subjects as compositions either therapeutically or preventively. For example, a is composition of the invention may be administered as a vaccine (e.g. a preventative vaccine or a therapeutic vaccine). In a therapeutic application, compositions are administered to a patient already suffering from a disease, in an amount sufficient to cure or at least partially arrest the disease and its complications. The composition should provide a quantity of the molecule or agent sufficient to effectively treat the patient.

Embodiments of the invention also contemplate the administration of Cpn10 nucleic acids of the invention. In such situations the nucleic acid is typically operably linked to a promoter such that the appropriate polypeptide sequence is produced following administration of the nucleic acid to the subject. The nucleic acid may be administered to subjects in a vector. The vector may be a plasmid vector, a viral vector, or any other suitable vehicle adapted for the insertion of foreign sequences, their introduction into eukaryotic cells and the expression of the introduced sequences. Typically the vector is a eukaryotic expression vector and may include expression control and processing sequences such as a promoter, an enhancer, ribosome binding sites, polyadenylation signals and transcription termination sequences. The nucleic acid construct to be administered may comprise naked DNA or may be in the form of a composition, together with one or more pharmaceutically acceptable carriers.

Routes of Administration

Administration to a subject of a Cpn10 polypeptide of the invention, Cpn10 nucleic acid of the invention, composition of the invention, or antibody of the invention may be performed by any suitable route including, but not limited to, the parenteral (e.g. intravenous, intradermal, subcutaneous or intramuscular), mucosal (e.g. oral or intranasal) or topical route.

Accordingly, the polypeptide, nucleic acid, antibody or composition may be administered in a form suitable for administration by injection, in the form of a formulation suitable for oral ingestion (such as capsules, tablets, caplets, elixirs, for example), in the form of an ointment, cream or lotion suitable for topical administration, in a form suitable for delivery as an eye drop, in an aerosol form suitable for administration by inhalation, such as by intranasal inhalation or oral inhalation, or in a form suitable for parenteral administration, that is, subcutaneous, intramuscular or intravenous injection.

Formulations for intranasal administration may be provided in a freeze-dried powder form, in liquid form as nose drops, spray, or suitable for inhalation, as powder, as cream, or as emulsion.

In one embodiment, the polypeptide, nucleic acid, antibody or composition is provided in an oral form for administration to a subject in accordance with the methods of the invention. Oral administration may assist in methods of treatment designed to re-induce tolerance to antigen(s) present in self proteins sharing sequence homology with those of pathogenic bacterial protein(s).

The polypeptide, nucleic acid, antibody or composition may be administered to a subject therapeutically or preventively.

In a therapeutic application, the polypeptide, nucleic acid, antibody or composition is administered to a subject already suffering from a disease (e.g. an inflammatory disease) in an amount sufficient to cure or at least partially arrest the disease and its complications. Typically, in therapeutic applications, the treatment would be for the duration of the disease state or condition.

In a preventative application, the polypeptide, nucleic acid, antibody or composition is administered to a subject that is not suffering from a disease at the time of administration.

The therapeutically effective dose level for any particular subject will depend upon a variety of factors including: the disease being treated and the severity of the disease; activity of the compound or agent employed; the composition employed; the age, body weight, general health, sex and diet of the subject; the time of administration; the route of administration; the rate of sequestration of the polypeptide, nucleic acid, antibody or composition; the duration of the treatment; drugs used in combination or coincidental with the treatment, together with other related factors known in the art.

Further, it will be apparent to one of ordinary skill in the art that the optimal quantity and spacing of individual dosages will be determined by the nature and extent of the disease being treated, the form, route and site of administration, and the nature of the particular subject being treated.

One skilled in the art would be able, by routine experimentation, to determine an effective, non-toxic amount of the polypeptide, nucleic acid, antibody or composition which would be required to effectively prevent or treat applicable autoimmune diseases.

For example, an optimal dosage may be derived from administering serially diluted preparations comprising the polypeptide, nucleic acid, antibody or composition in conjunction with a suitable testing procedure. Additionally or alternatively, a matrix comprising various different dosages and dosage frequency can be designed and applied to one or more groups of experimental subjects to determine optimal dosages.

Generally, an effective dosage is expected to be in the range of about 0.0001 mg to about 1000 mg of active agent per kg body weight per 24 hours; typically, about 0.001 mg to about 750 mg of active agent of active agent per kg body weight per 24 hours; about 0.01 mg to about 500 mg of active agent per kg body weight per 24 hours; about 0.1 mg to about 500 mg of active agent per kg body weight per 24 hours; about 0.1 mg to about 250 mg of active agent per kg body weight per 24 hours; or about 1.0 mg to about 250 mg of active agent per kg body weight per 24 hours.

More typically, an effective dose range is expected to be in the range about 1.0 mg to about 200 mg of active agent per kg body weight per 24 hours; about 1.0 mg to about 100 mg of active agent per kg body weight per 24 hours; about 1.0 mg to about 50 mg of active agent per kg body weight per 24 hours; about 1.0 mg to about 25 mg of active agent per kg body weight per 24 hours; about 5.0 mg to about 50 mg of active agent per kg body weight per 24 hours; about 5.0 mg to about 20 mg of active agent per kg body weight per 24 hours; or about 5.0 mg to about 15 mg of active agent per kg body weight per 24 hours.

Alternatively, an effective dosage may be in the range of about 0.1 mg of active ingredient per kg body weight to about 2 mg of active ingredient per kg body weight twice weekly.

Alternatively, an effective dosage may be up to about 500 mg/m$^2$. Generally, an effective dosage is expected to be in the range of about 25 to about 500 mg/m$^2$, preferably about 25 to about 350 mg/m$^2$, more preferably about 25 to about 300 mg/m$^2$, still more preferably about 25 to about 250 mg/m$^2$, even more preferably about 50 to about 250 mg/m$^2$, and still even more preferably about 75 to about 150 mg/m$^2$.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

EXAMPLES

The invention will now be described with reference to specific examples, which should not be construed as in any way limiting Example 1

Production of Cpn10 Polypeptides

To further define the production process of Cpn10 polypeptides of the invention, the following non-limiting examples are provided.

Expression of human Cpn10 with or without modification was achieved with either a heat-inducible expression plasmid transformed into the *E. coli* strain XL1-Blue (Stratagene), or IPTG-inducible expression plasmids pET30 KanR and pET23 AmpR (Novagen) transformed into the *E. coli* strain BL21 (DE3) (Invitrogen).

Utilising the heat-inducible expression plasmid, Cpn10 was produced and purified to >90% purity by a single passage over a Macro-Prep High Q (BioRad) column, equilibrated at pH8, essentially as described by Ryan et al. (1995, *J Biol Chem* 270: 22037-22043). The unbound material, containing Cpn10, was then further purified by S-Sepharose and then Gel-Filtration (Superdex 200, Amersham Biosciences) Chromatography. Purified Cpn10 in 50 mM Tris-HCl (pH 7.6) and 150 mM NaCl, was filtered through an Acrodisc with a 0.2 mm Mustang E membrane according to the manufacturer's instructions (Pall Corporation, Ann Arbor, Mich. Cat No. MSTG5E3) to remove residual endotoxins and was stored at −80° C.

Utilising the IPTG-inducible expression plasmids, cells were grown in LB containing the appropriate antibiotic (100 µg/ml Amp and 50 µg/ml Kan) until $OD_{600\,nm}$ of 0.5, Cpn10 production was then induced with 1 mM IPTG for 5 hr. Cells were pelleted by centrifugation (6,000×g) for 10 min at 4° C., resuspended in 25 mM Tris (pH 7.5) and homogenised at 8,000 psi four times. Insoluble material was removed by centrifugation at 15,000×g for 30 min at 4° C. The supernatant containing Cpn10 was vortexed with 0.1% (w/v) PEI, incubated on ice for 5 min then centrifuged at 15,000×g for 30 min at 4° C. to remove nucleic acids and numerous *E. coli* proteins. The Cpn10-enriched supernatant was passed through a 0.45 µm filter syringe and loaded onto a Big Bead Sulfopropyl-Sepharose cation exchange column pre-equilibrated in 25 mM Tris (pH 7.5), elution was achieved with a 0 to 0.5M NaCl gradient. Fractions containing Cpn10 were pooled and diluted 1 in 10 into 25 mM Tris (pH 7.5)+2M Ammonium Sulphate and loaded onto a Butyl-S-Sepharose Hydrophobic Interaction Chromatography (HIC) column, elution was achieved with a 0-60% gradient of 25 mM Tris (pH 7.5). Fractions containing Cpn10 were dialysed into 25 mM Tris (pH 8)+1 mM EDTA and concentrated to ~10 mg/ml. To remove residual endotoxins and nucleic acids, Cpn10 was finally passed over a Capto-Q-Sepharose column, pre-equilibrated in 25 mM Tris (pH 7.5)+1 mM EDTA. Purified Cpn10 was dialysed into 50 mM Tris-HCl pH 7.6+150 mM NaCl and diluted to ~5 mg/ml for storage at −80° C.

Figure 2A:
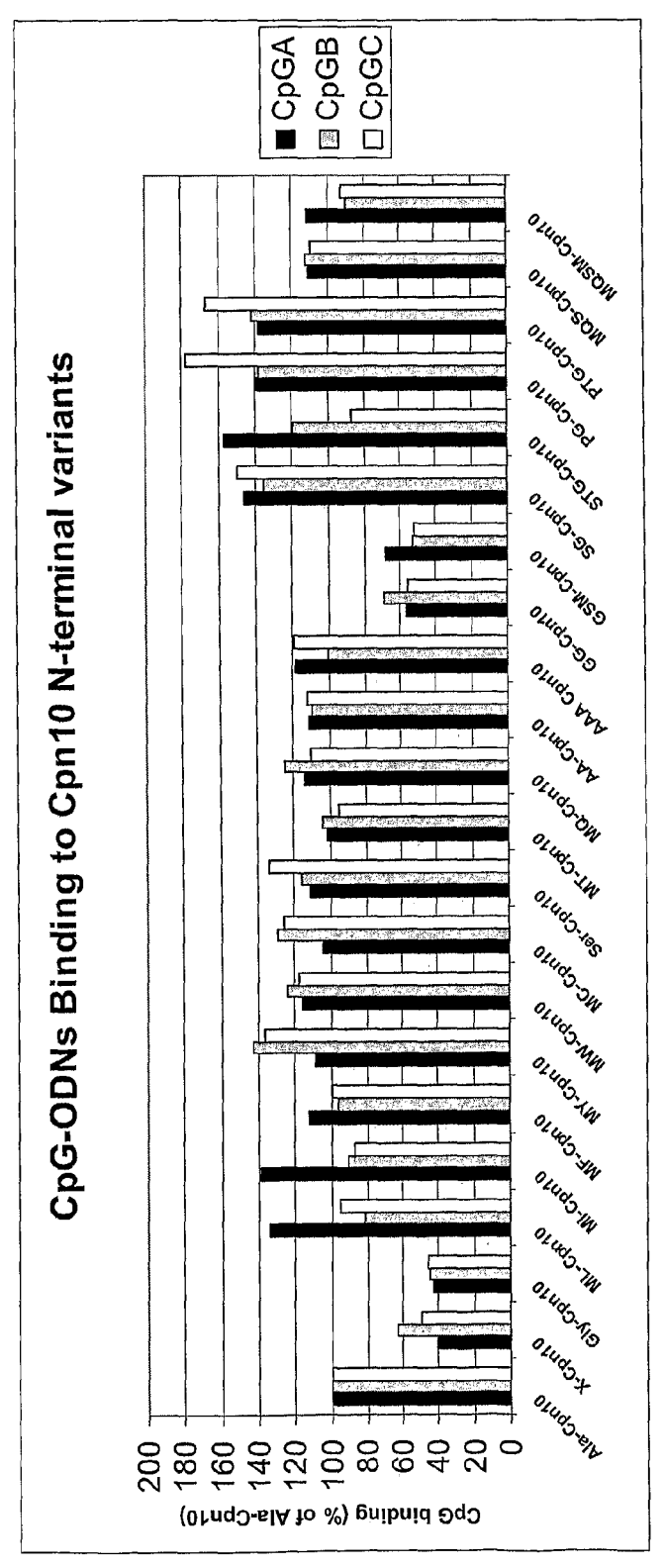
Figure 2B:
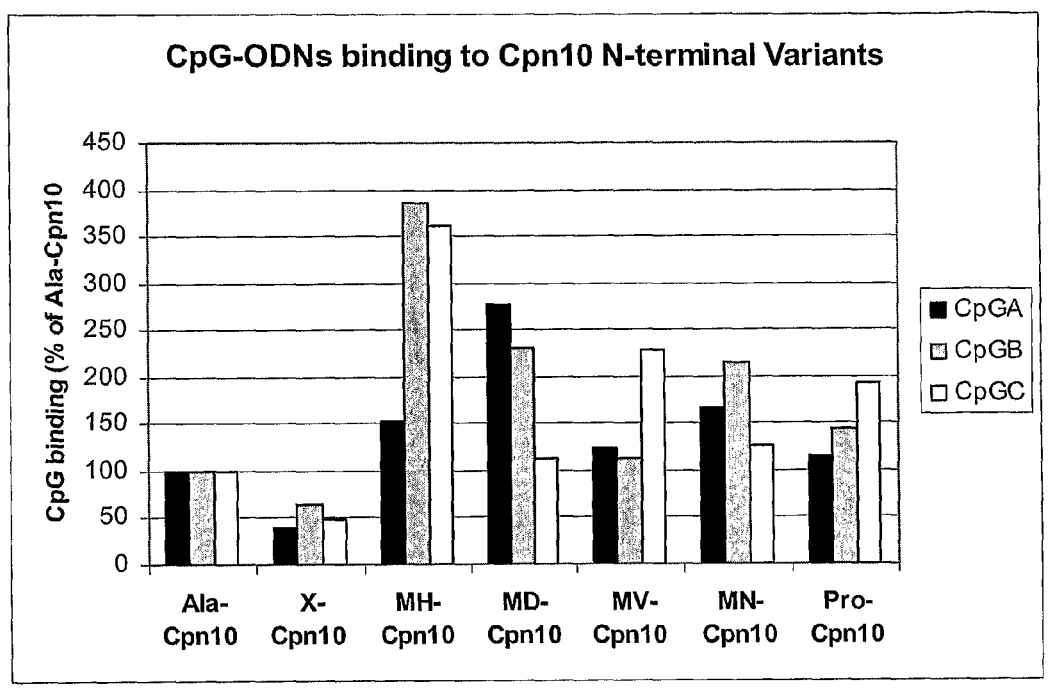
Figure 2C:
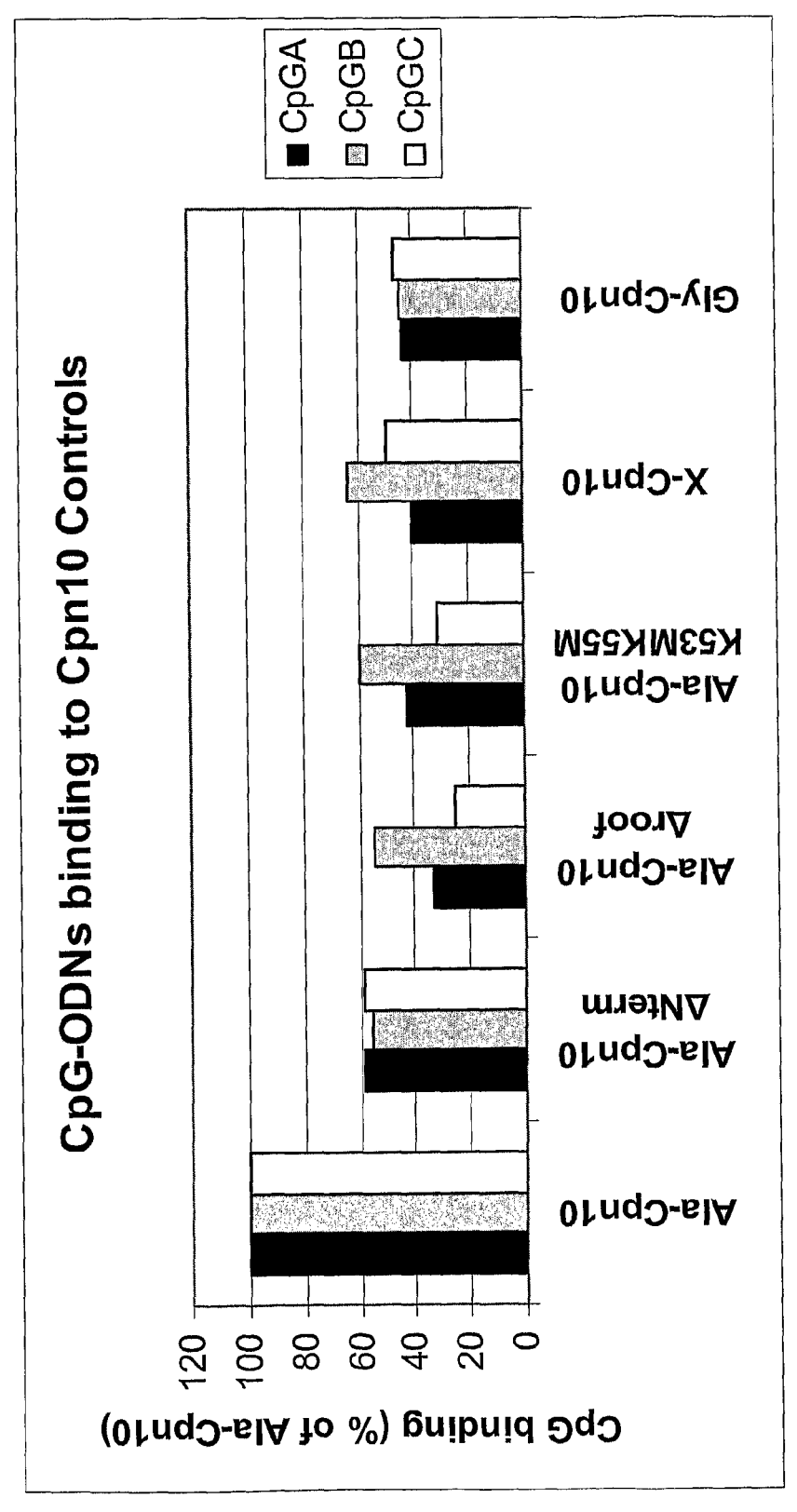
Figure 3:
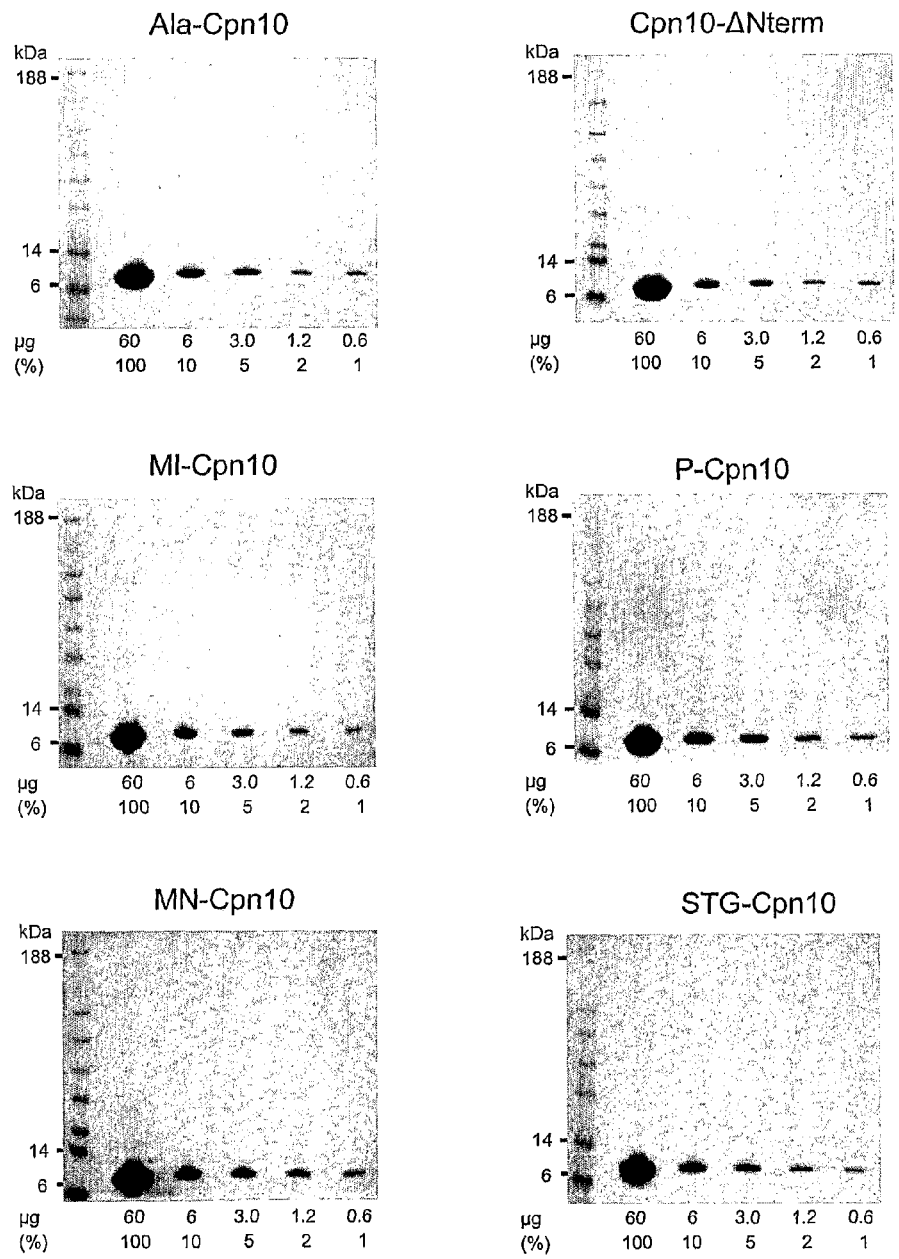
FIG. 3 shows representative SDS-PAGE electrophoretograms demonstrating the purity of generated recombinant Cpn10 proteins.

The purity of Cpn10, such as various Cpn10 mutant polypeptides as shown in FIG. 2 was determined to be >99% by Coomassie brilliant staining on SDS-PAGE. Aliquots were thawed once prior to use.

Example 2

Quantitative Analysis of Cpn10 Binding to CpG Oligonucleotides (ODNs)

To determine the amount of binding of the Cpn10 mutants to ODNs, the mutants were formulated at 10 μg/μl in PBS pH7.2 (Invitrogen) and 50 μg was adsorbed to triplicate wells of a 96 well plate 16 hr at 4° C. Following the decanting of non-bound protein, the plate was blocked with 1% BSA and 5% sucrose in PBS pH7.2 for 2 hr at 23° C. 50 μl of 3' or 5'-biotin labeled human ODN-2216 class-A, human ODN-2006 class-B, or human ODN-M362 class-C (TLR9 agonists) (Proligo/Sigma) formulated at 0.01 μg/μl in PBS pH 7.2 was added to each well and incubated for 2 hr at 23° C. Unbound ligand was removed with five PBS (pH7.2)+0.05% Tween 20 washes. Bound CpG-ODNs were analysed with a Streptavidin-HRP and TMB detection system at A450 nm.

In FIG. 1 a quantitative analysis at physiological salt concentrations (~150 mM) highlights the stronger interaction of CpG-ODNs with a number of Cpn10 N-terminus variants compared to Ala-Cpn10.

For example, variants MV-Cpn10, ML-Cpn10, MI-Cpn10, MH-Cpn10, Pro-Cpn10, MF-Cpn10, MY-Cpn10, MW-Cpn10, MC-Cpn10, Ser-Cpn10, MT-Cpn10, MD-Cpn10, MN-Cpn10, MQ-Cpn10, AA-Cpn10, AAA-Cpn10, SG-Cpn10, STG-Cpn10, PG-Cpn10, PTG-Cpn10, MQS-Cpn10 and MQSN-Cpn10 each displayed stronger interaction with at least one CpG-class (i.e. CpG-class A, B and/or C) than Ala-Cpn10.

Example 3

Molecular Modelling

To be biologically active proteins must adopt a specific folded three-dimensional structure, and this structure is determined by the amino acid sequence of the protein. The unique structures and properties of amino acid side chains determine the specific biological function of a protein. Numerous non-covalent interactions such as hydrogen bonding, ionic interactions, Van der Waals forces and hydrophobic packing contribute to the stability and flexibility of the protein fold.

The X-ray crystal structure of human Ala-Cpn10 (lacking the flexible mobile loops) at 2 Å resolution was obtained. The Cpn10 monomer is comprised of a core anti-parallel β-barrel region flanked by a β-hairpin "roof loop" region and a "mobile loop" region. The crystal structure reveals that the N-terminus of Ala-Cpn10 forms a β-hairpin and lies in a well-ordered linear extended conformation across the top of the Cpn10 dome-like structure in close proximity to a specific region of the roof loops. In a handful of X-ray crystal structures the N-terminus of certain subunits within the Cpn10 heptamer was observed to undergo large conformational changes indicating that the appendage is quite flexible and fulfill an important biological function, such as regulating nucleic acid binding. Molecular modeling provides indication that the flexible N-terminus of Ala-Cpn10 may dock onto the roof loop by the interaction of Alanine (at amino acid position-1, hereafter called Ala-1) into a small structural pocket on the roof loop formed by residues Ser52 to Gly57 (akin to a lock and key). Two key residues in the start of the roof loop, Lys53 and Lys55 are surrounded by smaller residues (Ser52, Gly54, Gly56 and Gly57), and by virtue of their extended side chain $CH_2$—$CH_2$—$CH_2$—$CH_2$—$NH_2$ are thought to be able to form this pocket, separated by Gly54. An analysis of the amino acid side chain interactions and packing geometries (using the Thornton and Singh Atlas of Protein Side-Chain Interactions; Singh J & Thornton J M (1992). *Atlas of Protein Side-Chain Interactions, Vols. I & II*, IRL press, Oxford) indicates that the $CH_3$ side chain of Ala-1 is able to interact and form one large significant cluster (and a second smaller one) with these Lys side chains. This binding of Ala-1 into the roof loop structural pocket of Lys53-Lys55 may effectively anchor the flexible N-terminus, conferring tight nucleic acid binding.

The Atlas of Protein Side-Chain Interactions (Thornton and Singh) describes all 400 possible pairwise interactions between the 20 different types of amino acid side chains and is considered the key reference for determining how amino acid side chains interact and pack (clustering) against each other. The significance of any clustering in the contacts of the side chains is assessed with reference to packing-geometries and Van der Waals forces. Significance is assessed by a $Chi^2$ test against a random distribution. The database and software to analyze these interactions is hosted by University College London at the Thornton Group Services and Databases as part of the EMBL European Bioinformatics Institute; http://www.biochem.ucl.ac.uk/bsm/sidechains/index.html). This database was used to model the effect of N-terminal mutations of Ala-Cpn10 on binding to nucleic acid ligands and immuno-modulatory function.

Perturbation of the binding of Ala-1 to Lys53Lys55 may alter the structural conformation of Ala-Cpn10 and impair the ability to bind to nucleic acids (eg CpG-ODN). The removal of the complete N-terminus (Ala-Cpn10-ΔNterm), or the roof loop (Ala-Cpn10-ΔRoof) of the molecule prevented the binding of Ala-1 into this pocket and severely impairs the ability of Cpn10 to bind to CpG-ODN (see FIG. 1). Likewise, the mutation of the Lys53 and Lys55 to a different amino acid was observed to destroy the binding pocket and severely impair the binding to CpG-ODN (see FIG. 1).

Shortening of the N-terminal by the removal of Ala at position-1 (Ala-1) was also observed to impair binding to CpG-ODN, as shown by the mutant X-Cpn10 (see FIG. 1).

Glycine is a similar amino acid to alanine in both size and structure, and differs in that glycine has only a —H side chain compared to alanine's —$CH_3$ side chain. The substitution of Ala-1 for glycine also resulted in an impaired immunomodulatory function presumably because it is unable to fit correctly into the pocket (akin to placing a very similar, but incorrect key into the lock). Modeling of the interaction of glycine with the Lys53Lys55 side chains provided indication that six large and significant clusters can be formed between the side chains. These clusters are different than those formed by Ala-Cpn10 and therefore result in a different structural conformation of the molecule, and impaired binding to CpG-ODN.

Hence, the correct binding of the N-terminal Ala-1 into the structural pocket of the roof loop is believed to be necessary for the binding of CpG-ODN and the function of Ala-Cpn10 as a modulator of PRR signalling.

Protein translation is started at the initiation methionine. According to the "N-end rule", in some proteins the initiation methionine is removed, dependant on the identity of the following amino acid. Using mass spectrometry it was determined that the iniation methionine is cleaved off Cpn10 if the adjacent amino acid is an alanine (as is the case for Ala-Cpn10), a glycine (as is the case for Gly-Cpn10) a proline or serine. For all other amino acids the methionine is left intact. Proline (Pro), serine (Ser) and methionine (Met) are all larger amino acids than alanine.

Given the hypothesis of how the structural conformation of Ala-Cpn10 is required for binding to CpG-ODN, it was postulated if the Ala-1 amino acid is replaced by a larger, bulkier amino acid, it may not be able to fit correctly into the pocket of the roof loop and would have impaired function relative to Ala-Cpn10, similar to Cpn10-Δ-Nterm or Ala-Cpn10-ΔRoof, Gly-Cpn10 or X-Cpn10 (see FIG. 1). Surprisingly, this was not the case. In fact the substitution of the larger bulkier amino acids Pro, Ser or Met at the N-terminal actually resulted in an improved binding of CpG-ODN, and would therefore be expected to enhance the suppression of PRR signalling.

Serine is a small amino acid differing from alanine by a single oxygen molecule in the side chain $CH_2$—OH (instead of —$CH_3$). The placement of serine at the N-terminal is the structurally most similar to Ala-Cpn10 and could be expected to be of a suitable size to incorrectly fit into the pocket and impair binding to CpG-ODN in a manner similar to Gly-Cpn10. However, this may not be not the case, and the Thornton database predicted that Ser is unable to bind to the Lys53Lys55 side chain and cannot form any significant clustering at all. However, it is predicted to be able to bind and form significant clustering geometries with either Gly57, Glu58, Ile59, Gln60, Pro61 and Val62 at the other end of the roof loop to Lys53Lys55.

Proline is unusual in that it has a side chain $CH_2$—$CH_2$—$CH_2$ that forms a ring with the primary N of the amino acid backbone. Thus, its side chain is bulky and might be considered to block the pocket. However, this may not be the case, as the Thornton database predicts that Pro is unable to bind to the Lys53Lys55 side chain. However, it is predicted to able to bind and form significant clustering geometries with either Gly57, Glu58, Ile59, Pro61 and Val62 at the other end of the roof loop to Lys53Lys55.

Methionine has a large side chain $CH_2$—$CH_2$—S—$CH_3$ and an examination of the side chain interactions (Thornton) revealed that an N-terminal methionine is predicted to be unable to form any cluster with Lys53Lys55. However, methionine is predicted to form multiple interactions with Isoleucine59 (Ile59) or Valine 62 (Val62) that are located in the roof loop.

It was interesting to note that there are differences in the ability of the mutants with a methionine at the N-terminal position to bind CpG-ODN depending on which amino acid follows it. It is postulated that this difference is due to additional side chain interactions of these amino acids following the Met with those in the roof loop surrounding either Ile59 or Val62.

It is proposed these amino acids actually bind to the roof loop outside of the pocket, as they may be unable to bind to the side chains of Lys53Lys55 and fit into the pocket. This binding in turn may cause a different conformational change to the roof loop, and the molecule as a whole, thus enabling the tighter binding of CpG-ODN and enhancing immunomodulation over Ala-Cpn10.

The invention claimed is:

1. An isolated chaperonin 10 (Cpn10) variant polypeptide derived from human Cpn10 sharing at least 90% sequence identity with a wild-type human Cpn10 polypeptide and comprising an N-terminus extended by two to five additional amino acid residues compared to said wild-type polypeptide, wherein the polypeptide has increased binding affinity for a pathogen-associated molecular pattern (PAMP) compared to the binding affinity of Ala-Cpn10 (SEQ ID NO: 3) for said PAMP, wherein the isolated Cpn10 polypeptide possesses a conserved core antiparallel β-barrel flanked by a β-hairpin roof loop region and a mobile loop region.

2. The isolated human Cpn10 variant polypeptide of claim 1, wherein the N-terminus of said human variant polypeptide commences with a methionine residue.

3. The isolated human Cpn10 variant polypeptide of claim 2, wherein said methionine residue precedes an amino acid residue selected from the group consisting of arginine, asparagine, aspartic acid, cysteine, glutamic acid, glutamine, histidine, isoleucine, leucine, lysine, methionine, phenylalanine, threonine, tryptophan, tyrosine, and valine.

4. An isolated chaperonin 10 (Cpn10) variant polypeptide sharing at least 90% sequence identity with a wild-type Cpn10 polypeptide and comprising an N-terminus extended by at least two additional amino acid residues compared to said wild-type polypeptide, wherein the polypeptide has increased binding affinity for a pathogen-associated molecular pattern (PAMP) compared to the binding affinity of Ala-Cpn10 (SEQ ID NO: 3) for said PAMP, wherein the N-terminus of said variant polypeptide commences with a methionine residue, and wherein said methionine residue precedes an amino acid residue selected from the group consisting of arginine, asparagine, aspartic acid, cysteine, glutamic acid, glutamine, histidine, isoleucine, leucine, lysine, methionine, phenylalanine, threonine, tryptophan, tyrosine, and valine, wherein said polypeptide comprises the amino acid sequence as set forth in SEQ ID NOs: 29.

5. The isolated Cpn10 variant polypeptide of claim 1, wherein said polypeptide comprises the amino acid sequence as set forth in any one of SEQ ID NOs: 52, 55, 60, 81, 84, 87, or 96.

6. An isolated human chaperonin 10 (Cpn10) variant polypeptide sharing at least 80% sequence identity with a wild-type human Cpn10 polypeptide and comprising an N-terminus extended by one additional amino acid residue compared to said wild-type human polypeptide, wherein said additional amino acid residue is a serine or proline residue, and wherein said variant polypeptide has increased immunomodulatory function compared to human Ala-Cpn10, wherein the isolated Cpn10 polypeptide possesses a conserved core antiparallel β-barrel flanked by a β-hairpin roof loop region and a mobile loop region.

7. An isolated human Cpn10 variant polypeptide sharing at least 80% sequence identity with a wild-type human Cpn10 polypeptide and comprising an N-terminus extended by one additional amino acid residue compared to said wild-type human polypeptide, wherein said additional amino acid residue is a serine or proline residue, and wherein said variant polypeptide has increased immunomodulatory function compared to human Ala-Cpn10, wherein the isolated Cpn10 polypeptide possesses a core antiparallel β-barrel flanked by a β-hairpin roof loop region and a mobile loop region, wherein said polypeptide comprises the amino acid sequence as set forth in SEQ ID NO: 21 or 35.

8. A pharmaceutical composition comprising the polypeptide of claim 1 and a pharmaceutically acceptable excipient, diluent or carrier.

9. A method for treating an inflammatory disease in a subject wherein the inflammatory disease is selected from the group consisting of rheumatoid arthritis and psoriasis, said method comprising administering to the subject a therapeutically effective amount of the polypeptide of claim 1.

10. The isolated variant Cpn10 polypeptide of claim 1 wherein the N-terminus is extended by two to three amino acids.

11. The isolated variant Cpn10 polypeptide of claim 1 wherein the polypeptide shares at least 95% sequence identity with a wild-type human Cpn10 polypeptide.

12. The isolated variant Cpn10 polypeptide of claim 10 wherein the N-terminus of the polypeptide begins with a methionine residue.

13. The isolated variant Cpn10 polypeptide of claim 12 wherein said methionine residue precedes an amino acid residue selected from the group consisting of arginine, asparagine, aspartic acid, cysteine, glutamic acid, glutamine, histidine, isoleucine, leucine, lysine, methionine, phenylalanine, threonine, tryptophan, tyrosine, and valine.

14. The isolated variant Cpn10 polypeptide of claim 13 wherein said methionine residue precedes an amino acid residue selected from the group consisting of isoleucine, leucine, lysine, phenylalanine, tryptophan, tyrosine, and valine.

15. The isolated variant Cpn10 polypeptide of claim 10 wherein the two to three amino acids extending the amino-terminus are selected from the group consisting of lysine, arginine, and histidine.

16. The isolated variant Cpn10 polypeptide of claim 10 wherein the two to three amino acids extending the amino-terminus are selected from the group consisting of aspartic acid and glutamic acid.

* * * * *

SEQUENCE LISTING

```
<160> NUMBER OF SEQ ID NOS: 98

<210> SEQ ID NO 1
<211> LENGTH: 101
<212> TYPE: PRT
<213> ORGANISM: Artificial Sequence
<220> FEATURE:
<223> OTHER INFORMATION: Synthetic Human Cpn10 produced in E.coli
      without N-terminal acetylation

<400> SEQUENCE: 1

Ala Gly Gln Ala Phe Arg Lys Phe Leu Pro Leu Phe Asp Arg Val Leu
1               5                   10                  15

Val Glu Arg Ser Ala Ala Glu Thr Val Thr Lys Gly Gly Ile Met Leu
            20                  25                  30

Pro Glu Lys Ser Gln Gly Lys Val Leu Gln Ala Thr Val Val Ala Val
        35                  40                  45

Gly Ser Gly Ser Lys Gly Lys Gly Gly Glu Ile Gln Pro Val Ser Val
    50                  55                  60

Lys Val Gly Asp Lys Val Leu Leu Pro Glu Tyr Gly Gly Thr Lys Val
65                  70                  75                  80

Val Leu Asp Asp Lys Asp Tyr Phe Leu Phe Arg Asp Gly Asp Ile Leu
                85                  90                  95

Gly Lys Tyr Val Asp
            100

<210> SEQ ID NO 2
<211> LENGTH: 309
<212> TYPE: DNA
<213> ORGANISM: Artificial Sequence
<220> FEATURE:
<223> OTHER INFORMATION: Synthetic Native cDNA of Human Cpn10
<300> PUBLICATION INFORMATION:
<308> DATABASE ACCESSION NUMBER: GenBank X75821; GI:509780

<400> SEQUENCE: 2
```

-continued

```
atggcaggac aagcgtttag aaagtttctt ccactctttg accgagtatt ggttgaaagg      60
agtgctgctg aaactgtaac caaaggaggc attatgcttc agaaaaatc tcaaggaaaa      120 gtattgcaag caacagtagt cgctgttgga tcgggttcta aaggaaaggg tggagagatt     180
caaccagtta gcgtgaaagt tggagataaa gttcttctcc agaatatgg aggcaccaaa      240 gtagttctag atgacaagga ttatttccta tttagagatg gtgacattct ggaaagtac     300 gtagactga                                                              309
```

<210> SEQ ID NO 3
<211> LENGTH: 102
<212> TYPE: PRT
<213> ORGANISM: Artificial Sequence
<220> FEATURE:
<223> OTHER INFORMATION: Synthetic Homo sapiens (human) Cpn10 with an
      additional N-terminal Alanine residue (Ala-Cpn10)

<400> SEQUENCE: 3

```
Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100
```

<210> SEQ ID NO 4
<211> LENGTH: 312
<212> TYPE: DNA
<213> ORGANISM: Artificial Sequence
<220> FEATURE:
<223> OTHER INFORMATION: Synthetic Native cDNA of Ala-Cpn10

<400> SEQUENCE: 4

```
atggcagcag acaagcgtt tagaaagttt cttccactct ttgaccgagt attggttgaa      60
aggagtgctg ctgaaactgt aaccaaagga ggcattatgc ttccagaaaa atctcaagga     120
aaagtattgc aagcaacagt agtcgctgtt ggatcgggtt ctaaaggaaa gggtggagag     180
attcaaccag ttagcgtgaa agttggagat aaagttcttc tcccagaata tggaggcacc    240
aaagtagttc tagatgacaa ggattatttc ctatttagag atggtgacat tcttggaaag    300
tacgtagact ga                                                         312
```

<210> SEQ ID NO 5
<211> LENGTH: 312
<212> TYPE: DNA
<213> ORGANISM: Artificial Sequence
<220> FEATURE:
<223> OTHER INFORMATION: Synthetic Optimised cDNA of Ala-Cpn10(Gly, Arg
      and stop codons are optimized in the cDNA)

<400> SEQUENCE: 5

```
atggcagcag gccaagcgtt tcgcaagttt cttccactct ttgaccgtgt attggttgaa      60
```

```
cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa agttggcgat aaagttcttc tcccagaata tggtggcacc    240
aaagtagttc tagatgacaa ggattatttc ctatttcgtg atggtgacat tcttggcaag    300
tacgtagact aa                                                        312
```

```
<210> SEQ ID NO 6
<211> LENGTH: 102
<212> TYPE: PRT
<213> ORGANISM: Artificial Sequence
<220> FEATURE:
<223> OTHER INFORMATION: Synthetic Human Cpn10 with an additional
      N-terminal Glycine Residue (Gly-Cpn10)

<400> SEQUENCE: 6
```

```
Gly Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100
```

```
<210> SEQ ID NO 7
<211> LENGTH: 312
<212> TYPE: DNA
<213> ORGANISM: Artificial Sequence
<220> FEATURE:
<223> OTHER INFORMATION: Synthetic Native cDNA of Gly-Cpn10

<400> SEQUENCE: 7
atgggtgcag gacaagcgtt tagaaagttt cttccactct tgaccgagt attggttgaa     60 aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggagat aaagttcttc tcccagaata tggaggcacc    240
aaagtagttc tagatgacaa ggattatttc ctatttagag atggtgacat tcttggaaag    300
tacgtagact ga                                                        312
```

```
<210> SEQ ID NO 8
<211> LENGTH: 312
<212> TYPE: DNA
<213> ORGANISM: Artificial Sequence
<220> FEATURE:
<223> OTHER INFORMATION: Synthetic Optimised cDNA of Gly-Cpn10(all
      codons are optimised in the cDNA)

<400> SEQUENCE: 8
atgggtgcgg gccaggcgtt tcgtaaattt ctgccgctgt ttgatcgtgt gctggttgaa     60
cgtagcgcgg cggaaaccgt gaccaaaggc ggcattatgc tgccggaaaa aagccagggc    120
```

-continued

```
aaagtgctgc aggcgaccgt ggttgcggtt ggcagcggca gcaaaggcaa aggcggcgaa    180
attcagccgg tgagcgtgaa agtgggcgat aaagtgctgc tgccggaata tggcggcacc    240
aaagtggtgc tggatgataa agattatttt ctgttccgcg atggcgatat tctgggcaaa    300
tatgtggatt ga                                                        312
```

<210> SEQ ID NO 9
<211> LENGTH: 103
<212> TYPE: PRT
<213> ORGANISM: Artificial Sequence
<220> FEATURE:
<223> OTHER INFORMATION: Synthetic Human Cpn10 with an additional
      N-terminal Valine (V) residue. The initiation Methionine is not
      removed from this protein. (MV-Cpn10)

<400> SEQUENCE: 9

```
Met Val Ala Gly Gln Ala Phe Arg Lys Phe Leu Pro Leu Phe Asp Arg
1               5                   10                  15

Val Leu Val Glu Arg Ser Ala Ala Glu Thr Val Thr Lys Gly Gly Ile
            20                  25                  30

Met Leu Pro Glu Lys Ser Gln Gly Lys Val Leu Gln Ala Thr Val Val
        35                  40                  45

Ala Val Gly Ser Gly Ser Lys Gly Lys Gly Gly Glu Ile Gln Pro Val
    50                  55                  60

Ser Val Lys Val Gly Asp Lys Val Leu Leu Pro Glu Tyr Gly Gly Thr
65                  70                  75                  80

Lys Val Val Leu Asp Asp Lys Asp Tyr Phe Leu Phe Arg Asp Gly Asp
                85                  90                  95

Ile Leu Gly Lys Tyr Val Asp
            100
```

<210> SEQ ID NO 10
<211> LENGTH: 312
<212> TYPE: DNA
<213> ORGANISM: Artificial Sequence
<220> FEATURE:
<223> OTHER INFORMATION: Synthetic Native cDNA of MV-Cpn10

<400> SEQUENCE: 10

```
atggttgcag gacaagcgtt tagaaagttt cttccactct tgaccgagt attggttgaa     60 aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggagat aaagttcttc tcccagaata tggaggcacc    240
aaagtagttc tagatgacaa ggattatttc ctatttagag atggtgacat tcttggaaag    300
tacgtagact ga                                                        312
```

<210> SEQ ID NO 11
<211> LENGTH: 97
<212> TYPE: PRT
<213> ORGANISM: Artificial Sequence
<220> FEATURE:
<223> OTHER INFORMATION: Synthetic Human Cpn10 lacking the N-terminal
      residues 1-AGQAF-5. The initiation Methionine is not removed from
      this protein (Cpn10-deltaNterm)

<400> SEQUENCE: 11

```
Met Arg Lys Phe Leu Pro Leu Phe Asp Arg Val Leu Val Glu Arg Ser
1               5                   10                  15
```

```
Ala Ala Glu Thr Val Thr Lys Gly Gly Ile Met Leu Pro Glu Lys Ser
             20                  25                  30

Gln Gly Lys Val Leu Gln Ala Thr Val Val Ala Val Gly Ser Gly Ser
         35                  40                  45

Lys Gly Lys Gly Gly Glu Ile Gln Pro Val Ser Val Lys Val Gly Asp
     50                  55                  60

Lys Val Leu Pro Glu Tyr Gly Gly Thr Lys Val Val Leu Asp Asp
 65                  70                  75                  80

Lys Asp Tyr Phe Leu Phe Arg Asp Gly Asp Ile Leu Gly Lys Tyr Val
                 85                  90                  95

Asp

<210> SEQ ID NO 12
<211> LENGTH: 103
<212> TYPE: PRT
<213> ORGANISM: Artificial Sequence
<220> FEATURE:
<223> OTHER INFORMATION: Synthetic Human Cpn10 with an additional
      N-terminal Leucine (L) residue. The initiation Methionine (M) is
      not removed from this protein (ML-Cpn10)

<400> SEQUENCE: 12

Met Leu Ala Gly Gln Ala Phe Arg Lys Phe Leu Pro Leu Phe Asp Arg
 1               5                  10                  15

Val Leu Val Glu Arg Ser Ala Ala Glu Thr Val Thr Lys Gly Gly Ile
             20                  25                  30

Met Leu Pro Glu Lys Ser Gln Gly Lys Val Leu Gln Ala Thr Val Val
         35                  40                  45

Ala Val Gly Ser Gly Ser Lys Gly Lys Gly Gly Glu Ile Gln Pro Val
     50                  55                  60

Ser Val Lys Val Gly Asp Lys Val Leu Leu Pro Glu Tyr Gly Gly Thr
 65                  70                  75                  80

Lys Val Val Leu Asp Asp Lys Asp Tyr Phe Leu Phe Arg Asp Gly Asp
                 85                  90                  95

Ile Leu Gly Lys Tyr Val Asp
            100

<210> SEQ ID NO 13
<211> LENGTH: 312
<212> TYPE: DNA
<213> ORGANISM: Artificial Sequence
<220> FEATURE:
<223> OTHER INFORMATION: Synthetic Native cDNA of ML-Cpn10

<400> SEQUENCE: 13
atgctggcag acaagcgtt tagaaagttt cttccactct tgaccgagt attggttgaa      60 aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggagat aaagttcttc tcccagaata tggaggcacc    240
aaagtagttc tagatgacaa ggattatttc ctatttagag atggtgacat tcttggaaag    300
tacgtagact ga                                                       312

<210> SEQ ID NO 14
<211> LENGTH: 312
<212> TYPE: DNA
<213> ORGANISM: Artificial Sequence
<220> FEATURE:
<223> OTHER INFORMATION: Synthetic Optimised cDNA of ML-Cpn10(Gly, Arg
``` and stop codons are optimised in the cDNA)

<400> SEQUENCE: 14

```
atgctggcag gccaagcgtt tcgcaagttt cttccactct ttgaccgtgt attggttgaa      60
cgcagtgctg ctgaaactgt aaccaaaggt ggcattatgc ttccagaaaa atctcaaggc     120
aaagtattgc aagcaacagt agtcgctgtt ggctcgggtt ctaaaggtaa gggtggcgag     180
attcaaccag ttagcgtgaa agttggcgat aaagttcttc ccagaata tggtggcacc      240
aaagtagttc tagatgacaa ggattatttc ctatttcgtg atggtgacat tcttggcaag     300
tacgtagact aa                                                         312
```

<210> SEQ ID NO 15
<211> LENGTH: 103
<212> TYPE: PRT
<213> ORGANISM: Artificial Sequence
<220> FEATURE:
<223> OTHER INFORMATION: Synthetic Human Cpn10 with an additional
      N-terminal Isoleucine (I)residue. The initiation Methionine (M) is
      not removed from this protein (MI Cpn10)

<400> SEQUENCE: 15

Met Ile Ala Gly Gln Ala Phe Arg Lys Phe Leu Pro Leu Phe Asp Arg
1               5                   10                  15

Val Leu Val Glu Arg Ser Ala Ala Glu Thr Val Thr Lys Gly Gly Ile
            20                  25                  30

Met Leu Pro Glu Lys Ser Gln Gly Lys Val Leu Gln Ala Thr Val Val
        35                  40                  45

Ala Val Gly Ser Gly Ser Lys Gly Lys Gly Gly Glu Ile Gln Pro Val
    50                  55                  60

Ser Val Lys Val Gly Asp Lys Val Leu Leu Pro Glu Tyr Gly Gly Thr
65                  70                  75                  80

Lys Val Val Leu Asp Asp Lys Asp Tyr Phe Leu Phe Arg Asp Gly Asp
                85                  90                  95

Ile Leu Gly Lys Tyr Val Asp
            100

<210> SEQ ID NO 16
<211> LENGTH: 312
<212> TYPE: DNA
<213> ORGANISM: Artificial Sequence
<220> FEATURE:
<223> OTHER INFORMATION: Synthetic Native cDNA of MI-Cpn10

<400> SEQUENCE: 16

```
atgattgcag acaagcgtt tagaaagttt cttccactct ttgaccgagt attggttgaa      60
aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggagat aaagttcttc ccagaata tggaggcacc     240
aaagtagttc tagatgacaa ggattatttc ctatttagag atggtgacat tcttggaaag    300
tacgtagact ga                                                         312
```

<210> SEQ ID NO 17
<211> LENGTH: 312
<212> TYPE: DNA
<213> ORGANISM: Artificial Sequence
<220> FEATURE:
<223> OTHER INFORMATION: Synthetic Optimised cDNA of MI-Cpn10(Gly, Arg
      and stop codons are Optimized in the cDNA

<400> SEQUENCE: 17

```
atgattgcag gccaagcgtt tcgcaagttt cttccactct ttgaccgtgt attggttgaa    60
cgcagtgctg ctgaaactgt aaccaaaggt ggcattatgc ttccagaaaa atctcaaggc   120
aaagtattgc aagcaacagt agtcgctgtt ggctcgggtt ctaaaggtaa gggtggcgag   180
attcaaccag ttagcgtgaa agttggcgat aaagttcttc tcccagaata tggtggcacc   240
aaagtagttc tagatgacaa ggattatttc ctatttcgtg atggtgacat tcttggcaag   300
tacgtagact aa                                                       312
```

<210> SEQ ID NO 18
<211> LENGTH: 103
<212> TYPE: PRT
<213> ORGANISM: Artificial Sequence
<220> FEATURE:
<223> OTHER INFORMATION: Synthetic Human Cpn10 with an additional
      N-terminal Histidine (H) residue. The initiation Methionine (M) is
      not removed from this protein (MH-Cpn10)

<400> SEQUENCE: 18

```
Met His Ala Gly Gln Ala Phe Arg Lys Phe Leu Pro Leu Phe Asp Arg
1               5                  10                  15

Val Leu Val Glu Arg Ser Ala Ala Glu Thr Val Thr Lys Gly Gly Ile
            20                  25                  30

Met Leu Pro Glu Lys Ser Gln Gly Lys Val Leu Gln Ala Thr Val Val
        35                  40                  45

Ala Val Gly Ser Gly Ser Lys Gly Lys Gly Gly Glu Ile Gln Pro Val
    50                  55                  60

Ser Val Lys Val Gly Asp Lys Val Leu Leu Pro Glu Tyr Gly Gly Thr
65                  70                  75                  80

Lys Val Val Leu Asp Asp Lys Asp Tyr Phe Leu Phe Arg Asp Gly Asp
                85                  90                  95

Ile Leu Gly Lys Tyr Val Asp
            100
```

<210> SEQ ID NO 19
<211> LENGTH: 312
<212> TYPE: DNA
<213> ORGANISM: Artificial Sequence
<220> FEATURE:
<223> OTHER INFORMATION: Synthetic Native cDNA of MH-Cpn10

<400> SEQUENCE: 19

```
atgcatgcag gacaagcgtt tagaaagttt cttccactct ttgaccgagt attggttgaa    60
aggagtgctg ctgaaactgt aaccaaagga ggcattatgc ttccagaaaa atctcaagga   120
aaagtattgc aagcaacagt agtcgctgtt ggatcgggtt ctaaaggaaa gggtggagag   180
attcaaccag ttagcgtgaa agttggagat aaagttcttc tcccagaata tggaggcacc   240
aaagtagttc tagatgacaa ggattatttc ctatttagag atggtgacat tcttggaaag   300
tacgtagact ga                                                       312
```

<210> SEQ ID NO 20
<211> LENGTH: 312
<212> TYPE: DNA
<213> ORGANISM: Artificial Sequence
<220> FEATURE:
<223> OTHER INFORMATION: Synthetic Optimised cDNA of MH-Cpn10(Gly, Arg
      and stop codons are optimised in the cDNA)

<400> SEQUENCE: 20

```
atgcatgcag gccaagcgtt tcgcaagttt cttccactct tgaccgtgt attggttgaa      60
cgcagtgctg ctgaaactgt aaccaaaggt ggcattatgc ttccagaaaa atctcaaggc     120
aaagtattgc aagcaacagt agtcgctgtt ggctcgggtt ctaaaggtaa gggtggcgag     180
attcaaccag ttagcgtgaa agttggcgat aaagttcttc tcccagaata tggtggcacc     240
aaagtagttc tagatgacaa ggattatttc ctatttcgtg atggtgacat tcttggcaag     300
tacgtagact aa                                                         312
```

<210> SEQ ID NO 21
<211> LENGTH: 102
<212> TYPE: PRT
<213> ORGANISM: Artificial Sequence
<220> FEATURE:
<223> OTHER INFORMATION: Synthetic Human Cpn10 with an additional
    N-terminal Proline (P) residue (P-Cpn10)

<400> SEQUENCE: 21

```
Pro Ala Gly Gln Ala Phe Arg Lys Phe Leu Pro Leu Phe Asp Arg Val
1               5                   10                  15
Leu Val Glu Arg Ser Ala Ala Glu Thr Val Thr Lys Gly Gly Ile Met
            20                  25                  30
Leu Pro Glu Lys Ser Gln Gly Lys Val Leu Gln Ala Thr Val Val Ala
        35                  40                  45
Val Gly Ser Gly Ser Lys Gly Lys Gly Gly Glu Ile Gln Pro Val Ser
    50                  55                  60
Val Lys Val Gly Asp Lys Val Leu Leu Pro Glu Tyr Gly Gly Thr Lys
65                  70                  75                  80
Val Val Leu Asp Asp Lys Asp Tyr Phe Leu Phe Arg Asp Gly Asp Ile
                85                  90                  95
Leu Gly Lys Tyr Val Asp
            100
```

<210> SEQ ID NO 22
<211> LENGTH: 312
<212> TYPE: DNA
<213> ORGANISM: Artificial Sequence
<220> FEATURE:
<223> OTHER INFORMATION: Synthetic Native cDNA of P-Cpn10

<400> SEQUENCE: 22

```
atgccggcag gacaagcgtt tagaaagttt cttccactct tgaccgagt attggttgaa      60
aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggagat aaagttcttc tcccagaata tggaggcacc    240
aaagtagttc tagatgacaa ggattatttc ctatttagag atggtgacat tcttggaaag    300
tacgtagact ga                                                         312
```

<210> SEQ ID NO 23
<211> LENGTH: 312
<212> TYPE: DNA
<213> ORGANISM: Artificial Sequence
<220> FEATURE:
<223> OTHER INFORMATION: Synthetic Optimised cDNA of P-Cpn10(Gly, Arg
    and stop codons are optimized in the cDNA)

<400> SEQUENCE: 23

```
atgccggcag gccaagcgtt tcgcaagttt cttccactct ttgaccgtgt attggttgaa      60
cgcagtgctg ctgaaactgt aaccaaaggt ggcattatgc ttccagaaaa atctcaaggc     120
aaagtattgc aagcaacagt agtcgctgtt ggctcgggtt ctaaaggtaa gggtggcgag     180
attcaaccag ttagcgtgaa agttggcgat aaagttcttc ccagaata tggtggcacc      240 aaagtagttc tagatgacaa ggattatttc ctatttcgtg atggtgacat tcttggcaag     300
tacgtagact aa                                                         312
```

<210> SEQ ID NO 24
<211> LENGTH: 103
<212> TYPE: PRT
<213> ORGANISM: Artificial Sequence
<220> FEATURE:
<223> OTHER INFORMATION: Synthetic Human Cpn10 with an additional
      N-terminal Phenylalanine (F) residue. The initiation Methionine is
      not removed from this protein. (MF-Cpn10)

<400> SEQUENCE: 24

```
Met Phe Ala Gly Gln Ala Phe Arg Lys Phe Leu Pro Leu Phe Asp Arg
1               5                   10                  15

Val Leu Val Glu Arg Ser Ala Ala Glu Thr Val Thr Lys Gly Gly Ile
            20                  25                  30

Met Leu Pro Glu Lys Ser Gln Gly Lys Val Leu Gln Ala Thr Val Val
        35                  40                  45

Ala Val Gly Ser Gly Ser Lys Gly Lys Gly Gly Glu Ile Gln Pro Val
    50                  55                  60

Ser Val Lys Val Gly Asp Lys Val Leu Leu Pro Glu Tyr Gly Gly Thr
65                  70                  75                  80

Lys Val Val Leu Asp Asp Lys Asp Tyr Phe Leu Phe Arg Asp Gly Asp
                85                  90                  95

Ile Leu Gly Lys Tyr Val Asp
            100
```

<210> SEQ ID NO 25
<211> LENGTH: 312
<212> TYPE: DNA
<213> ORGANISM: Artificial Sequence
<220> FEATURE:
<223> OTHER INFORMATION: Synthetic Native cDNA of MF-Cpn10

<400> SEQUENCE: 25

```
atgttcgcag gacaagcgtt tagaaagttt cttccactct ttgaccgagt attggttgaa      60
aggagtgctg ctgaaactgt aaccaaagga ggcattatgc ttccagaaaa atctcaagga     120
aaagtattgc aagcaacagt agtcgctgtt ggatcgggtt ctaaaggaaa gggtggagag     180
attcaaccag ttagcgtgaa agttggagat aaagttcttc ccagaata tggaggcacc      240 aaagtagttc tagatgacaa ggattatttc ctatttagag atggtgacat tcttggaaag     300
tacgtagact ga                                                         312
```

<210> SEQ ID NO 26
<211> LENGTH: 103
<212> TYPE: PRT
<213> ORGANISM: Artificial Sequence
<220> FEATURE:
<223> OTHER INFORMATION: Synthetic Human Cpn10 with an additional
      N-terminal Tyrosine (Y) residue. The initiation Methionine (M) is
      not removed from this protein (MY-Cpn10)

<400> SEQUENCE: 26

Met Tyr Ala Gly Gln Ala Phe Arg Lys Phe Leu Pro Leu Phe Asp Arg
1               5                   10                  15

Val Leu Val Glu Arg Ser Ala Ala Glu Thr Val Thr Lys Gly Gly Ile
            20                  25                  30

Met Leu Pro Glu Lys Ser Gln Gly Lys Val Leu Gln Ala Thr Val Val
        35                  40                  45

Ala Val Gly Ser Gly Ser Lys Gly Lys Gly Gly Glu Ile Gln Pro Val
    50                  55                  60

Ser Val Lys Val Gly Asp Lys Val Leu Leu Pro Glu Tyr Gly Gly Thr
65                  70                  75                  80

Lys Val Val Leu Asp Asp Lys Asp Tyr Phe Leu Phe Arg Asp Gly Asp
                85                  90                  95

Ile Leu Gly Lys Tyr Val Asp
            100

<210> SEQ ID NO 27
<211> LENGTH: 312
<212> TYPE: DNA
<213> ORGANISM: Artificial Sequence
<220> FEATURE:
<223> OTHER INFORMATION: Synthetic Native cDNA of MY-Cpn10

<400> SEQUENCE: 27
atgtatgcag acaagcgtt tagaaagttt cttccactct tgaccgagt attggttgaa      60 aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggagat aaagttcttc tcccagaata tggaggcacc    240
aaagtagttc tagatgacaa ggattatttc ctatttagag atggtgacat tcttggaaag    300
tacgtagact ga                                                        312

<210> SEQ ID NO 28
<211> LENGTH: 312
<212> TYPE: DNA
<213> ORGANISM: Artificial Sequence
<220> FEATURE:
<223> OTHER INFORMATION: Synthetic Optimised cDNA of MY-Cpn10(Gly, Arg
      and stop codons are Optimized in the cDNA)

<400> SEQUENCE: 28
atgtatgcag gccaagcgtt tcgcaagttt cttccactct tgaccgtgt attggttgaa      60 cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa agttggcgat aaagttcttc tcccagaata tggtggcacc    240
aaagtagttc tagatgacaa ggattatttc ctatttcgtg atggtgacat tcttggcaag    300
tacgtagact aa                                                        312

<210> SEQ ID NO 29
<211> LENGTH: 103
<212> TYPE: PRT
<213> ORGANISM: Artificial Sequence
<220> FEATURE:
<223> OTHER INFORMATION: Synthetic Human Cpn10 with an additional
      N-terminal Tryptophan (W) residue. The initiation Methionine (M)
      is not removed from this protein (MW-Cpn10)

<400> SEQUENCE: 29

Met Trp Ala Gly Gln Ala Phe Arg Lys Phe Leu Pro Leu Phe Asp Arg

```
1               5                   10                  15
Val Leu Val Glu Arg Ser Ala Ala Glu Thr Val Thr Lys Gly Gly Ile
            20                  25                  30

Met Leu Pro Glu Lys Ser Gln Gly Lys Val Leu Gln Ala Thr Val Val
        35                  40                  45

Ala Val Gly Ser Gly Ser Lys Gly Lys Gly Gly Glu Ile Gln Pro Val
    50                  55                  60

Ser Val Lys Val Gly Asp Lys Val Leu Leu Pro Glu Tyr Gly Gly Thr
65                  70                  75                  80

Lys Val Val Leu Asp Asp Lys Asp Tyr Phe Leu Phe Arg Asp Gly Asp
                85                  90                  95

Ile Leu Gly Lys Tyr Val Asp
            100

<210> SEQ ID NO 30
<211> LENGTH: 312
<212> TYPE: DNA
<213> ORGANISM: Artificial Sequence
<220> FEATURE:
<223> OTHER INFORMATION: Synthetic Native cDNA of MW-Cpn10

<400> SEQUENCE: 30
atgtgggcag acaagcgtt tagaaagttt cttccactct ttgaccgagt attggttgaa      60
aggagtgctg ctgaaactgt aaccaaagga ggcattatgc ttccagaaaa atctcaagga     120
aaagtattgc aagcaacagt agtcgctgtt ggatcgggtt ctaaaggaaa gggtggagag     180
attcaaccag ttagcgtgaa agttggagat aaagttcttc tcccagaata tggaggcacc     240
aaagtagttc tagatgacaa ggattatttc ctatttagag atggtgacat tcttggaaag     300
tacgtagact ga                                                        312

<210> SEQ ID NO 31
<211> LENGTH: 312
<212> TYPE: DNA
<213> ORGANISM: Artificial Sequence
<220> FEATURE:
<223> OTHER INFORMATION: Synthetic Optimised cDNA of MW-Cpn10(Gly, Arg
      and stop codons are Optimized in the cDNA)

<400> SEQUENCE: 31
atgtgggcag ccaagcgtt tcgcaagttt cttccactct ttgaccgtgt attggttgaa      60
cgcagtgctg ctgaaactgt aaccaaaggt ggcattatgc ttccagaaaa atctcaaggc     120
aaagtattgc aagcaacagt agtcgctgtt ggctcgggtt ctaaaggtaa gggtggcgag     180
attcaaccag ttagcgtgaa agttggcgat aaagttcttc tcccagaata tggtggcacc     240
aaagtagttc tagatgacaa ggattatttc ctatttcgtg atggtgacat tcttggcaag     300
tacgtagact aa                                                        312

<210> SEQ ID NO 32
<211> LENGTH: 103
<212> TYPE: PRT
<213> ORGANISM: Artificial Sequence
<220> FEATURE:
<223> OTHER INFORMATION: Synthetic Human Cpn10 with an additional
      N-terminal Cysteine (C) residue. The initiation Methionine (M) is
      not removed from this protein(MC-Cpn10)

<400> SEQUENCE: 32

Met Cys Ala Gly Gln Ala Phe Arg Lys Phe Leu Pro Leu Phe Asp Arg
1               5                   10                  15
```

```
Val Leu Val Glu Arg Ser Ala Ala Glu Thr Val Thr Lys Gly Gly Ile
            20                  25                  30

Met Leu Pro Glu Lys Ser Gln Gly Lys Val Leu Gln Ala Thr Val Val
        35                  40                  45

Ala Val Gly Ser Gly Ser Lys Gly Lys Gly Gly Glu Ile Gln Pro Val
    50                  55                  60

Ser Val Lys Val Gly Asp Lys Val Leu Leu Pro Glu Tyr Gly Gly Thr
65                  70                  75                  80

Lys Val Val Leu Asp Asp Lys Asp Tyr Phe Leu Phe Arg Asp Gly Asp
                85                  90                  95

Ile Leu Gly Lys Tyr Val Asp
            100
```

<210> SEQ ID NO 33
<211> LENGTH: 312
<212> TYPE: DNA
<213> ORGANISM: Artificial Sequence
<220> FEATURE:
<223> OTHER INFORMATION: Synthetic Native cDNA of MC-Cpn10

<400> SEQUENCE: 33

```
atgtgcgcag gacaagcgtt tagaaagttt cttccactct tgaccgagt attggttgaa      60 aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggagat aaagttcttc tcccagaata tggaggcacc    240
aaagtagttc tagatgacaa ggattatttc ctatttagag atggtgacat tcttggaaag    300
tacgtagact ga                                                        312
```

<210> SEQ ID NO 34
<211> LENGTH: 312
<212> TYPE: DNA
<213> ORGANISM: Artificial Sequence
<220> FEATURE:
<223> OTHER INFORMATION: Synthetic Optimised cDNA of MC-Cpn10(Gly, Arg
      and stop codons are Optimized in the cDNA)

<400> SEQUENCE: 34

```
atgtgcgcag gccaagcgtt tcgcaagttt cttccactct tgaccgtgt attggttgaa       60 cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa agttggcgat aaagttcttc tcccagaata tggtggcacc    240
aaagtagttc tagatgacaa ggattatttc ctatttcgtg atggtgacat tcttggcaag    300
tacgtagact aa                                                        312
```

<210> SEQ ID NO 35
<211> LENGTH: 102
<212> TYPE: PRT
<213> ORGANISM: Artificial Sequence
<220> FEATURE:
<223> OTHER INFORMATION: Synthetic Human Cpn10 with an additional
      N-terminal Serine (S) residue (S-Cpn10)

<400> SEQUENCE: 35

```
Ser Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
```

```
                    20                  25                  30

Leu Pro Glu Lys Ser Gln Gly Lys Val Leu Gln Ala Thr Val Ala
            35                  40                  45

Val Gly Ser Gly Ser Lys Gly Lys Gly Gly Glu Ile Gln Pro Val Ser
        50                  55                  60

Val Lys Val Gly Asp Lys Val Leu Leu Pro Glu Tyr Gly Gly Thr Lys
 65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 36
<211> LENGTH: 312
<212> TYPE: DNA
<213> ORGANISM: Artificial Sequence
<220> FEATURE:
<223> OTHER INFORMATION: Synthetic Native cDNA of S-Cpn10

<400> SEQUENCE: 36
atgagcgcag acaagcgtt tagaaagttt cttccactct tgaccgagt attggttgaa      60 aggagtgctg ctgaaactgt aaccaaagga ggcattatgc ttccagaaaa atctcaagga   120
aaagtattgc aagcaacagt agtcgctgtt ggatcgggtt ctaaaggaaa gggtggagag   180
attcaaccag ttagcgtgaa agttggagat aaagttcttc tcccagaata tggaggcacc   240
aaagtagttc tagatgacaa ggattatttc ctatttagag atggtgacat tcttggaaag   300
tacgtagact ga                                                       312

<210> SEQ ID NO 37
<211> LENGTH: 312
<212> TYPE: DNA
<213> ORGANISM: Artificial Sequence
<220> FEATURE:
<223> OTHER INFORMATION: Synthetic Optimised cDNA of S-Cpn10 (Gly, Arg
      and stop codons are Optimized in the cDNA)

<400> SEQUENCE: 37
atgagcgcag gccaagcgtt tcgcaagttt cttccactct tgaccgtgt attggttgaa      60 cgcagtgctg ctgaaactgt aaccaaaggt ggcattatgc ttccagaaaa atctcaaggc   120
aaagtattgc aagcaacagt agtcgctgtt ggctcgggtt ctaaaggtaa gggtggcgag   180
attcaaccag ttagcgtgaa agttggcgat aaagttcttc tcccagaata tggtggcacc   240
aaagtagttc tagatgacaa ggattatttc ctatttcgtg atggtgacat tcttggcaag   300
tacgtagact aa                                                       312

<210> SEQ ID NO 38
<211> LENGTH: 103
<212> TYPE: PRT
<213> ORGANISM: Artificial Sequence
<220> FEATURE:
<223> OTHER INFORMATION: Synthetic Human Cpn10 with an additional
      N-terminal Threonine (T) residue. The initiation Methionine (M) is
      not removed from this protein (MT-Cpn10)

<400> SEQUENCE: 38

Met Thr Ala Gly Gln Ala Phe Arg Lys Phe Leu Pro Leu Phe Asp Arg
 1               5                  10                  15

Val Leu Val Glu Arg Ser Ala Ala Glu Thr Val Thr Lys Gly Gly Ile
                20                  25                  30
```

Met Leu Pro Glu Lys Ser Gln Gly Lys Val Leu Gln Ala Thr Val Val
         35                  40                  45

Ala Val Gly Ser Gly Ser Lys Gly Lys Gly Gly Glu Ile Gln Pro Val
 50                  55                  60

Ser Val Lys Val Gly Asp Lys Val Leu Leu Pro Glu Tyr Gly Gly Thr
 65                  70                  75                  80

Lys Val Val Leu Asp Asp Lys Asp Tyr Phe Leu Phe Arg Asp Gly Asp
                 85                  90                  95

Ile Leu Gly Lys Tyr Val Asp
            100

<210> SEQ ID NO 39
<211> LENGTH: 312
<212> TYPE: DNA
<213> ORGANISM: Artificial Sequence
<220> FEATURE:
<223> OTHER INFORMATION: Synthetic Native cDNA of MT-Cpn10

<400> SEQUENCE: 39
atgaccgcag acaagcgtt tagaaagttt cttccactct tgaccgagt attggttgaa      60 aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccga ttagcgtgaa agttggagat aaagttcttc tcccagaata tggaggcacc    240
aaagtagttc tagatgacaa ggattatttc ctatttagag atggtgacat tcttggaaag    300
tacgtagact ga                                                        312

<210> SEQ ID NO 40
<211> LENGTH: 312
<212> TYPE: DNA
<213> ORGANISM: Artificial Sequence
<220> FEATURE:
<223> OTHER INFORMATION: Synthetic Optimised cDNA of MT-Cpn10 (Gly, Arg
      and stop codons are Optimized in the cDNA)

<400> SEQUENCE: 40
atgaccgcag gccaagcgtt tcgcaagttt cttccactct tgaccgtgt attggttgaa      60 cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa agttggcgat aaagttcttc tcccagaata tggtggcacc    240
aaagtagttc tagatgacaa ggattatttc ctatttcgtg atggtgacat tcttggcaag    300
tacgtagact aa                                                        312

<210> SEQ ID NO 41
<211> LENGTH: 103
<212> TYPE: PRT
<213> ORGANISM: Artificial Sequence
<220> FEATURE:
<223> OTHER INFORMATION: Synthetic Human Cpn10 with an additional
      N-terminal Aspartate (D) residue. The initiation Methionine (M) is
      not removed from this protein (MD-Cpn10)

<400> SEQUENCE: 41

Met Asp Ala Gly Gln Ala Phe Arg Lys Phe Leu Pro Leu Phe Asp Arg
 1               5                  10                  15

Val Leu Val Glu Arg Ser Ala Ala Glu Thr Val Thr Lys Gly Gly Ile
                 20                  25                  30

Met Leu Pro Glu Lys Ser Gln Gly Lys Val Leu Gln Ala Thr Val Val
                35                  40                  45

Ala Val Gly Ser Gly Ser Lys Gly Lys Gly Gly Glu Ile Gln Pro Val
    50                  55                  60

Ser Val Lys Val Gly Asp Lys Val Leu Leu Pro Glu Tyr Gly Gly Thr
65                  70                  75                  80

Lys Val Val Leu Asp Asp Lys Asp Tyr Phe Leu Phe Arg Asp Gly Asp
                85                  90                  95

Ile Leu Gly Lys Tyr Val Asp
            100

<210> SEQ ID NO 42
<211> LENGTH: 312
<212> TYPE: DNA
<213> ORGANISM: Artificial Sequence
<220> FEATURE:
<223> OTHER INFORMATION: Synthetic Native cDNA of MD-Cpn10

<400> SEQUENCE: 42
atggatgcag acaagcgtt tagaaagttt cttccactct tgaccgagt attggttgaa      60 aggagtgctg ctgaaactgt aaccaaagga ggcattatgc ttccagaaaa atctcaagga   120
aaagtattgc aagcaacagt agtcgctgtt ggatcgggtt ctaaaggaaa gggtggagag   180
attcaaccag ttagcgtgaa agttggagat aaagttcttc tcccagaata tggaggcacc   240
aaagtagttc tagatgacaa ggattatttc ctatttagag atggtgacat tcttggaaag   300
tacgtagact ga                                                        312

<210> SEQ ID NO 43
<211> LENGTH: 312
<212> TYPE: DNA
<213> ORGANISM: Artificial Sequence
<220> FEATURE:
<223> OTHER INFORMATION: Synthetic Optimised cDNA of MD-Cpn10(Gly, Arg
      and stop codons are optimised in the cDNA

<400> SEQUENCE: 43
atggatgcag gccaagcgtt tcgcaagttt cttccactct tgaccgtgt attggttgaa     60 cgcagtgctg ctgaaactgt aaccaaaggt ggcattatgc ttccagaaaa atctcaaggc   120
aaagtattgc aagcaacagt agtcgctgtt ggctcgggtt ctaaaggtaa gggtggcgag   180
attcaaccag ttagcgtgaa agttggcgat aaagttcttc tcccagaata tggtggcacc   240
aaagtagttc tagatgacaa ggattatttc ctatttcgtg atggtgacat tcttggcaag   300
tacgtagact aa                                                        312

<210> SEQ ID NO 44
<211> LENGTH: 103
<212> TYPE: PRT
<213> ORGANISM: Artificial Sequence
<220> FEATURE:
<223> OTHER INFORMATION: Synthetic Human Cpn10 with an additional
      N-terminal Asparagine (N) residue. The initiation Methionine (M)
      is not removed from this protein (MN-Cpn10)

<400> SEQUENCE: 44

Met Asn Ala Gly Gln Ala Phe Arg Lys Phe Leu Pro Leu Phe Asp Arg
1               5                   10                  15

Val Leu Val Glu Arg Ser Ala Ala Glu Thr Val Thr Lys Gly Gly Ile
                20                  25                  30

Met Leu Pro Glu Lys Ser Gln Gly Lys Val Leu Gln Ala Thr Val Val

```
            35                  40                  45
Ala Val Gly Ser Gly Ser Lys Gly Lys Gly Gly Glu Ile Gln Pro Val
    50                  55                  60

Ser Val Lys Val Gly Asp Lys Val Leu Leu Pro Glu Tyr Gly Gly Thr
65                  70                  75                  80

Lys Val Val Leu Asp Asp Lys Asp Tyr Phe Leu Phe Arg Asp Gly Asp
                85                  90                  95

Ile Leu Gly Lys Tyr Val Asp
            100

<210> SEQ ID NO 45
<211> LENGTH: 312
<212> TYPE: DNA
<213> ORGANISM: Artificial Sequence
<220> FEATURE:
<223> OTHER INFORMATION: Synthetic Native cDNA of MN-Cpn10

<400> SEQUENCE: 45
atgaacgcag gacaagcgtt tagaaagttt cttccactct tgaccgagt attggttgaa      60 aggagtgctg ctgaaactgt aaccaaagga ggcattatgc ttccagaaaa atctcaagga     120
aaagtattgc aagcaacagt agtcgctgtt ggatcgggtt ctaaaggaaa gggtggagag     180
attcaaccag ttagcgtgaa agttggagat aaagttcttc tcccagaata tggaggcacc     240
aaagtagttc tagatgacaa ggattatttc ctatttagag atggtgacat tcttggaaag     300
tacgtagact ga                                                        312

<210> SEQ ID NO 46
<211> LENGTH: 312
<212> TYPE: DNA
<213> ORGANISM: Artificial Sequence
<220> FEATURE:
<223> OTHER INFORMATION: Synthetic Optimised cDNA of MN-Cpn10 (Gly, Arg
      and stop codons are optimised in the cDNA)

<400> SEQUENCE: 46
atgaacgcag gccaagcgtt tcgcaagttt cttccactct tgaccgtgt attggttgaa      60 cgcagtgctg ctgaaactgt aaccaaaggt ggcattatgc ttccagaaaa atctcaaggc     120
aaagtattgc aagcaacagt agtcgctgtt ggctcgggtt ctaaaggtaa gggtggcgag     180
attcaaccag ttagcgtgaa agttggcgat aaagttcttc tcccagaata tggtggcacc     240
aaagtagttc tagatgacaa ggattatttc ctatttcgtg atggtgacat tcttggcaag     300
tacgtagact aa                                                        312

<210> SEQ ID NO 47
<211> LENGTH: 103
<212> TYPE: PRT
<213> ORGANISM: Artificial Sequence
<220> FEATURE:
<223> OTHER INFORMATION: Synthetic Human Cpn10 with an additional
      N-terminal Glutamate (E) Residues. The initiation Methionine is
      not removed from this protein (ME-Cpn10)

<400> SEQUENCE: 47

Met Glu Ala Gly Gln Ala Phe Arg Lys Phe Leu Pro Leu Phe Asp Arg
1               5                   10                  15

Val Leu Val Glu Arg Ser Ala Ala Glu Thr Val Thr Lys Gly Gly Ile
            20                  25                  30

Met Leu Pro Glu Lys Ser Gln Gly Lys Val Leu Gln Ala Thr Val Val
        35                  40                  45
```

```
Ala Val Gly Ser Gly Ser Lys Gly Lys Gly Gly Glu Ile Gln Pro Val
        50                  55                  60

Ser Val Lys Val Gly Asp Lys Val Leu Leu Pro Glu Tyr Gly Gly Thr
65                  70                  75                  80

Lys Val Val Leu Asp Asp Lys Asp Tyr Phe Leu Phe Arg Asp Gly Asp
                85                  90                  95

Ile Leu Gly Lys Tyr Val Asp
            100

<210> SEQ ID NO 48
<211> LENGTH: 312
<212> TYPE: DNA
<213> ORGANISM: Artificial Sequence
<220> FEATURE:
<223> OTHER INFORMATION: Synthetic Native cDNA of ME-Cpn10

<400> SEQUENCE: 48
atggaagcag acaagcgtt tagaaagttt cttccactct tgaccgagt attggttgaa      60 aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggagat aaagttcttc tcccagaata tggaggcacc    240
aaagtagttc tagatgacaa ggattatttc ctatttagag atggtgacat tcttggaaag    300
tacgtagact ga                                                        312

<210> SEQ ID NO 49
<211> LENGTH: 103
<212> TYPE: PRT
<213> ORGANISM: Artificial Sequence
<220> FEATURE:
<223> OTHER INFORMATION: Synthetic Human Cpn10 with an additional
      N-terminal Glutamine (Q) residue. The initiation Methionine (M) is
      not removed from this protein (MQ-Cpn10)

<400> SEQUENCE: 49

Met Gln Ala Gly Gln Ala Phe Arg Lys Phe Leu Pro Leu Phe Asp Arg
1               5                   10                  15

Val Leu Val Glu Arg Ser Ala Ala Glu Thr Val Thr Lys Gly Gly Ile
            20                  25                  30

Met Leu Pro Glu Lys Ser Gln Gly Lys Val Leu Gln Ala Thr Val Val
        35                  40                  45

Ala Val Gly Ser Gly Ser Lys Gly Lys Gly Gly Glu Ile Gln Pro Val
    50                  55                  60

Ser Val Lys Val Gly Asp Lys Val Leu Leu Pro Glu Tyr Gly Gly Thr
65                  70                  75                  80

Lys Val Val Leu Asp Asp Lys Asp Tyr Phe Leu Phe Arg Asp Gly Asp
                85                  90                  95

Ile Leu Gly Lys Tyr Val Asp
            100

<210> SEQ ID NO 50
<211> LENGTH: 312
<212> TYPE: DNA
<213> ORGANISM: Artificial Sequence
<220> FEATURE:
<223> OTHER INFORMATION: Synthetic Native cDNA of MQ-Cpn10

<400> SEQUENCE: 50
atgcaggcag acaagcgtt tagaaagttt cttccactct tgaccgagt attggttgaa      60
```

```
aggagtgctg ctgaaactgt aaccaaagga ggcattatgc ttccagaaaa atctcaagga    120
aaagtattgc aagcaacagt agtcgctgtt ggatcgggtt ctaaaggaaa gggtggagag    180
attcaaccag ttagcgtgaa agttggagat aaagttcttc tcccagaata tggaggcacc    240
aaagtagttc tagatgacaa ggattatttc ctatttagag atggtgacat tcttggaaag    300
tacgtagact ga                                                        312
```

<210> SEQ ID NO 51
<211> LENGTH: 312
<212> TYPE: DNA
<213> ORGANISM: Artificial Sequence
<220> FEATURE:
<223> OTHER INFORMATION: Synthetic Optimised cDNA of MQ-Cpn10 (Gly, Arg
      and stop codons are optimised in the cDNA)

<400> SEQUENCE: 51

```
atgcaggcag gccaagcgtt tcgcaagttt cttccactct ttgaccgtgt attggttgaa     60
cgcagtgctg ctgaaactgt aaccaaaggt ggcattatgc ttccagaaaa atctcaaggc    120
aaagtattgc aagcaacagt agtcgctgtt ggctcgggtt ctaaaggtaa gggtggcgag    180
attcaaccag ttagcgtgaa agttggcgat aaagttcttc tcccagaata tggtggcacc    240
aaagtagttc tagatgacaa ggattatttc ctatttcgtg atggtgacat tcttggcaag    300
tacgtagact aa                                                        312
```

<210> SEQ ID NO 52
<211> LENGTH: 103
<212> TYPE: PRT
<213> ORGANISM: Artificial Sequence
<220> FEATURE:
<223> OTHER INFORMATION: Synthetic Human Cpn10 with two additional
      N-terminal Alanine (A) residues (AA-Cpn10)

<400> SEQUENCE: 52

```
Ala Ala Ala Gly Gln Ala Phe Arg Lys Phe Leu Pro Leu Phe Asp Arg
1               5                   10                  15

Val Leu Val Glu Arg Ser Ala Ala Glu Thr Val Thr Lys Gly Gly Ile
            20                  25                  30

Met Leu Pro Glu Lys Ser Gln Gly Lys Val Leu Gln Ala Thr Val Val
        35                  40                  45

Ala Val Gly Ser Gly Ser Lys Gly Lys Gly Gly Glu Ile Gln Pro Val
    50                  55                  60

Ser Val Lys Val Gly Asp Lys Val Leu Leu Pro Glu Tyr Gly Gly Thr
65                  70                  75                  80

Lys Val Val Leu Asp Asp Lys Asp Tyr Phe Leu Phe Arg Asp Gly Asp
                85                  90                  95

Ile Leu Gly Lys Tyr Val Asp
            100
```

<210> SEQ ID NO 53
<211> LENGTH: 315
<212> TYPE: DNA
<213> ORGANISM: Artificial Sequence
<220> FEATURE:
<223> OTHER INFORMATION: Synthetic Native cDNA of AA-Cpn10

<400> SEQUENCE: 53

```
atggcagcgg caggacaagc gtttagaaag tttcttccac tctttgaccg agtattggtt     60
gaaaggagtg ctgctgaaac tgtaaccaaa ggaggcatta tgcttccaga aaaatctcaa    120
```

```
ggaaaagtat tgcaagcaac agtagtcgct gttggatcgg gttctaaagg aaagggtgga    180
gagattcaac cagttagcgt gaaagttgga gataaagttc ttctcccaga atatggaggc    240
accaaagtag ttctagatga caaggattat ttcctattta gagatggtga cattcttgga    300
aagtacgtag actga                                                    315
```

<210> SEQ ID NO 54
<211> LENGTH: 315
<212> TYPE: DNA
<213> ORGANISM: Artificial Sequence
<220> FEATURE:
<223> OTHER INFORMATION: Synthetic Optimised cDNA of AA-Cpn10 (Gly, Arg
      and stop codons are optimised in the cDNA)

<400> SEQUENCE: 54

```
atggcagcgg caggccaagc gtttcgcaag tttcttccac tctttgaccg tgtattggtt    60
gaacgcagtg ctgctgaaac tgtaaccaaa ggtggcatta tgcttccaga aaaatctcaa   120
ggcaaagtat tgcaagcaac agtagtcgct gttggctcgg gttctaaagg taagggtggc   180
gagattcaac cagttagcgt gaaagttggc gataaagttc ttctcccaga atatggtggc   240
accaaagtag ttctagatga caaggattat ttcctatttc gtgatggtga cattcttggc   300
aagtacgtag actaa                                                    315
```

<210> SEQ ID NO 55
<211> LENGTH: 103
<212> TYPE: PRT
<213> ORGANISM: Artificial Sequence
<220> FEATURE:
<223> OTHER INFORMATION: Synthetic Human Cpn10 with two additional
      N-terminal Glycine (G) residues (GG-Cpn10)

<400> SEQUENCE: 55

```
Gly Gly Ala Gly Gln Ala Phe Arg Lys Phe Leu Pro Leu Phe Asp Arg
1               5                   10                  15

Val Leu Val Glu Arg Ser Ala Ala Glu Thr Val Thr Lys Gly Gly Ile
            20                  25                  30

Met Leu Pro Glu Lys Ser Gln Gly Lys Val Leu Gln Ala Thr Val Val
        35                  40                  45

Ala Val Gly Ser Gly Ser Lys Gly Lys Gly Gly Glu Ile Gln Pro Val
    50                  55                  60

Ser Val Lys Val Gly Asp Lys Val Leu Leu Pro Glu Tyr Gly Gly Thr
65                  70                  75                  80

Lys Val Val Leu Asp Asp Lys Asp Tyr Phe Leu Phe Arg Asp Gly Asp
                85                  90                  95

Ile Leu Gly Lys Tyr Val Asp
            100
```

<210> SEQ ID NO 56
<211> LENGTH: 315
<212> TYPE: DNA
<213> ORGANISM: Artificial Sequence
<220> FEATURE:
<223> OTHER INFORMATION: Synthetic Native cDNA of GG-Cpn10

<400> SEQUENCE: 56

```
atgggcggtg caggacaagc gtttagaaag tttcttccac tctttgaccg agtattggtt    60
gaaaggagtg ctgctgaaac tgtaaccaaa ggaggcatta tgcttccaga aaaatctcaa   120
ggaaaagtat tgcaagcaac agtagtcgct gttggatcgg gttctaaagg aaagggtgga   180
```

```
gagattcaac cagttagcgt gaaagttgga gataaagttc ttctcccaga atatggaggc     240
accaaagtag ttctagatga caaggattat ttcctattta gagatggtga cattcttgga     300
aagtacgtag actga                                                      315
```

<210> SEQ ID NO 57
<211> LENGTH: 315
<212> TYPE: DNA
<213> ORGANISM: Artificial Sequence
<220> FEATURE:
<223> OTHER INFORMATION: Synthetic Optimised cDNA of GG-Cpn10 (Gly, Arg
      and stop codons are optimised in the cDNA)

<400> SEQUENCE: 57

```
atgggcggtg caggccaagc gtttcgcaag tttcttccac tctttgaccg tgtattggtt      60
gaacgcagtg ctgctgaaac tgtaaccaaa ggtggcatta tgcttccaga aaaatctcaa     120
ggcaaagtat tgcaagcaac agtagtcgct gttggctcgg gttctaaagg taagggtggc     180
gagattcaac cagttagcgt gaaagttggc gataaagttc ttctcccaga atatggtggc     240
accaaagtag ttctagatga caaggattat ttcctatttc gtgatggtga cattcttggc     300
aagtacgtag actaa                                                      315
```

<210> SEQ ID NO 58
<211> LENGTH: 104
<212> TYPE: PRT
<213> ORGANISM: Artificial Sequence
<220> FEATURE:
<223> OTHER INFORMATION: Synthetic Human Cpn10 with additional
      N-terminal Glycine (G), Serine (S) + Methionine (M) residues
      respectively (GSM-Cpn10)

<400> SEQUENCE: 58

```
Gly Ser Met Ala Gly Gln Ala Phe Arg Lys Phe Leu Pro Leu Phe Asp
1               5                   10                  15

Arg Val Leu Val Glu Arg Ser Ala Ala Glu Thr Val Thr Lys Gly Gly
            20                  25                  30

Ile Met Leu Pro Glu Lys Ser Gln Gly Lys Val Leu Gln Ala Thr Val
        35                  40                  45

Val Ala Val Gly Ser Gly Ser Lys Gly Lys Gly Gly Glu Ile Gln Pro
    50                  55                  60

Val Ser Val Lys Val Gly Asp Lys Val Leu Leu Pro Glu Tyr Gly Gly
65                  70                  75                  80

Thr Lys Val Val Leu Asp Asp Lys Asp Tyr Phe Leu Phe Arg Asp Gly
                85                  90                  95

Asp Ile Leu Gly Lys Tyr Val Asp
            100
```

<210> SEQ ID NO 59
<211> LENGTH: 318
<212> TYPE: DNA
<213> ORGANISM: Artificial Sequence
<220> FEATURE:
<223> OTHER INFORMATION: Synthetic Native cDNA of GSM-Cpn10

<400> SEQUENCE: 59

```
atgggaagta tggcaggaca agcgtttaga aagtttcttc cactctttga ccgagtattg      60
gttgaaagga gtgctgctga aactgtaacc aaaggaggca ttatgcttcc agaaaaatct     120
caaggaaaag tattgcaagc aacagtagtc gctgttggat cgggttctaa aggaaagggt     180
```

```
ggagagattc aaccagttag cgtgaaagtt ggagataaag ttcttctccc agaatatgga    240
ggcaccaaag tagttctaga tgacaaggat tatttcctat ttagagatgg tgacattctt    300
ggaaagtacg tagactga                                                   318
```

<210> SEQ ID NO 60
<211> LENGTH: 104
<212> TYPE: PRT
<213> ORGANISM: Artificial Sequence
<220> FEATURE:
<223> OTHER INFORMATION: Synthetic Human Cpn10 with three additional
      N-terminal Alanine Residues (AAA-Cpn10)

<400> SEQUENCE: 60

```
Ala Ala Ala Ala Gly Gln Ala Phe Arg Lys Phe Leu Pro Leu Phe Asp
1               5                   10                  15

Arg Val Leu Val Glu Arg Ser Ala Ala Glu Thr Val Thr Lys Gly Gly
            20                  25                  30

Ile Met Leu Pro Glu Lys Ser Gln Gly Lys Val Leu Gln Ala Thr Val
        35                  40                  45

Val Ala Val Gly Ser Gly Ser Lys Gly Lys Gly Gly Glu Ile Gln Pro
    50                  55                  60

Val Ser Val Lys Val Gly Asp Lys Val Leu Leu Pro Glu Tyr Gly Gly
65                  70                  75                  80

Thr Lys Val Val Leu Asp Asp Lys Asp Tyr Phe Leu Phe Arg Asp Gly
                85                  90                  95

Asp Ile Leu Gly Lys Tyr Val Asp
            100
```

<210> SEQ ID NO 61
<211> LENGTH: 318
<212> TYPE: DNA
<213> ORGANISM: Artificial Sequence
<220> FEATURE:
<223> OTHER INFORMATION: Synthetic Native cDNA of AAA-Cpn10

<400> SEQUENCE: 61

```
atggcggcag cggcaggaca agcgtttaga aagtttcttc cactctttga ccgagtattg     60
gttgaaagga gtgctgctga aactgtaacc aaaggaggca ttatgcttcc agaaaaatct    120
caaggaaaag tattgcaagc aacagtagtc gctgttggat cgggttctaa aggaaagggt    180
ggagagattc aaccagttag cgtgaaagtt ggagataaag ttcttctccc agaatatgga    240
ggcaccaaag tagttctaga tgacaaggat tatttcctat ttagagatgg tgacattctt    300
ggaaagtacg tagactga                                                  318
```

<210> SEQ ID NO 62
<211> LENGTH: 318
<212> TYPE: DNA
<213> ORGANISM: Artificial Sequence
<220> FEATURE:
<223> OTHER INFORMATION: Synthetic Optimised cDNA of AAA-Cpn10 (Gly, Arg
      and stop codons are optimised in the cDNA)

<400> SEQUENCE: 62

```
atggcggcag cggcaggcca agcgtttcgc aagtttcttc cactctttga ccgtgtattg     60
gttgaacgca gtgctgctga aactgtaacc aaaggtggca ttatgcttcc agaaaaatct    120
caaggcaaag tattgcaagc aacagtagtc gctgttggct cgggttctaa aggtaagggt    180
ggcgagattc aaccagttag cgtgaaagtt ggcgataaag ttcttctccc agaatatggt    240
```

```
ggcaccaaag tagttctaga tgacaaggat tatttcctat ttcgtgatgg tgacattctt    300
ggcaagtacg tagactaa                                                   318
```

<210> SEQ ID NO 63
<211> LENGTH: 102
<212> TYPE: PRT
<213> ORGANISM: Artificial Sequence
<220> FEATURE:
<223> OTHER INFORMATION: Synthetic Human Cpn10 with additional
      N-terminal valine (V) residue

<400> SEQUENCE: 63

```
Val Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100
```

<210> SEQ ID NO 64
<211> LENGTH: 102
<212> TYPE: PRT
<213> ORGANISM: Artificial Sequence
<220> FEATURE:
<223> OTHER INFORMATION: Synthetic Human Cpn10 with additional
      N-terminal Leucine (L) residue

<400> SEQUENCE: 64

```
Leu Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100
```

<210> SEQ ID NO 65
<211> LENGTH: 102
<212> TYPE: PRT
<213> ORGANISM: Artificial Sequence
<220> FEATURE:
<223> OTHER INFORMATION: Synthetic Human Cpn10 with additional
      N-terminal isoleucine (I) residue

<400> SEQUENCE: 65

```
Ile Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100
```

<210> SEQ ID NO 66
<211> LENGTH: 102
<212> TYPE: PRT
<213> ORGANISM: Artificial Sequence
<220> FEATURE:
<223> OTHER INFORMATION: Synthetic Human Cpn10 with additional
      N-terminal histidine (H) residue

<400> SEQUENCE: 66

```
His Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100
```

<210> SEQ ID NO 67
<211> LENGTH: 102
<212> TYPE: PRT
<213> ORGANISM: Artificial Sequence
<220> FEATURE:
<223> OTHER INFORMATION: Synthetic Human Cpn10 with additional
      N-terminal phenylalanine (F) residue

<400> SEQUENCE: 67

```
Phe Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80
```

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 68
<211> LENGTH: 102
<212> TYPE: PRT
<213> ORGANISM: Artificial Sequence
<220> FEATURE:
<223> OTHER INFORMATION: Synthetic Human Cpn10 with additional
      N-terminal tyrosine (Y) residue

<400> SEQUENCE: 68

Tyr Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 69
<211> LENGTH: 102
<212> TYPE: PRT
<213> ORGANISM: Artificial Sequence
<220> FEATURE:
<223> OTHER INFORMATION: Synthetic Human Cpn10 with additional
      N-terminal tryptophan (W) residue

<400> SEQUENCE: 69

Trp Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 70
<211> LENGTH: 102
<212> TYPE: PRT
<213> ORGANISM: Artificial Sequence
<220> FEATURE:
<223> OTHER INFORMATION: Synthetic Human Cpn10 with additional
      N-terminal cysteine (C) residue

```
<400> SEQUENCE: 70

Cys Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 71
<211> LENGTH: 102
<212> TYPE: PRT
<213> ORGANISM: Artificial Sequence
<220> FEATURE:
<223> OTHER INFORMATION: Synthetic Human Cpn10 with additional
      N-terminal threonine (T) residue

<400> SEQUENCE: 71

Thr Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 72
<211> LENGTH: 102
<212> TYPE: PRT
<213> ORGANISM: Artificial Sequence
<220> FEATURE:
<223> OTHER INFORMATION: Synthetic Human Cpn10 with additional
      N-terminal aspartic acid (D) residue

<400> SEQUENCE: 72

Asp Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
```

```
                65                  70                  75                  80
Val Val Leu Asp Asp Lys Asp Tyr Phe Leu Phe Arg Asp Gly Asp Ile
                    85                  90                  95

Leu Gly Lys Tyr Val Asp
            100

<210> SEQ ID NO 73
<211> LENGTH: 102
<212> TYPE: PRT
<213> ORGANISM: Artificial Sequence
<220> FEATURE:
<223> OTHER INFORMATION: Synthetic Human Cpn10 with additional
      N-terminal aparagine (N) residue

<400> SEQUENCE: 73

Asn Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 74
<211> LENGTH: 102
<212> TYPE: PRT
<213> ORGANISM: Artificial Sequence
<220> FEATURE:
<223> OTHER INFORMATION: Synthetic Human Cpn10 with additional
      N-terminal glutamic acid (E) residue

<400> SEQUENCE: 74

Glu Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 75
<211> LENGTH: 102
<212> TYPE: PRT
<213> ORGANISM: Artificial Sequence
<220> FEATURE:
<223> OTHER INFORMATION: Synthetic Human Cpn10 with additional
```

N-terminal glutamine (Q) residue

<400> SEQUENCE: 75

Gln Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 76
<211> LENGTH: 103
<212> TYPE: PRT
<213> ORGANISM: Artificial Sequence
<220> FEATURE:
<223> OTHER INFORMATION: Synthetic Human Cpn10 with additional
      N-terminal glutamine (Q) and serine (S) residues

<400> SEQUENCE: 76

Gln Ser Ala Gly Gln Ala Phe Arg Lys Phe Leu Pro Leu Phe Asp Arg
1               5                   10                  15

Val Leu Val Glu Arg Ser Ala Ala Glu Thr Val Thr Lys Gly Gly Ile
            20                  25                  30

Met Leu Pro Glu Lys Ser Gln Gly Lys Val Leu Gln Ala Thr Val Val
        35                  40                  45

Ala Val Gly Ser Gly Ser Lys Gly Lys Gly Gly Glu Ile Gln Pro Val
    50                  55                  60

Ser Val Lys Val Gly Asp Lys Val Leu Leu Pro Glu Tyr Gly Gly Thr
65                  70                  75                  80

Lys Val Val Leu Asp Asp Lys Asp Tyr Phe Leu Phe Arg Asp Gly Asp
                85                  90                  95

Ile Leu Gly Lys Tyr Val Asp
            100

<210> SEQ ID NO 77
<211> LENGTH: 104
<212> TYPE: PRT
<213> ORGANISM: Artificial Sequence
<220> FEATURE:
<223> OTHER INFORMATION: Synthetic Human Cpn10 with additional
      N-terminal methionine (M), glutamine(Q) and serine (S) residues

<400> SEQUENCE: 77

Gln Ser Met Ala Gly Gln Ala Phe Arg Lys Phe Leu Pro Leu Phe Asp
1               5                   10                  15

Arg Val Leu Val Glu Arg Ser Ala Ala Glu Thr Val Thr Lys Gly Gly
            20                  25                  30

Ile Met Leu Pro Glu Lys Ser Gln Gly Lys Val Leu Gln Ala Thr Val
        35                  40                  45

Val Ala Val Gly Ser Gly Ser Lys Gly Lys Gly Gly Glu Ile Gln Pro
    50                  55                  60

```
Val Ser Val Lys Val Gly Asp Lys Val Leu Pro Glu Tyr Gly Gly
 65                  70                  75                  80

Thr Lys Val Val Leu Asp Asp Lys Asp Tyr Phe Leu Phe Arg Asp Gly
                 85                  90                  95

Asp Ile Leu Gly Lys Tyr Val Asp
            100
```

<210> SEQ ID NO 78
<211> LENGTH: 103
<212> TYPE: PRT
<213> ORGANISM: Artificial Sequence
<220> FEATURE:
<223> OTHER INFORMATION: Synthetic Human Cpn10 with two additional
      N-terminal methione (M) Residues

<400> SEQUENCE: 78

```
Met Met Ala Gly Gln Ala Phe Arg Lys Phe Leu Pro Leu Phe Asp Arg
 1               5                  10                  15

Val Leu Val Glu Arg Ser Ala Ala Glu Thr Val Thr Lys Gly Gly Ile
             20                  25                  30

Met Leu Pro Glu Lys Ser Gln Gly Lys Val Leu Gln Ala Thr Val Val
         35                  40                  45

Ala Val Gly Ser Gly Ser Lys Gly Lys Gly Gly Glu Ile Gln Pro Val
     50                  55                  60

Ser Val Lys Val Gly Asp Lys Val Leu Leu Pro Glu Tyr Gly Gly Thr
 65                  70                  75                  80

Lys Val Val Leu Asp Asp Lys Asp Tyr Phe Leu Phe Arg Asp Gly Asp
                 85                  90                  95

Ile Leu Gly Lys Tyr Val Asp
            100
```

<210> SEQ ID NO 79
<211> LENGTH: 95
<212> TYPE: PRT
<213> ORGANISM: Artificial Sequence
<220> FEATURE:
<223> OTHER INFORMATION: Synthetic Cpn10 mutant lacking the Beta-hairpin
      roof turn (53-KGKGGEI-59), in addition this construct contains an
      extra N-terminal Alanine residue (Ala-Cpn10-deltaroof)

<400> SEQUENCE: 79

```
Ala Ala Gly Gln Ala Phe Arg Lys Phe Leu Pro Leu Phe Asp Arg Val
 1               5                  10                  15

Leu Val Glu Arg Ser Ala Ala Glu Thr Val Thr Lys Gly Gly Ile Met
             20                  25                  30

Leu Pro Glu Lys Ser Gln Gly Lys Val Leu Gln Ala Thr Val Val Ala
         35                  40                  45

Val Gly Ser Gly Ser Gln Pro Val Ser Val Lys Val Gly Asp Lys Val
     50                  55                  60

Leu Leu Pro Glu Tyr Gly Gly Thr Lys Val Val Leu Asp Asp Lys Asp
 65                  70                  75                  80

Tyr Phe Leu Phe Arg Asp Gly Asp Ile Leu Gly Lys Tyr Val Asp
                 85                  90                  95
```

<210> SEQ ID NO 80
<211> LENGTH: 102
<212> TYPE: PRT
<213> ORGANISM: Artificial Sequence
<220> FEATURE:
<223> OTHER INFORMATION: Synthetic Human Cpn10 mutant with residues K53 and K55 changed to M53 and M55 respectively. This construct contains an extra N-terminal Alanine residue (Ala-Cpn10-K53M,K55M)

<400> SEQUENCE: 80

Ala Ala Gly Gln Ala Phe Arg Lys Phe Leu Pro Leu Phe Asp Arg Val
1               5                   10                  15
Leu Val Glu Arg Ser Ala Ala Glu Thr Val Thr Lys Gly Gly Ile Met
            20                  25                  30
Leu Pro Glu Lys Ser Gln Gly Lys Val Leu Gln Ala Thr Val Val Ala
        35                  40                  45
Val Gly Ser Gly Ser Met Gly Met Gly Gly Glu Ile Gln Pro Val Ser
50                  55                  60
Val Lys Val Gly Asp Lys Val Leu Leu Pro Glu Tyr Gly Gly Thr Lys
65                  70                  75                  80
Val Val Leu Asp Asp Lys Asp Tyr Phe Leu Phe Arg Asp Gly Asp Ile
                85                  90                  95
Leu Gly Lys Tyr Val Asp
            100

<210> SEQ ID NO 81
<211> LENGTH: 104
<212> TYPE: PRT
<213> ORGANISM: Artificial Sequence
<220> FEATURE:
<223> OTHER INFORMATION: Synthetic Human Cpn10 with additional
      N-terminal Serine (S), Threonine (T) and Glycine (G) residues
      respectively (STG-Cpn10)

<400> SEQUENCE: 81

Ser Thr Gly Ala Gly Gln Ala Phe Arg Lys Phe Leu Pro Leu Phe Asp
1               5                   10                  15
Arg Val Leu Val Glu Arg Ser Ala Ala Glu Thr Val Thr Lys Gly Gly
            20                  25                  30
Ile Met Leu Pro Glu Lys Ser Gln Gly Lys Val Leu Gln Ala Thr Val
        35                  40                  45
Val Ala Val Gly Ser Gly Ser Lys Gly Lys Gly Gly Glu Ile Gln Pro
50                  55                  60
Val Ser Val Lys Val Gly Asp Lys Val Leu Leu Pro Glu Tyr Gly Gly
65                  70                  75                  80
Thr Lys Val Val Leu Asp Asp Lys Asp Tyr Phe Leu Phe Arg Asp Gly
                85                  90                  95
Asp Ile Leu Gly Lys Tyr Val Asp
            100

<210> SEQ ID NO 82
<211> LENGTH: 318
<212> TYPE: DNA
<213> ORGANISM: Artificial Sequence
<220> FEATURE:
<223> OTHER INFORMATION: Synthetic Native cDNA of STG-Cpn10

<400> SEQUENCE: 82
atgagcaccg gcgcaggaca agcgtttaga aagtttcttc cactctttga ccgagtattg      60
gttgaaagga gtgctgctga aactgtaacc aaaggaggca ttatgcttcc agaaaaatct    120
caaggaaaag tattgcaagc aacagtagtc gctgttggat cgggttctaa aggaaagggt    180
ggagagattc aaccagttag cgtgaaagtt ggagataaag ttcttctccc agaatatgga    240
ggcaccaaag tagttctaga tgacaaggat tatttcctat ttagagatgg tgacattctt    300

-continued

```
ggaaagtacg tagactga                                                  318

<210> SEQ ID NO 83
<211> LENGTH: 318
<212> TYPE: DNA
<213> ORGANISM: Artificial Sequence
<220> FEATURE:
<223> OTHER INFORMATION: Synthetic Optimised cDNA of STG-Cpn10

<400> SEQUENCE: 83
atgagcaccg gcgcaggcca agcgtttcgc aagtttcttc cactctttga ccgtgtattg    60
gttgaacgca gtgctgctga aactgtaacc aaaggtggca ttatgcttcc agaaaaatct   120
caaggcaaag tattgcaagc aacagtagtc gctgttggct cgggttctaa aggtaagggt   180
ggcgagattc aaccagttag cgtgaaagtt ggcgataaag ttcttctccc agaatatggt   240
ggcaccaaag tagttctaga tgacaaggat tatttcctat tcgtgatgg tgacattctt    300 ggcaagtacg tagactaa                                                  318

<210> SEQ ID NO 84
<211> LENGTH: 103
<212> TYPE: PRT
<213> ORGANISM: Artificial Sequence
<220> FEATURE:
<223> OTHER INFORMATION: Synthetic Human Cpn10 with additional
      N-terminal Proline (P) and Glycine (G) residues respectively
      (PG-Cpn10)

<400> SEQUENCE: 84

Pro Gly Ala Gly Gln Ala Phe Arg Lys Phe Leu Pro Leu Phe Asp Arg
1               5                   10                  15

Val Leu Val Glu Arg Ser Ala Ala Glu Thr Val Thr Lys Gly Gly Ile
            20                  25                  30

Met Leu Pro Glu Lys Ser Gln Gly Lys Val Leu Gln Ala Thr Val Val
        35                  40                  45

Ala Val Gly Ser Gly Ser Lys Gly Lys Gly Gly Glu Ile Gln Pro Val
    50                  55                  60

Ser Val Lys Val Gly Asp Lys Val Leu Leu Pro Glu Tyr Gly Gly Thr
65                  70                  75                  80

Lys Val Val Leu Asp Asp Lys Asp Tyr Phe Leu Phe Arg Asp Gly Asp
                85                  90                  95

Ile Leu Gly Lys Tyr Val Asp
            100

<210> SEQ ID NO 85
<211> LENGTH: 315
<212> TYPE: DNA
<213> ORGANISM: Artificial Sequence
<220> FEATURE:
<223> OTHER INFORMATION: Synthetic Native cDNA of PG-Cpn10

<400> SEQUENCE: 85
atgccgggcg caggacaagc gtttagaaag tttcttccac tctttgaccg agtattggtt    60
gaaaggagtg ctgctgaaac tgtaaccaaa ggaggcatta tgcttccaga aaaatctcaa   120
ggaaaagtat tgcaagcaac agtagtcgct gttggatcgg gttctaaagg aaagggtgga   180
gagattcaac cagttagcgt gaaagttgga gataaagttc ttctcccaga atatggaggc   240
accaaagtag ttctagatga caaggattat ttcctattta gagatggtga cattcttgga   300
aagtacgtag actga                                                    315
```

```
<210> SEQ ID NO 86
<211> LENGTH: 315
<212> TYPE: DNA
<213> ORGANISM: Artificial Sequence
<220> FEATURE:
<223> OTHER INFORMATION: Synthetic Optimised cDNA of PG-Cpn10 (Gly, Arg
      and stop codons are Optimized in the cDNA)

<400> SEQUENCE: 86
atgccgggcg caggccaagc gtttcgcaag tttcttccac tctttgaccg tgtattggtt      60
gaacgcagtg ctgctgaaac tgtaaccaaa ggtggcatta tgcttccaga aaaatctcaa     120
ggcaaagtat tgcaagcaac agtagtcgct gttggctcgg ttctaaagg taagggtggc     180 gagattcaac cagttagcgt gaaagttggc gataaagttc ttctcccaga atatggtggc    240
accaaagtag ttctagatga caaggattat ttcctatttc gtgatggtga cattcttggc    300
aagtacgtag actaa                                                    315

<210> SEQ ID NO 87
<211> LENGTH: 104
<212> TYPE: PRT
<213> ORGANISM: Artificial Sequence
<220> FEATURE:
<223> OTHER INFORMATION: Synthetic Human Cpn10 with additional
      N-terminal Proline (P), Threonine (T) and Glycine (G) residues
      respectively (PTG-Cpn10)

<400> SEQUENCE: 87

Pro Thr Gly Ala Gly Gln Ala Phe Arg Lys Phe Leu Pro Leu Phe Asp
1               5                   10                  15

Arg Val Leu Val Glu Arg Ser Ala Ala Glu Thr Val Thr Lys Gly Gly
                20                  25                  30

Ile Met Leu Pro Glu Lys Ser Gln Gly Lys Val Leu Gln Ala Thr Val
            35                  40                  45

Val Ala Val Gly Ser Gly Ser Lys Gly Lys Gly Gly Glu Ile Gln Pro
        50                  55                  60

Val Ser Val Lys Val Gly Asp Lys Val Leu Leu Pro Glu Tyr Gly Gly
65                  70                  75                  80

Thr Lys Val Val Leu Asp Asp Lys Asp Tyr Phe Leu Phe Arg Asp Gly
                85                  90                  95

Asp Ile Leu Gly Lys Tyr Val Asp
            100

<210> SEQ ID NO 88
<211> LENGTH: 317
<212> TYPE: DNA
<213> ORGANISM: Artificial Sequence
<220> FEATURE:
<223> OTHER INFORMATION: Synthetic Native cDNA of PTG-Cpn10

<400> SEQUENCE: 88
atgccgaccg gcgcaggaca agcgtttaga aagtttcttc cactctttga ccgagtattg      60
gttgaaagga gtgctgctga aactgtaacc aaaggaggca ttatgcttcc agaaaaatct    120
caaggaaaag tattgcaagc aacagtagtc gctgttggat cgggttctaa aggaaagggt    180
ggagagattc aaccagttag cgtgaaagtt ggagataaag ttcttctccc agaatatgga    240
ggcaccaaag tagttctaga tgacaaggat tatttcctat ttagagatgg tgacattctt    300
ggaaagtacg tagactg                                                  317
```

```
<210> SEQ ID NO 89
<211> LENGTH: 318
<212> TYPE: DNA
<213> ORGANISM: Artificial Sequence
<220> FEATURE:
<223> OTHER INFORMATION: Synthetic Optimised cDNA of PTG-Cpn10 (Gly, Arg
      and stop codons are Optimized in the cDNA)

<400> SEQUENCE: 89
atgccgaccg gcgcaggcca agcgtttcgc aagtttcttc cactctttga ccgtgtattg      60
gttgaacgca gtgctgctga aactgtaacc aaaggtggca ttatgcttcc agaaaaatct    120
caaggcaaag tattgcaagc aacagtagtc gctgttggct cgggttctaa aggtaagggt    180
ggcgagattc aaccagttag cgtgaaagtt ggcgataaag ttcttctccc agaatatggt    240
ggcaccaaag tagttctaga tgacaaggat tatttcctat tcgtgatgg tgacattctt    300 ggcaagtacg tagactaa                                                  318

<210> SEQ ID NO 90
<211> LENGTH: 104
<212> TYPE: PRT
<213> ORGANISM: Artificial Sequence
<220> FEATURE:
<223> OTHER INFORMATION: Synthetic Human Cpn10 with additional
      N-terminal Methionine (M), Glutamine (Q) and Serine (S) residues
      respectively (MQS-Cpn10)

<400> SEQUENCE: 90

Met Gln Ser Ala Gly Gln Ala Phe Arg Lys Phe Leu Pro Leu Phe Asp
1               5                   10                  15

Arg Val Leu Val Glu Arg Ser Ala Ala Glu Thr Val Thr Lys Gly Gly
            20                  25                  30

Ile Met Leu Pro Glu Lys Ser Gln Gly Lys Val Leu Gln Ala Thr Val
        35                  40                  45

Val Ala Val Gly Ser Gly Ser Lys Gly Lys Gly Gly Glu Ile Gln Pro
    50                  55                  60

Val Ser Val Lys Val Gly Asp Lys Val Leu Leu Pro Glu Tyr Gly Gly
65                  70                  75                  80

Thr Lys Val Val Leu Asp Asp Lys Asp Tyr Phe Leu Phe Arg Asp Gly
                85                  90                  95

Asp Ile Leu Gly Lys Tyr Val Asp
            100

<210> SEQ ID NO 91
<211> LENGTH: 315
<212> TYPE: DNA
<213> ORGANISM: Artificial Sequence
<220> FEATURE:
<223> OTHER INFORMATION: Synthetic Native cDNA of MQS-Cpn10

<400> SEQUENCE: 91
atgcagagcg caggacaagc gtttagaaag tttcttccac tctttgaccg agtattggtt      60
gaaaggagtg ctgctgaaac tgtaaccaaa ggaggcatta tgcttccaga aaaatctcaa    120
ggaaaagtat tgcaagcaac agtagtcgct gttggatcgg gttctaaagg aaagggtgga    180
gagattcaac cagttagcgt gaaagttgga gataaagttc ttctcccaga atatggaggc    240
accaaagtag ttctagatga caaggattat ttcctattta gagatggtga cattcttgga    300
aagtacgtag actga                                                     315

<210> SEQ ID NO 92
```

<211> LENGTH: 315
<212> TYPE: DNA
<213> ORGANISM: Artificial Sequence
<220> FEATURE:
<223> OTHER INFORMATION: Synthetic Optimised cDNA of MQS-Cpn10 (Gly, Arg and stop codons are optimised in the cDNA)

<400> SEQUENCE: 92

```
atgcagagcg caggccaagc gtttcgcaag tttcttccac tctttgaccg tgtattggtt    60
gaacgcagtg ctgctgaaac tgtaaccaaa ggtggcatta tgcttccaga aaaatctcaa   120
ggcaaagtat tgcaagcaac agtagtcgct gttggctcgg gttctaaagg taagggtggc   180
gagattcaac cagttagcgt gaaagttggc gataaagttc ttctcccaga atatggtggc   240
accaaagtag ttctagatga caaggattat ttcctatttc gtgatggtga cattcttggc   300
aagtacgtag actaa                                                   315
```

<210> SEQ ID NO 93
<211> LENGTH: 105
<212> TYPE: PRT
<213> ORGANISM: Artificial Sequence
<220> FEATURE:
<223> OTHER INFORMATION: Synthetic Human Cpn10 with additional N-terminal Methionine (M), Glutamine (Q), Serine (S) and Methionine (M) residues respectively (MQSM-Cpn10)

<400> SEQUENCE: 93

```
Met Gln Ser Met Ala Gly Gln Ala Phe Arg Lys Phe Leu Pro Leu Phe
1               5                  10                  15

Asp Arg Val Leu Val Glu Arg Ser Ala Ala Glu Thr Val Thr Lys Gly
            20                  25                  30

Gly Ile Met Leu Pro Glu Lys Ser Gln Gly Lys Val Leu Gln Ala Thr
        35                  40                  45

Val Val Ala Val Gly Ser Gly Ser Lys Gly Lys Gly Gly Glu Ile Gln
    50                  55                  60

Pro Val Ser Val Lys Val Gly Asp Lys Val Leu Leu Pro Glu Tyr Gly
65                  70                  75                  80

Gly Thr Lys Val Val Leu Asp Asp Lys Asp Tyr Phe Leu Phe Arg Asp
                85                  90                  95

Gly Asp Ile Leu Gly Lys Tyr Val Asp
            100                 105
```

<210> SEQ ID NO 94
<211> LENGTH: 318
<212> TYPE: DNA
<213> ORGANISM: Artificial Sequence
<220> FEATURE:
<223> OTHER INFORMATION: Synthetic Native cDNA of MQSM-Cpn10

<400> SEQUENCE: 94

```
atgcagagca tggcaggaca agcgtttaga aagtttcttc cactctttga ccgagtattg    60
gttgaaagga gtgctgctga aactgtaacc aaaggaggca ttatgcttcc agaaaaatct   120
caaggaaaag tattgcaagc aacagtagtc gctgttggat cgggttctaa aggaaagggt   180
ggagagattc aaccagttag cgtgaaagtt ggagataaag ttcttctccc agaatatgga   240
ggcaccaaag tagttctaga tgacaaggat tatttcctat ttagagatgg tgacattctt   300
ggaaagtacg tagactga                                                318
```

<210> SEQ ID NO 95
<211> LENGTH: 318

<212> TYPE: DNA
<213> ORGANISM: Artificial Sequence
<220> FEATURE:
<223> OTHER INFORMATION: Synthetic Optimised cDNA of MQSM-Cpn10 (Gly,
      Arg and stop codons are optimised in the cDNA)

<400> SEQUENCE: 95

```
atgcagagca tggcaggcca agcgtttcgc aagtttcttc cactctttga ccgtgtattg    60
gttgaacgca gtgctgctga aactgtaacc aaaggtggca ttatgcttcc agaaaaatct  120
caaggcaaag tattgcaagc aacagtagtc gctgttggct cgggttctaa aggtaagggg  180
ggcgagattc aaccagttag cgtgaaagtt ggcgataaag ttcttctccc agaatatggt  240
ggcaccaaag tagttctaga tgacaaggat tatttcctat tcgtgatgg tgacattctt  300
ggcaagtacg tagactaa                                                318
```

<210> SEQ ID NO 96
<211> LENGTH: 103
<212> TYPE: PRT
<213> ORGANISM: Artificial Sequence
<220> FEATURE:
<223> OTHER INFORMATION: Synthetic Human Cpn10 with additional
      N-terminal Serine(S) and Glycine G) residues respectively
      (SG-Cpn10)

<400> SEQUENCE: 96

```
Ser Gly Ala Gly Gln Ala Phe Arg Lys Phe Leu Pro Leu Phe Asp Arg
1               5                   10                  15
Val Leu Val Glu Arg Ser Ala Ala Glu Thr Val Thr Lys Gly Gly Ile
            20                  25                  30
Met Leu Pro Glu Lys Ser Gln Gly Lys Val Leu Gln Ala Thr Val Val
        35                  40                  45
Ala Val Gly Ser Gly Ser Lys Gly Lys Gly Gly Glu Ile Gln Pro Val
    50                  55                  60
Ser Val Lys Val Gly Asp Lys Val Leu Leu Pro Glu Tyr Gly Gly Thr
65                  70                  75                  80
Lys Val Val Leu Asp Asp Lys Asp Tyr Phe Leu Phe Arg Asp Gly Asp
                85                  90                  95
Ile Leu Gly Lys Tyr Val Asp
            100
```

<210> SEQ ID NO 97
<211> LENGTH: 315
<212> TYPE: DNA
<213> ORGANISM: Artificial Sequence
<220> FEATURE:
<223> OTHER INFORMATION: Synthetic Native cDNA of SG-Cpn10

<400> SEQUENCE: 97

```
atgagcggcg caggacaagc gtttagaaag tttcttccac tctttgaccg agtattggtt    60
gaaaggagtg ctgctgaaac tgtaaccaaa ggaggcatta tgcttccaga aaaatctcaa   120
ggaaaagtat tgcaagcaac agtagtcgct gttggatcgg ttctaaagg aaagggtgga   180
gagattcaac cagttagcgt gaaagttgga gataaagttc ttctcccaga atatggaggc   240
accaaagtag ttctagatga caaggattat ttcctattta gagatggtga cattcttgga   300
aagtacgtag actga                                                   315
```

<210> SEQ ID NO 98
<211> LENGTH: 315
<212> TYPE: DNA

```
<213> ORGANISM: Artificial Sequence
<220> FEATURE:
<223> OTHER INFORMATION: Optimised cDNA of SG-Cpn10

<400> SEQUENCE: 98
atgagcggcg caggccaagc gtttcgcaag tttcttccac tctttgaccg tgtattggtt      60
gaacgcagtg ctgctgaaac tgtaaccaaa ggtggcatta tgcttccaga aaaatctcaa     120
ggcaaagtat tgcaagcaac agtagtcgct gttggctcgg gttctaaagg taagggtggc     180
gagattcaac cagttagcgt gaaagttggc gataaagttc ttctcccaga atatggtggc     240
accaaagtag ttctagatga caaggattat ttcctatttc gtgatggtga cattcttggc     300
aagtacgtag actaa                                                      315
```